US009738901B2

(12) United States Patent
Scheller et al.

(10) Patent No.: US 9,738,901 B2
(45) Date of Patent: Aug. 22, 2017

(54) REGULATION OF GALACTAN SYNTHASE EXPRESSION TO MODIFY GALACTAN CONTENT IN PLANTS

(71) Applicant: THE REGENTS OF THE UNIVERSITY OF CALIFORNIA, Oakland, CA (US)

(72) Inventors: Henrik Vibe Scheller, Millbrae, CA (US); Joshua L. Heazlewood, Fitzroy North (AU)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/399,880

(22) PCT Filed: May 10, 2013

(86) PCT No.: PCT/US2013/040632
§ 371 (c)(1),
(2) Date: Nov. 7, 2014

(87) PCT Pub. No.: WO2013/170201
PCT Pub. Date: Nov. 14, 2013

(65) Prior Publication Data
US 2015/0099872 A1    Apr. 9, 2015

Related U.S. Application Data

(60) Provisional application No. 61/645,537, filed on May 10, 2012.

(51) Int. Cl.
*C12N 15/82* (2006.01)
*C12N 9/10* (2006.01)

(52) U.S. Cl.
CPC ....... *C12N 15/8246* (2013.01); *C12N 9/1051* (2013.01)

(58) Field of Classification Search
None
See application file for complete search history.

(56) References Cited

U.S. PATENT DOCUMENTS

| | | | | |
|---|---|---|---|---|
| 6,992,236 | B1 * | 1/2006 | Famodu | C12N 9/92 435/183 |
| 7,585,818 | B2 * | 9/2009 | Segura | C08B 37/0087 166/280.1 |
| 8,183,432 | B2 * | 5/2012 | Takagi | C12N 15/8216 435/320.1 |
| 2005/0086712 | A1 | 4/2005 | Meyer et al. | |
| 2006/0107345 | A1 * | 5/2006 | Alexandrov | C07K 14/415 800/278 |
| 2010/0154078 | A1 | 6/2010 | Powell et al. | |
| 2010/0186118 | A1 | 7/2010 | Bloksberg et al. | |
| 2010/0199380 | A1 | 8/2010 | Frankard et al. | |

FOREIGN PATENT DOCUMENTS

WO     2012/103555 A2     8/2012

OTHER PUBLICATIONS

Holland et al (2000 Plant Physiology 123:1313-1323.*
International Search Report and Written Opinion dated Jan. 16, 2014 of International Patent Application No. PCT/US2013/040632, 22 pages.
UnitProtKB_O22807_ARATH, Expressed protein, last modified Jun. 1, 2002 www.uniprot.org/uniprot/O22807.
Espley et al., "Multiple Repeats of a Promoter Segment Causes Transcription Factor Autoregulation in Red Apples", *Plant Cell*, vol. 21, No. 1, pp. 168-183 (2009).
Harholt et al., "Arabinan Deficient 1 is a in Putative Arabinosyltransferase Involved in Biosynthesis of Pectic Arabinan in Arabidopsis", *Plant Physiology*, vol. 140, pp. 49-58 (2006).
Harholt et al., "Biosynthesis of Pectin", *Plant Physiology*, vol. 153, pp. 384-395 (2010).
Harholt et al., "ARAD proteins associated with pectic Arabinan biosynthesis form complexes when transiently overexpressed in planta", *Planta*, vol. 236, No. 1, pp. 115-128 (2012).
Jensen et al., "Identification of a Xylogalacturonan Xylosyltransferase Involved in Pectin Biosynthesis in Arabidopsis", *The Plant Cell*, vol. 20, pp. 1289-1302 (2008).
Kotake et al., "Bifunctional cytosolic UDP-glucose 4-epimerases catalyse the interconversion between UDP-D-xylose and UDP-L-arabinose in plants", *Biochem J.*, vol. 424, pp. 169-177 (2009).
Mitsuda et al., "NAC Transcription Factors, NST1 and NST3, Are Key Regulators of the Formation of Secondary Walls in Woody Tissues of Arabidopsis", *Plant Cells*, vol. 19, No. 1, pp. 270-280 (2007).
Petersen et al., "Engineering of plants with improved properties as biofuels feedstocks by vessel-specific complementation of xylan biosynthesis mutants", *Biotechnology for Biofuels*, vol. 5, No. 84, 19 pages (2012)
Sterling et al., "Functional identification of an Arabidopsis pectin biosynthetic homogalacturonan galacturonosyltransferase", *PNAS*, vol. 103, No. 13, pp. 5236-5241 (2006)

* cited by examiner

*Primary Examiner* — Brent Page
(74) *Attorney, Agent, or Firm* — Kilpatrick Townsend & Stockton LLP

(57) ABSTRACT

The disclosure provides methods of engineering plants to modulate galactan content. Specifically, the disclosure provides methods for engineering a plant to increase the galactan content in a plant tissue by inducing expression of beta-1,4-galactan synthase (GALS), modulated by a heterologous promoter. Further disclosed are the methods of modulating expression level of GALS under the regulation of a transcription factor, as well as overexpression of UDP-galactose epimerse in the same plant tissue. Tissue specific promoters and transcription factors can be used in the methods are also provided.

15 Claims, 24 Drawing Sheets

T-DNA Insertion Lines

GALS1 (At2g33570)

GALS2 (At5g44670)

GALS3 (At4g20170)

REGULATION OF GALACTAN SYNTHASE EXPRESSION TO MODIFY GALACTAN CONTENT IN PLANTS

CROSS-REFERENCES TO RELATED APPLICATIONS

This application is a National Stage of International Application No. PCT/US2013/040632, filed May 10, 2013, and which claims the benefit of U.S. provisional application no. 61/645,537, filed May 10, 2012, which application is herein incorporated by reference.

REFERENCE TO SEQUENCE LISTING

This application includes a Sequence Listing as a text file named "77429-924593-SEQLIST.txt" created Aug. 24, 2016, and containing 195,367 bytes. The material contained in this text file is incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support wider Contract No. DE-AC02-05CH11231 awarded by the U.S. Department of Energy. The government has certain rights in this invention.

BACKGROUND OF THE INVENTION

Plant cell wall is the only source of cellulose for the paper industry and is a promising source of sugar for lignocellulosic biofuels. The utilization of plants to convert solar energy into transportable and storable energy will have a positive impact on the environment, since using plants can help to drastically reduce the utilization of fossil-derived fuels, can reduce carbon emission into the atmosphere, and even can contribute to carbon sequestration. However, even if lignocellulosic biofuels will be beneficial for the environment, the cost to produce them is still not cost-effective, mainly due to the expensive raw sugar derived from plant cell wall. The low density, recalcitrance to enzymatic hydrolysis, and low ratio of hexoses to pentoses in the biomass are the main contributors to the sugar cost because they impact transportation cost and require high amount of energy and chemicals. Therefore, improving the digestibility of the raw biomass and improving recovery of sugars that are more readily fermentable from biomass will have an important beneficial impact on the cost of lignocellulosic biofuels production.

Plant cell walls are predominantly composed of different polysaccharides, which can be grouped into cellulose, hemicelluloses and pectin. Pectin is a class of polysaccharide characterized by a high content of galacturonic acid residues and consists of two major types: homogalacturonan entirely composed of alpha-1,4-linked galacturonosyl residues, and rhamnogalacturonan I (RGI) composed of a backbone of alternating rhamnose and galacturonic acid residues with sidechains composed of arabinan and beta-1,4-galactan (Mohnen, 2008; Harholt et al., 2010). Other domains of pectin include RGII, a complex structure with numerous different sugars, and xylogalacturonan, which is a type of HG with sidechains consisting of single xylosyl residues. It has been estimated that as many as 67 different transferases are required for bioynthesis of pectin (Mohnen, 2008; Harholt et al., 2010) but so far only one has been unambiguously indentified, namely the homogalacturonan galacturonosyltransferase GAUT1 (Sterling et al., 2006). A likely xylogalacturonan xylosyltransferase designated XGD1 has also been described but the final proof of activity of the isolated XGD1 protein has not been provided (Jensen et al., 2008). Biosynthesis of the arabinan sidechains on RGI involves the ARAD1 and ARAD2 proteins, but if they are arabinosyltransferases or work in a different way has not been determined (Harholt et al., 2006; Harholt et al., 2012). Beta-1,4-galactan constitutes a large part of pectin and of the total cell wall. However, little is known about the enzymes in plants responsible for its synthesis.

BRIEF SUMMARY OF THE INVENTION

This invention is based, in part, on the discovery that enzymes in the glycosyltransferases family 92 play a role in modulating galactan levels in plant cell wall. Plants harboring loss-of function mutations in genes encoding the GT92 family members of the invention, showed a decreased content of beta-1,4-galactan. The plants did not have an apparent growth phenotype, but pectin was more easily extracted from the cell walls of the mutants, and saccharification was improved. Overexpression of galactan synthase increased galactan content of cell walls. The invention thus provides methods employing plant GT92 family members for modulating galactan content in plants; and compositions and method of using such compositions.

BRIEF DESCRIPTION OF THE DRAWINGS

FIG. 1 provides an alignment of various GT92 family members. The polypeptide sequence for each protein extends across the FIG. 1 continuation pages. The SEQ ID NO for the protein is provided on the first page of FIG. 1.

OE, 35S:F-UGE2 GalS1#1, 35S:F-UGE2+GalS1#2, 35S:F-UGE2+GalS1#5, pIRX5-UGE2+GalS1#4, pIRX5-UGE2+GalS1#3, pIRX5-UGE2+GalS1#14.

Figure 7:
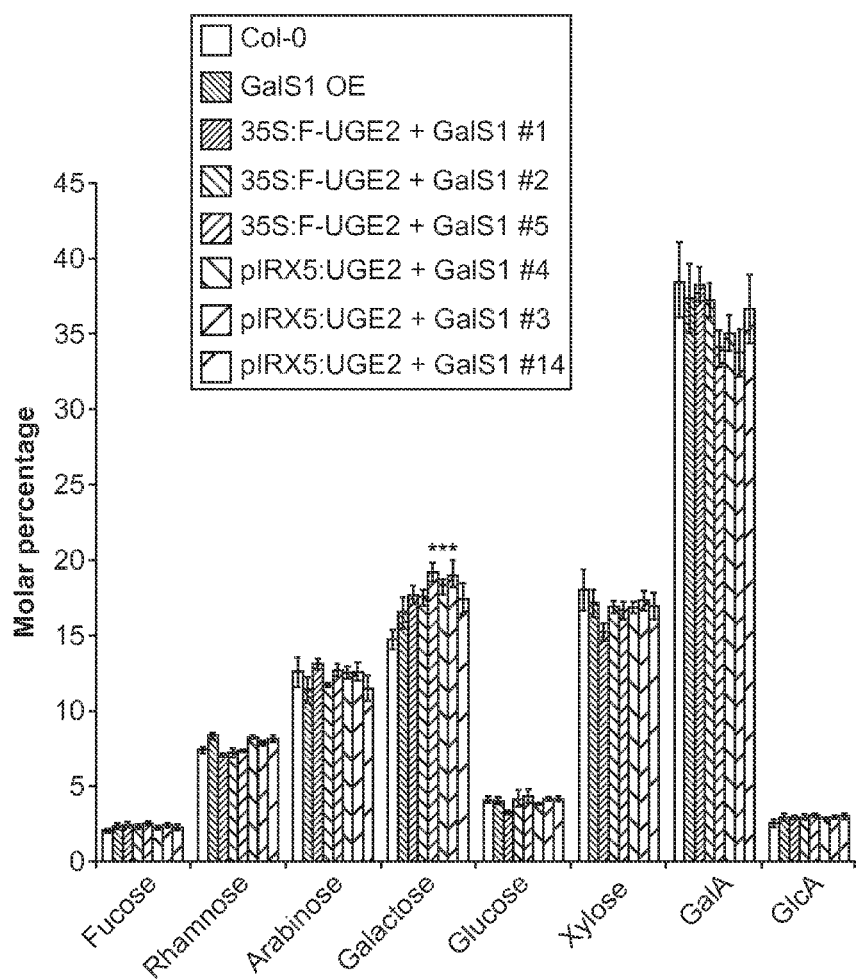
FIG. 7 provides illustrative data showing monosaccharide composition of leaf cell wall of plants coexpressing GalS1 and NST1-2A-AtUGE2 under the control of the fiber specific pIRX5 promoter or the constitutive 35S promoter. Asterisks mark the three lines that have significantly different galactose molar percentages (t-test, pBonf<0.0083). Sugar levels are described as molar percentage, ±SE (n=6). From left to right for each sugar, the bars are: Col-0. GalS1
Figure 8:
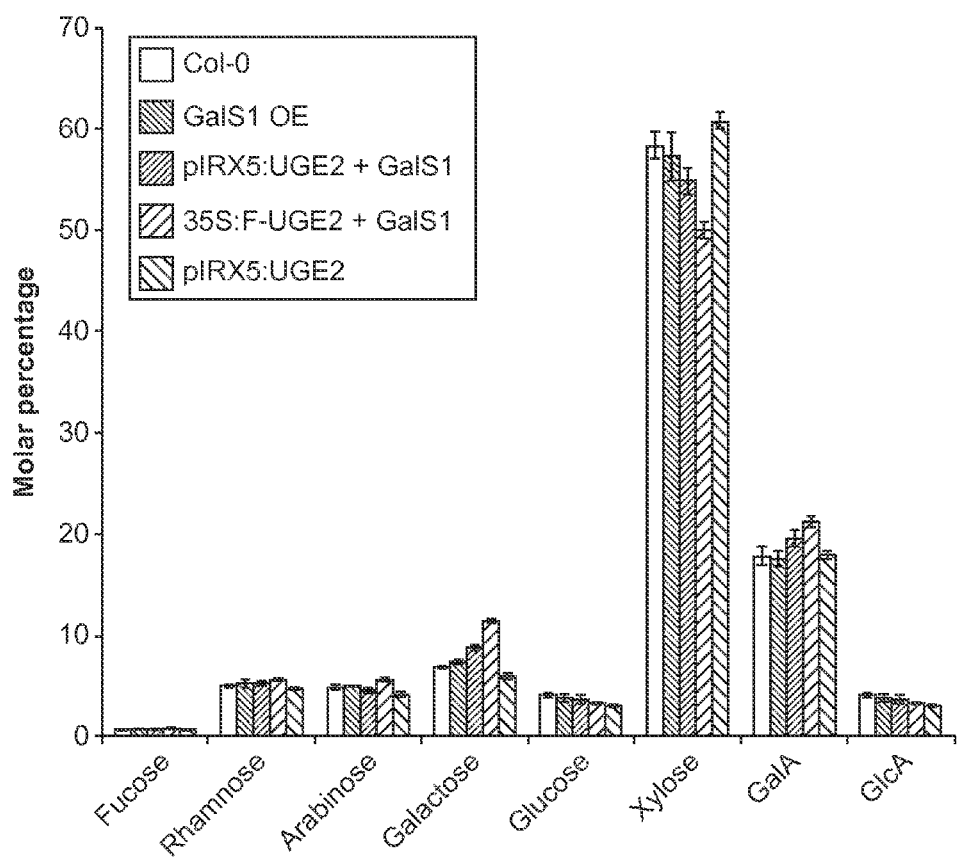

FIG. 8 provides illustrative data showing monosaccharide composition of cell walls of stems of plants coexpressing GaslS1 and AtUGE2. As in FIGS. 7 and 8, expression of UGE2 under the pIRX5 promoter was done with a construct that simultaneously expresses the NST1 fiber-specific transcription factor, separated from UGE2 with a 2A domain. From left to right for each sugar, the bars are: Col-0 GalS1 OE, pIRX5:UGE2+GalS1, 35S:F-UGE2+GalS1, pIrX5:1UGE2

Figure 9:
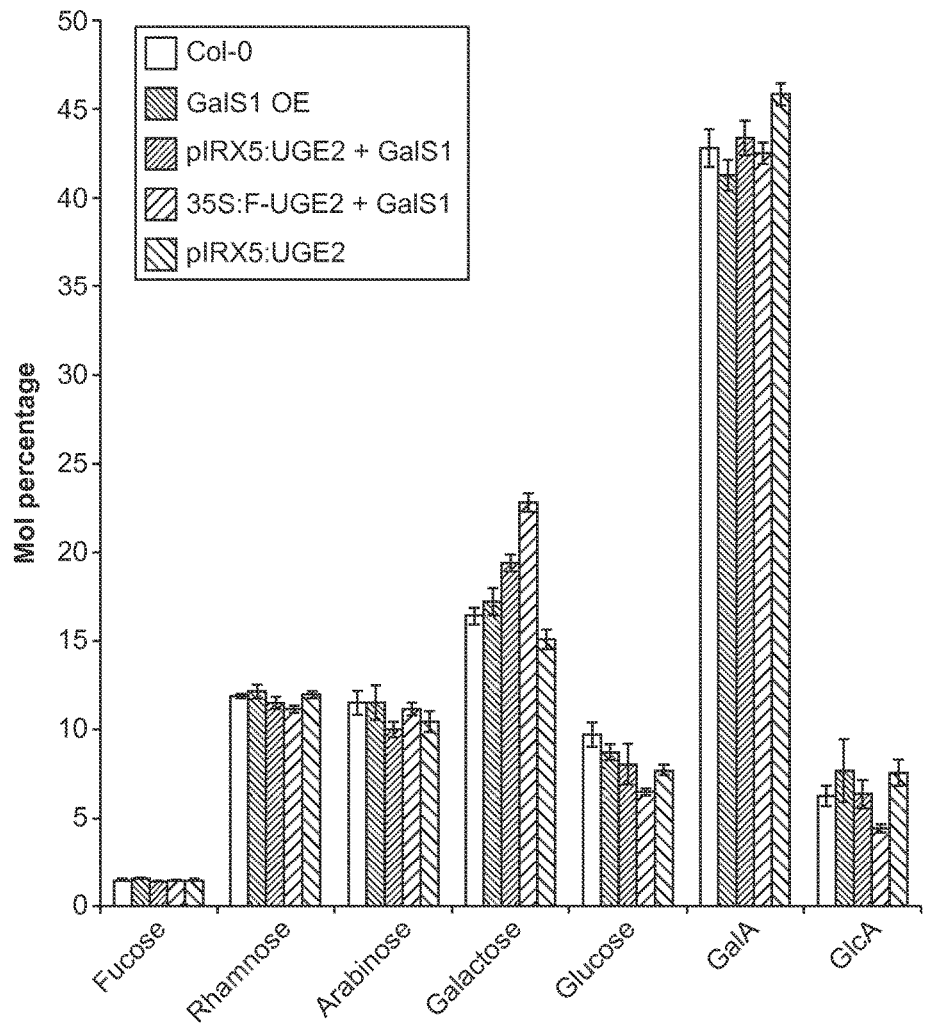

FIG. 9 provides data showing monosaccharide composition in cell walls of stems omitting xylose from the data. From left to right for each sugar, the bars are: Col-0, GalS1 OE, pIRX5: UGE2+GalS1, 35S:F-UGE2 GalS1, pIrXS: UGE2

DETAIL DESCRIPTION OF THE INVENTION

I. Definitions

As used herein, the term "galactan synthase" or "beta-1,4, galactan synthase" or "GALS" are used interchangeably to refer to an enzyme that is involved in the elongation of beta-1,4-galactan and has beta-1,4 galactosyltransferase activity. In the current invention, a galactan synthase is a glycosyltransferase in the family GT92. The term encompasses polymorphic variants, alleles, mutants, and interspecies homologs to the specific polypeptides described herein. A nucleic acid that encodes a galactan synthase refers to a gene, pre-mRNA, mRNA, and the like, including nucleic acids encoding polymorphic variants, alleles, mutants, and interspecies homologs of the particular amino acid sequences described herein. Thus, in some embodiments, a galactan synthase encodes a polypeptide having an amino acid sequence that has at least 50% amino acid sequence identity, or at least 55%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200 or more amino acids, or over the length of the entire polypeptide, to any one of the amino acid sequences shown in SEQ ID NOS:1, 2, or 3; or to any one of the plant amino acid sequences SEQ ID NOS:1-39 shown in FIG. 1; or to any one of the amino acid sequence SEQ ID NO:1-27 shown in FIG. 1. Examples of gene ids and accession numbers of galactan synthases are shown in the annotation for SEQ ID NOS:42-44. SEQ ID NOS:42-44 provide illustrations of GALS nucleic acids suitable for use in the invention.

As used herein, the term "transcription factor that regulates the production of components of a biosynthetic pathway" or "master transcription factor" refers to a transcription factor that regulates expression of one or of multiple genes in a biosynthetic pathway.

The term "downstream target," when used in the context of a downstream target of a transcription factor that regulates a component of a biosynthetic pathway of interest refers to a gene or protein whose expression is directly or indirectly regulated by the transcription factor. In some embodiments, the downstream target is a gene or protein that is directly or indirectly upregulated by the transcription factor. In some embodiments, the downstream target is a gene or protein that is directly or indirectly downregulated by the transcription factor.

The terms "increased level of activity," or "increased activity" refer interchangeably to an increase in the amount of activity of GALS protein in a plant engineered to increase GALS compared to the amount of activity in a wild-type (i.e., naturally occurring) plant. In some embodiments, increased activity results from increased expression levels. An increased level of activity or increased level of expression can be an increase in the amount of activity or expression of GALS in a plant genetically modified to overexpress GALS of at least 10%, 20%, 30%, 40%, 50%, 60%, 70%, 80%, or 90% or greater compared to a wildtype plant. In some embodiments, the increased GALS activity or expression is localized to one or more tissues of the engineered plant, such as the xylem cells with secondary cell walls. Increased expression or activity of a GALS gene or protein can be assessed by any number of assays, including, but not limited to, measuring the level of RNA encoded by the GALS gene, the level of protein GALS protein, the levels of GALS enzymatic activity, or by measuring galactan content of a plant tissue.

The terms "reduced level of activity," "reduced activity" and "decreased activity" refer interchangeably to a reduction in the amount of activity of GALS protein in a plant engineered to decrease GALS compared to the amount of activity in a wild-type (i.e., naturally occurring) plant. In sonic embodiments, reduced activity results from reduced expression levels. A reduced level of activity or a reduced level of expression can be a reduction in the amount of activity or expression of GALS of at least 10%, 20%, 30%, 40%, 50%, 60%, 70%, 80%, or, 90% or greater, In some embodiments, the reduced level of activity or reduced level of expression occurs, throughout all the tissues of the engineered plant. In some embodiments, the reduction in the amount of activity or expression is localized to one or more tissues of the engineered plant, such as the cell wall. In some embodiments, the GALS is not reduced in amount, but is modified in amino acid sequence so that the enzymatic activity is reduced directly or indirectly. Decreased expression or activity of a GALS gene or protein can be assessed by any number of assays, including, but not limited to, measuring the level of RNA encoded by the GALS gene, the level of protein GALS protein, the levels of GALS enzymatic activity, or by measuring galactan content of a plant tissue.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, phosphoramidate, phosphorothioate, phosphorodithioate, O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, a polynucleotide encoding a GALS polypepitde may have a sequence that is at least 50%, 55%, 60%, 65%, 70%, 75%, 80%, 85%, 90%, 91%, 92%, 93%, 94%, 95%, 96%, 97%, 98%, or 99% identical to a sequence of SEQ ID NO:42, SEQ ID NO:43, or SEQ ID NO:44.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may he adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero. a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Set. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and ¯N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of bath strands. For amino acid sequences, the BLASTP program uses as defaults a word size (W) of 3, an expectation (E) of 10, and the BLOSUM62 scoring matrix (see Heinikoff & Henikoff, *Proc. Natl. Acad. Sci, USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$ and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are illustrative conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V), and
6) Phenylalanine (F), Tyrosine (Y), Tryptophan (W).
(see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular plants species, but also encompasses a promoter from a corresponding gene in other plant species.

A "constitutive promoter" in the context of this invention refers to a promoter that is capable of initiating transcription in nearly all cell types, whereas a "cell type-specific promoter" or "tissue-specific promoter" initiates transcription only in one or a few particular cell types or groups of cells forming a tissue. In some embodiments, a promoter is tissue-specific if the transcription levels initiated by the promoter in the cell wall are at least 2-fold, 3-fold, 4-fold, 5-fold, 6-fold, 7-fold, 8-fold, 9-fold, 10-fold, 50-fold, 100-fold, 500-fold, 1000-fold higher or more as compared to the transcription levels initiated by the promoter in non-cell wall tissues A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promater (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a GALS protein operably linked to a heterologous promoter. In some embodiments, an expression cassette comprises a polynucleotide sequence encoding a GALS protein that is targeted to a position in a plant genome such that expression of the polynucleotide sequence is driven by a promoter that is present in the plant The term "plant" as used herein can refer to a whole plant or part of a plant, e.g., seeds, and includes plants of a variety of ploidy levels, including aneuploid, polyploid, diploid and haploid. The term "plant part," as used herein, refers to shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like), as well as individual plant cells, groups of plant cells (e.g., cultured plant cells), protoplasts, plant extracts, and seeds. The class of plants that can be used in the methods of the invention is generally as broad as the class of higher and lower plants amenable to transformation techniques, including angiosperms (monocotyledonous and dicotyledonous plants), gymnosperms, ferns, bryophytes, and multicellular algae.

The term "biomass," as used herein, refers to plant material that is processed to provide a product, e.g., a biofuel such as ethanol, or livestock feed, or a cellulose for paper and pulp industry products. Such plant material can include whole plants, or parts of plants, e.g., stems, leaves, branches, shoots, roots, tubers, and the like.

The term "increased cell wall deposition" in the context of galactan deposition refers to an increased amount of galactan in a cell wall that is produced in an engineered plant of the present invention as compared to a wild-type (i.e., naturally occurring) plant. In the current invention, galactan deposition is typically considered to be increased when the amount of galactan in the cell wall is increased by at least 10%, at least 20, 30%, 40%, 50%, 60%, 70%, 80%, 90% or more relative to the amount of galactan in the cell wall in a wild-type plant. The amount of galactan can be assessed using any method known in the art, including using an antibody that specifically binds galactan or enzymatic or chemical analyses.

The term "saccharification reaction" refers to a process of converting biomass, usually cellulosic or lignocellulosic biomass, into monomeric sugars, such as glucose and xylose.

The term "soluble sugar" refers to monomeric, dimeric, or trimeric sugar that produced from the saccharification of biomass.

The term "increased amount," when referring to an amount of sugar or soluble sugar obtained from an engineered plant of the present invention, refers to an increase in the amount or yield of sugar that is obtained from saccharification of biomass per amount of starting material, in comparison to corresponding biomass from a wild-type (i.e., naturally occurring) plant. In the context of the present invention, "corresponding biomass from a wild-type plant" refers to plant material that is from the same part of the plant as the biomass from a plant engineered to have modified galactan levels. As understood in the art, increased amount or increased yield is based upon comparisons of the same amount of corresponding plant material.

The term "conversion reaction," as used herein, refers to a reaction that converts biomass into a form of bioenergy. Examples of conversion reactions include, but are not limited to, combustion (burning), gasification, pyrolysis, and polysaccharide hydrolysis (enzymatic or chemical).

The term "increased production," when referring to an amount of bioenergy production obtained from an engineered plant of the present invention, refers to an increased amount of bioenergy that is produced from subjecting biomass from an engineered plant to a conversion reaction (e.g., combustion, gasification, pyrolysis, or polysaccharide hydrolysis) as compared to the amount of bioenergy that is produced from corresponding biomass from a wild-type (i.e., naturally occurring) plant.

Introduction

Galactan is one of the major cell wall polysaccharides. Galactans are composed of hexoses that are easily fermented, which is in contrast to the hemicellulose xylan, which is the naturally most abundant non-cellulosic component of biomass. In addition, beta-1,4-galactan is likely to be more easily degraded by enzymes than xylan, which has a more complex structure and is crosslinked with other cell wall components. Prior to this invention, no biosynthetic enzyme has been identified for galactan. In one aspect, the invention provides a method of engineering plants to increase galactan content, e.g., to improve biofuel potential. Plants can be engineered to overexpress galactan by genetically modifying a plant to overexpress one or more GALS genes as described herein. Typically, overexpression is targeted to cell wall using a tissue-specific promoter. An example of a method for fine-tuning GALS expression to increase expression in the cell wall is taught in PCT/US2012/023182, which is incorporated by reference.

A plant that is engineered to overexpress GALS may also be engineered to overexpress a UDP-galactose epimerase (more commonly referred to as a UDP-glucose epimerase). Such epimerases are well known in the art. Examples of epimerase genes are described by Barber et al., *J. Biol. Chem.* 281:17276-17285, 2006 and Kotake et al., *Biochem.* 424:169-177, 2009, each of which is incorporated by reference. An example of an epimerase polypeptide sequence (Kotake et al.,) is provided in SEQ ID NO:45.

In a further aspect, a plant may be further modified to alter the enzymes that synthesize galactan substrates. Such enzymes could include UDP-glucose pyrophosphorylase and other non-specific UDP-sugar pyrophosphorylases.

In a further aspect, the invention provides a method of decreasing beta-1,4-galactan in a plant, e.g., to increase pectin yield in a plant such as a tuber. Decreasing galactan content can be achieved by inhibiting expression of at least one GALS gene in the plant.

The invention additionally provides methods of using genetically modified plants that overexpress or have reduced levels of GALS activity and methods of using such plants.

GALS Nucleic Acid Sequences

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009).

GALS nucleic acid and polypeptide sequences suitable for use in the invention include GALS nucleic acid sequences that encode a plant GALS polypeptide as illustrated in any of SEQ NO:1-39, or a substantially identical variants. Such a variant typically has at least 60%, often at least 70%, or at least 75%, 80%, 85%, or 90% identity to any one of SEQ ID NOS:1-39, In some embodiments, the nucleic acid encodes a GALS polypeptide of one of SEQ ID NOS:1-28, or a substantially identical variant thereof. Such a variant typically has at least 60%, often at least 70%, or at least 75%, 80%, 85%, or 90% identity to any one of SEQ ID NOS:1-28. In some embodiments, the nucleic acid encodes a GALS polypeptide of one of SEQ ID NOS:1-3, or a substantially identical variant thereof. Such a variant typically has at least 60%, often at least 70%, or at least 75%, 80%, 85%, or 90% identity to SEQ ID NO:1, SEQ ID NO:2, or SEQ ID NO:3.

Figure 1:
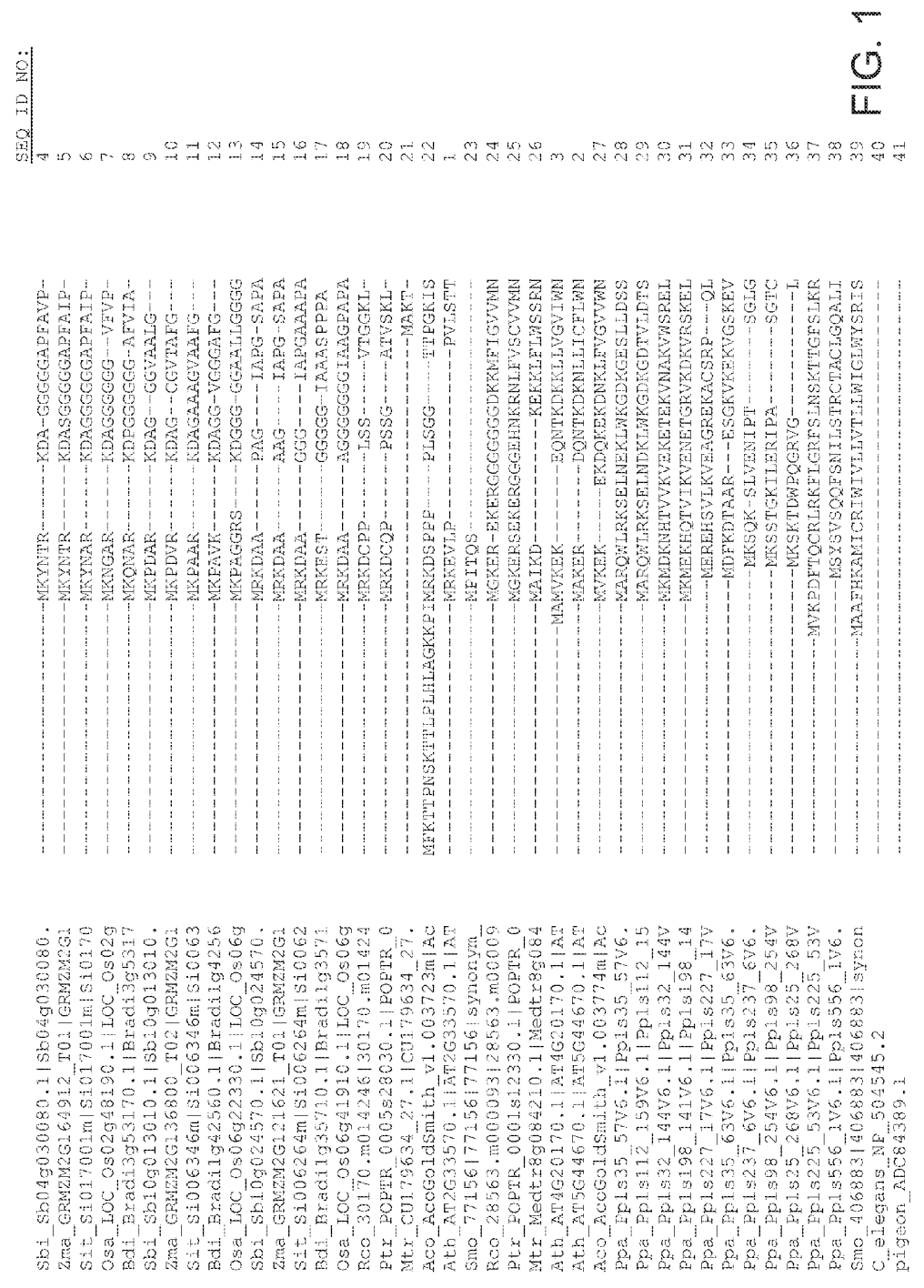
Figure 1:
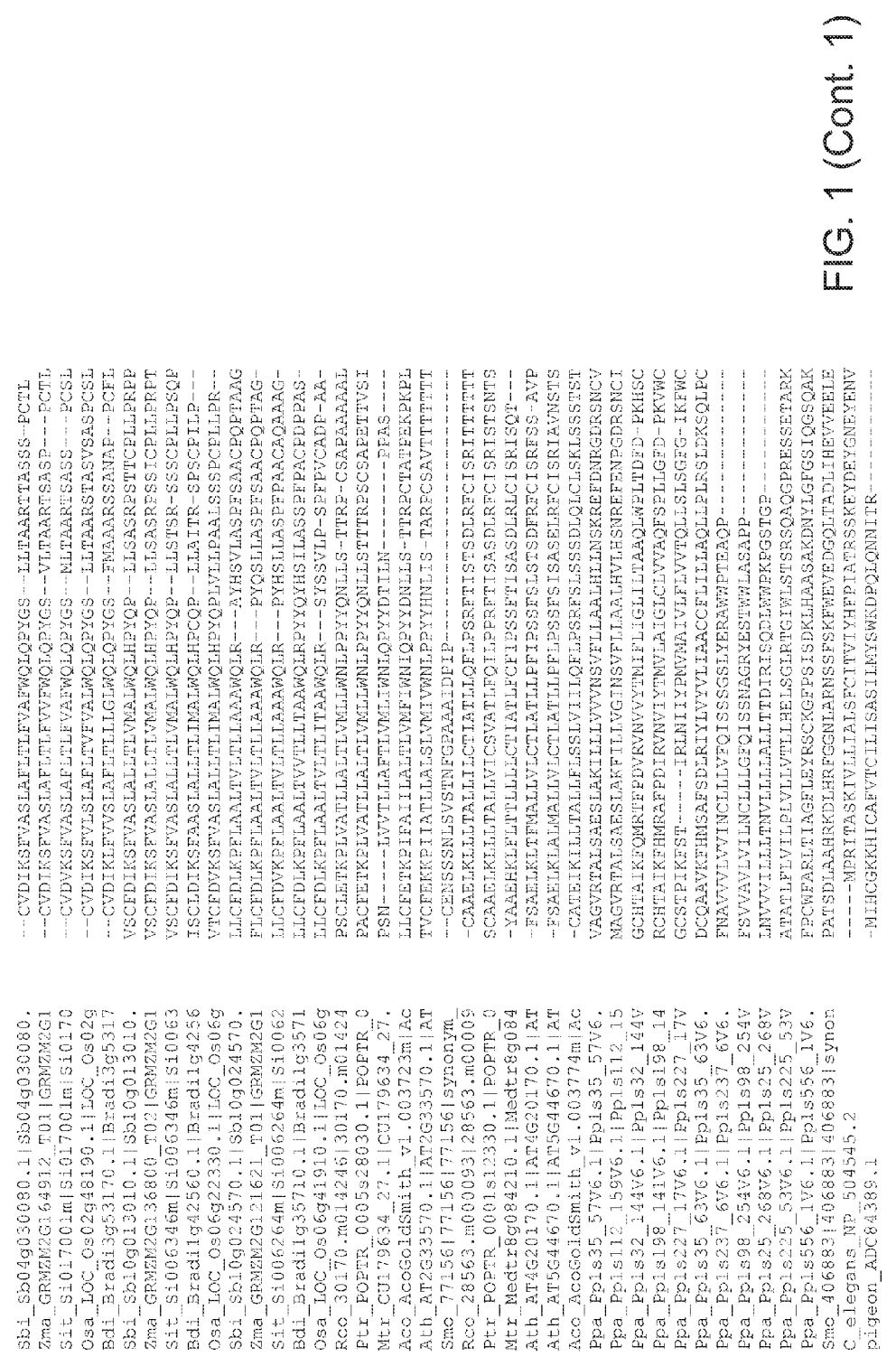
Figure 1:
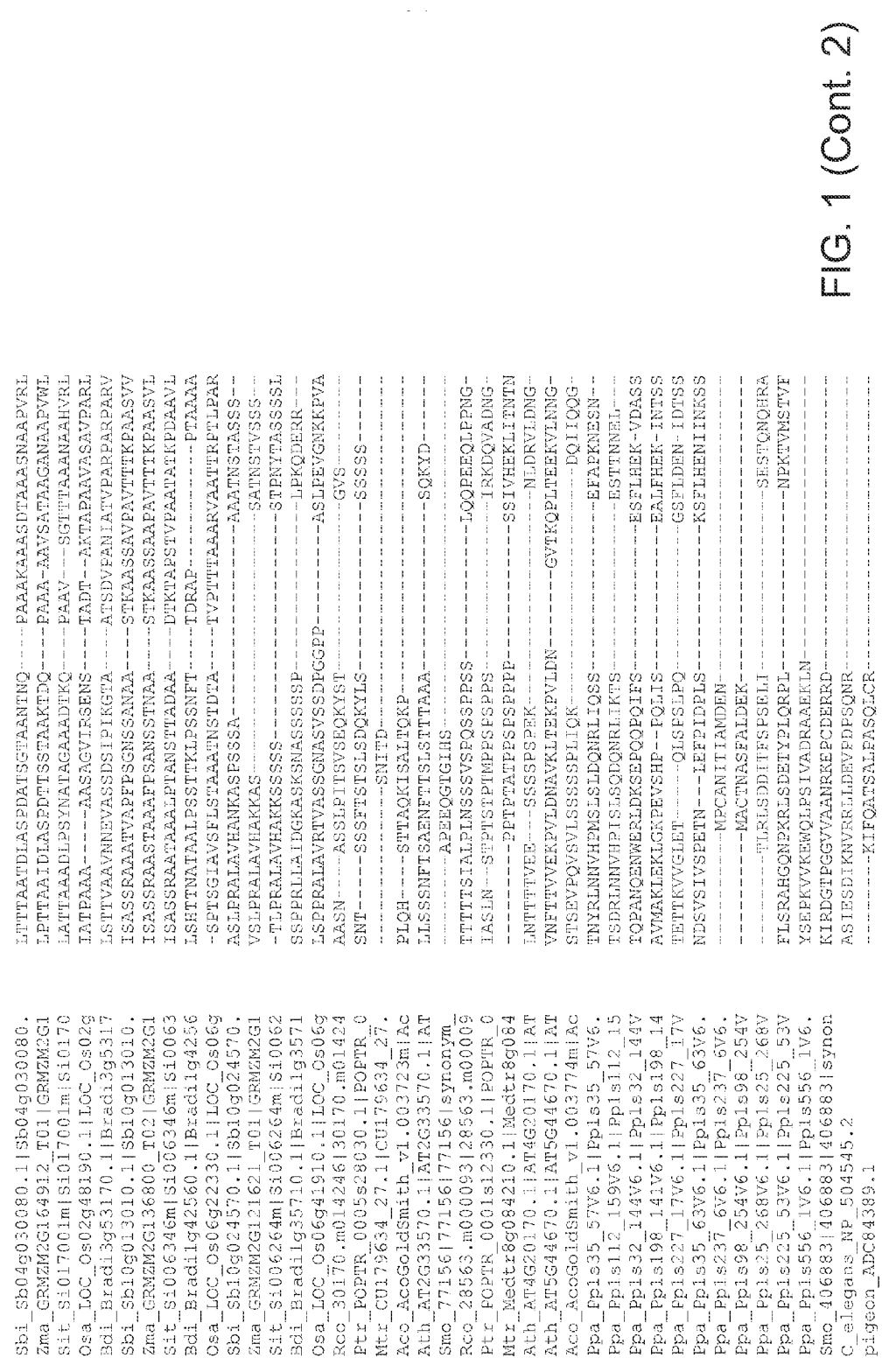
Figure 1:
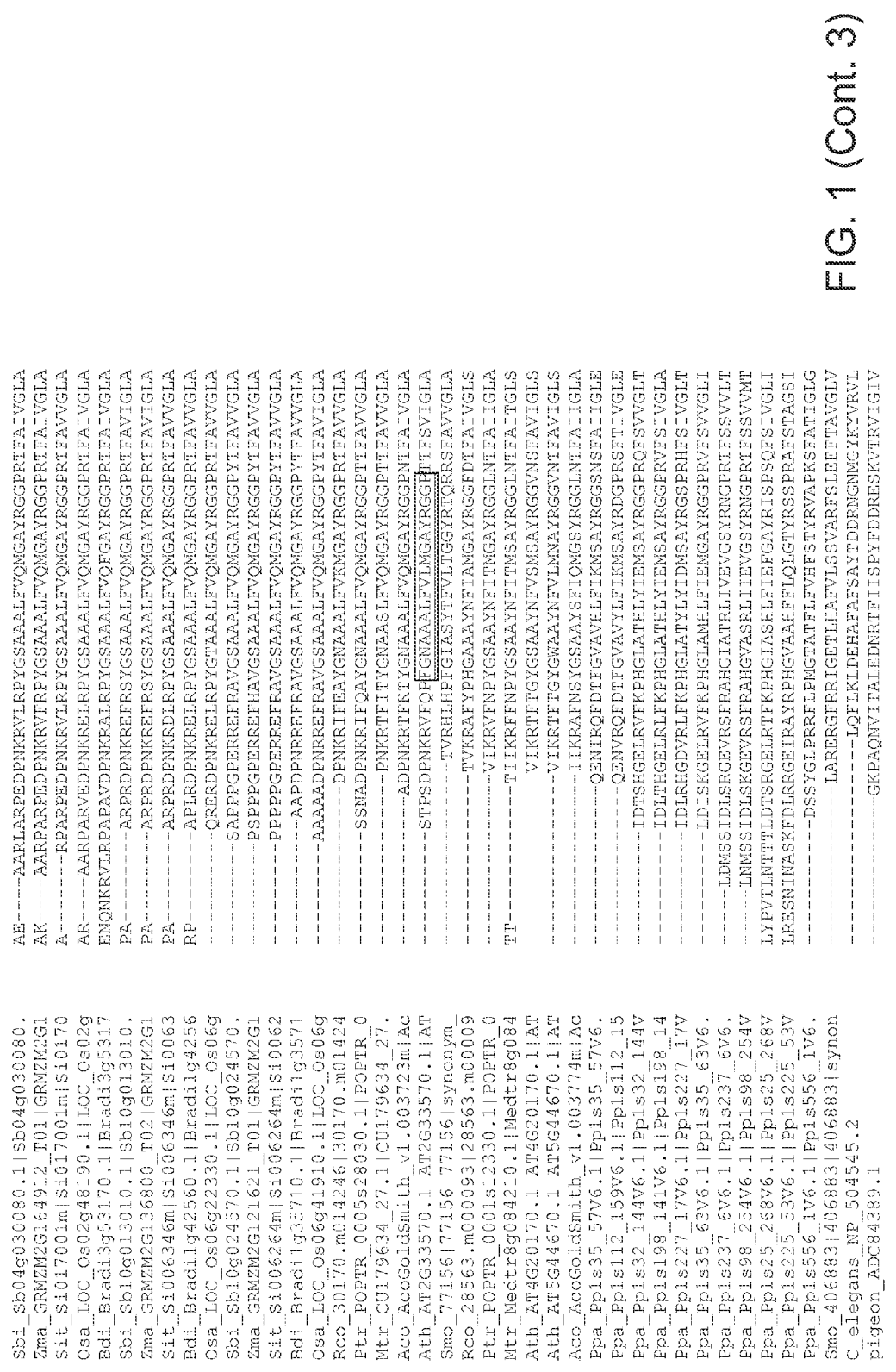
Figure 1:
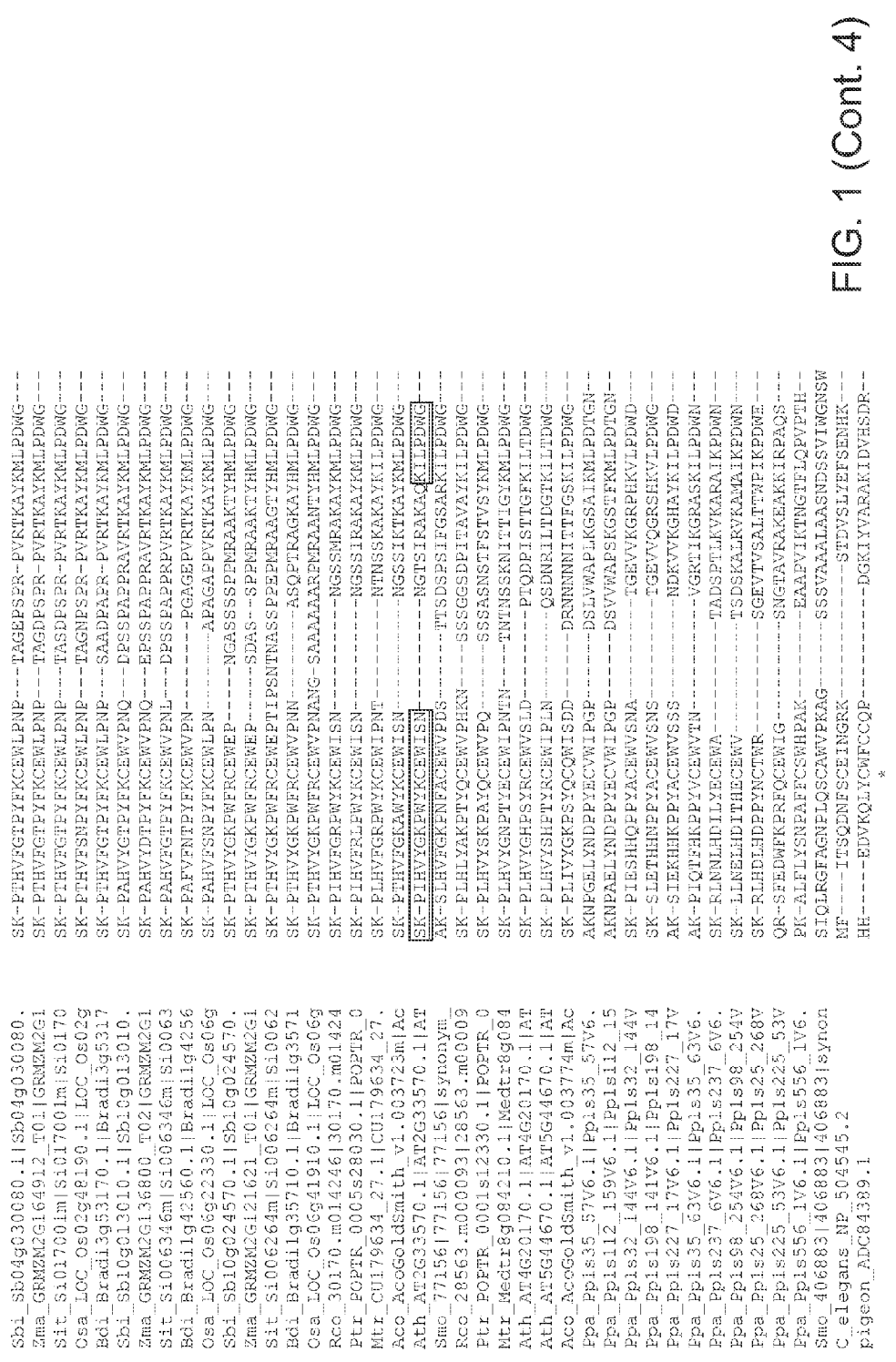
Figure 1:
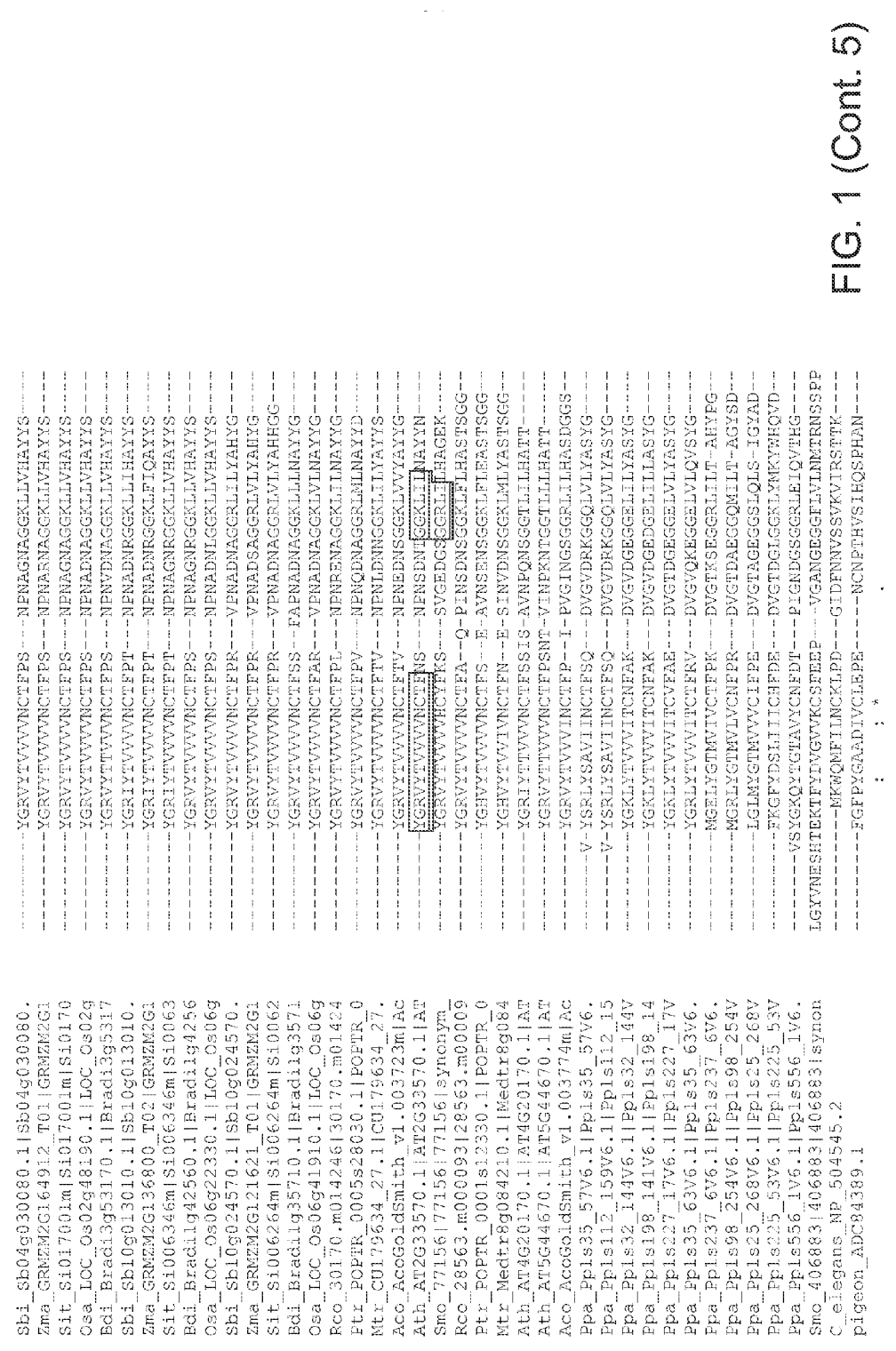
Figure 1:
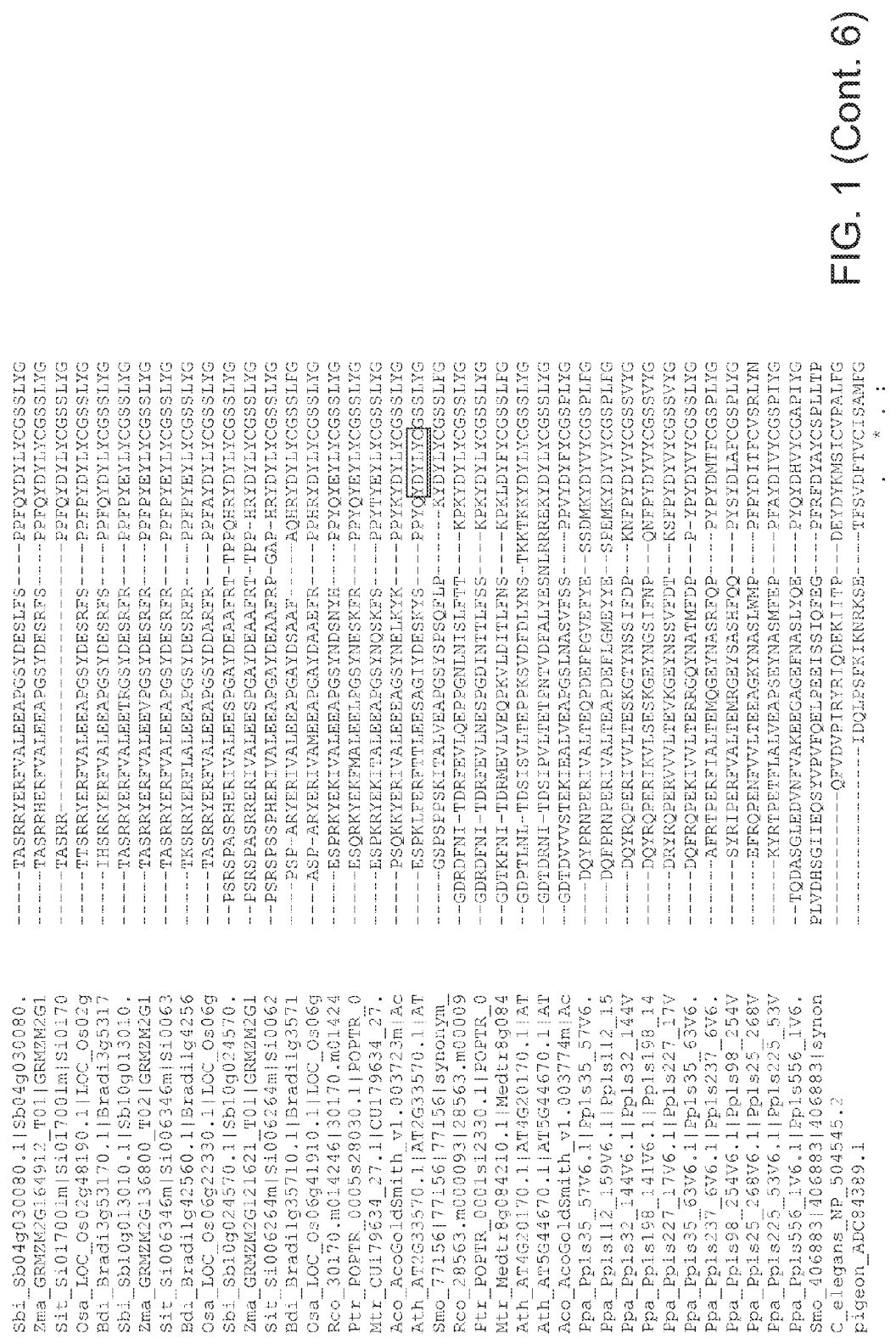
Figure 1:
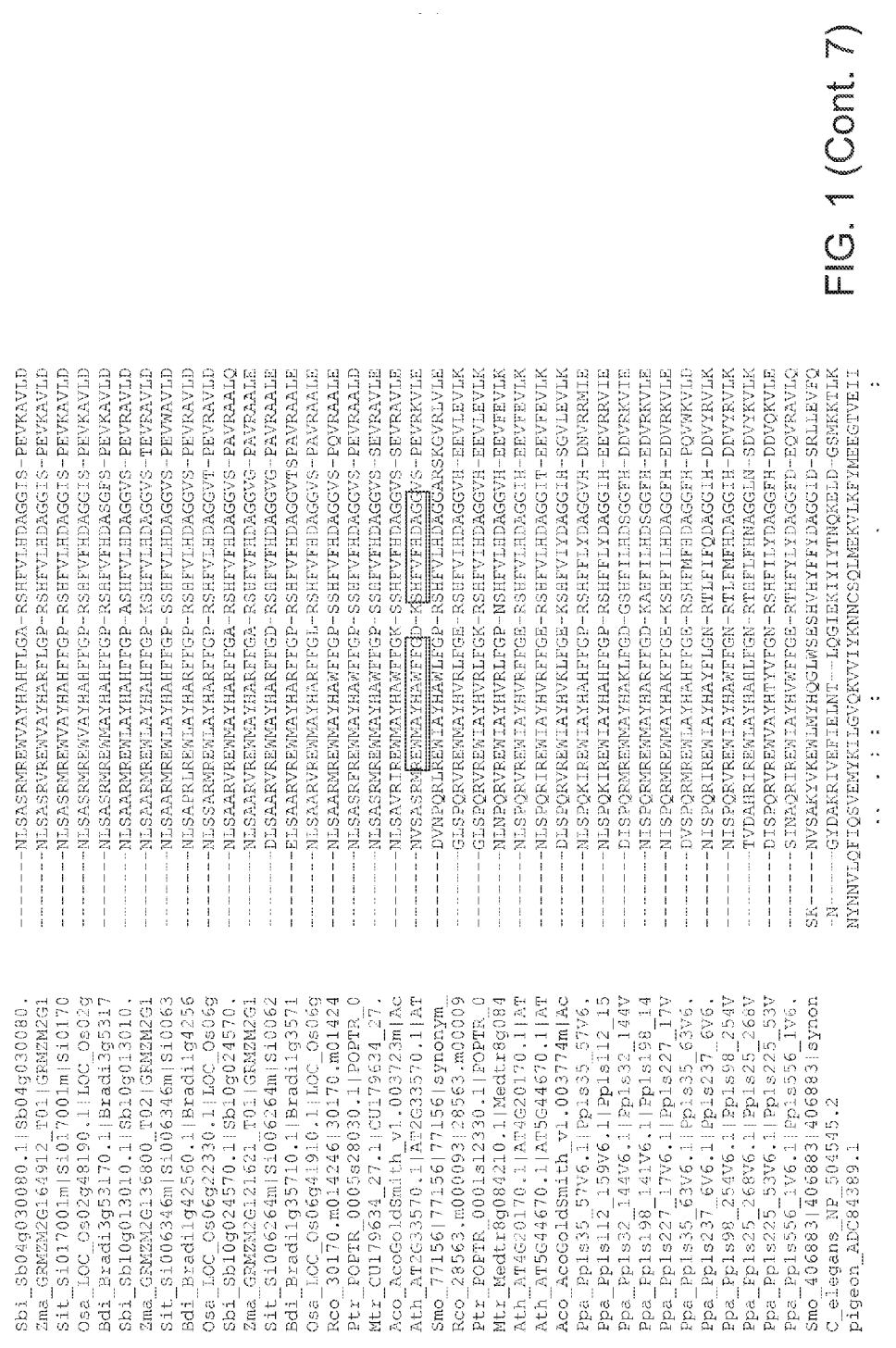
Figure 1:
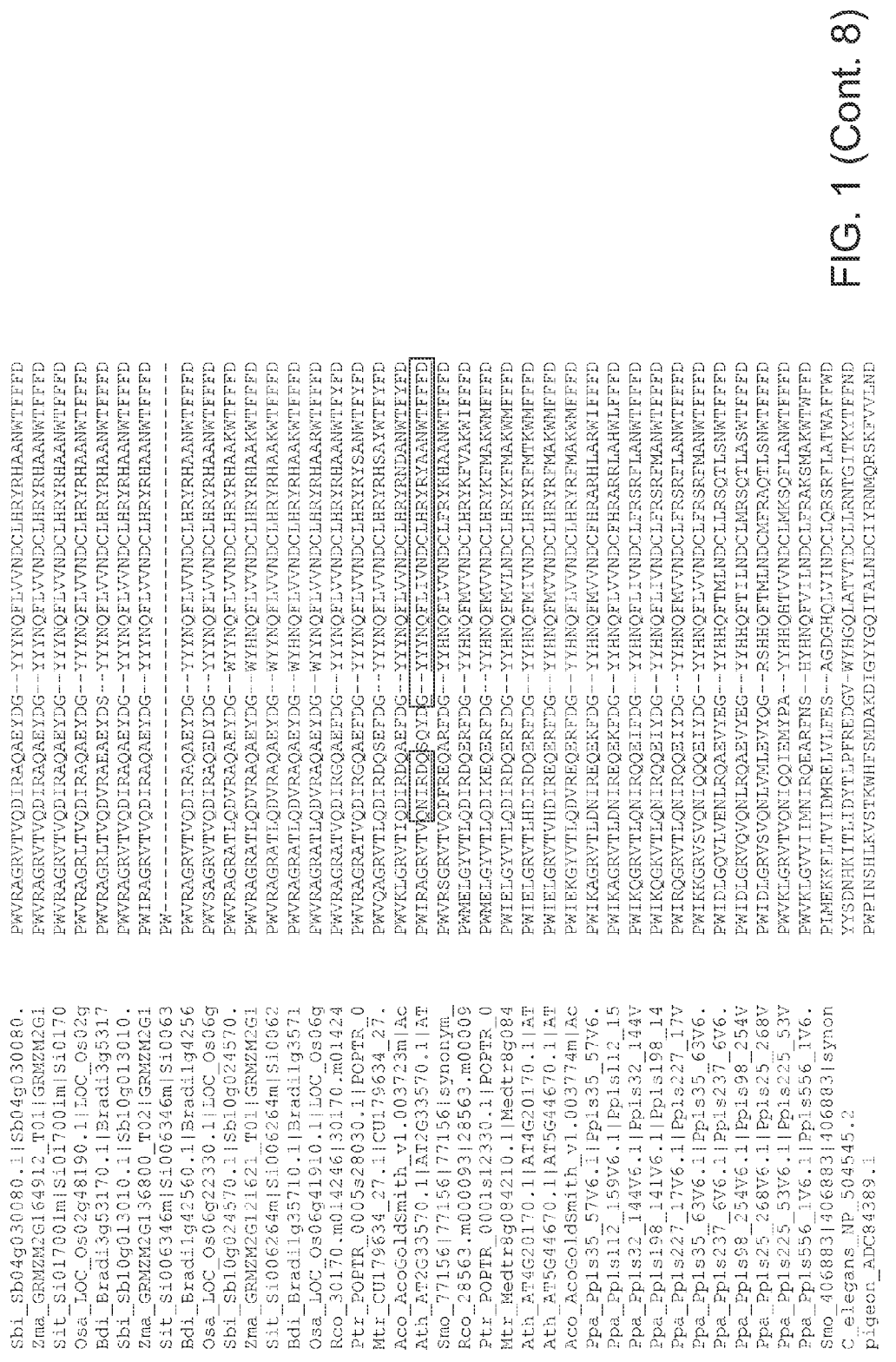
Figure 1:
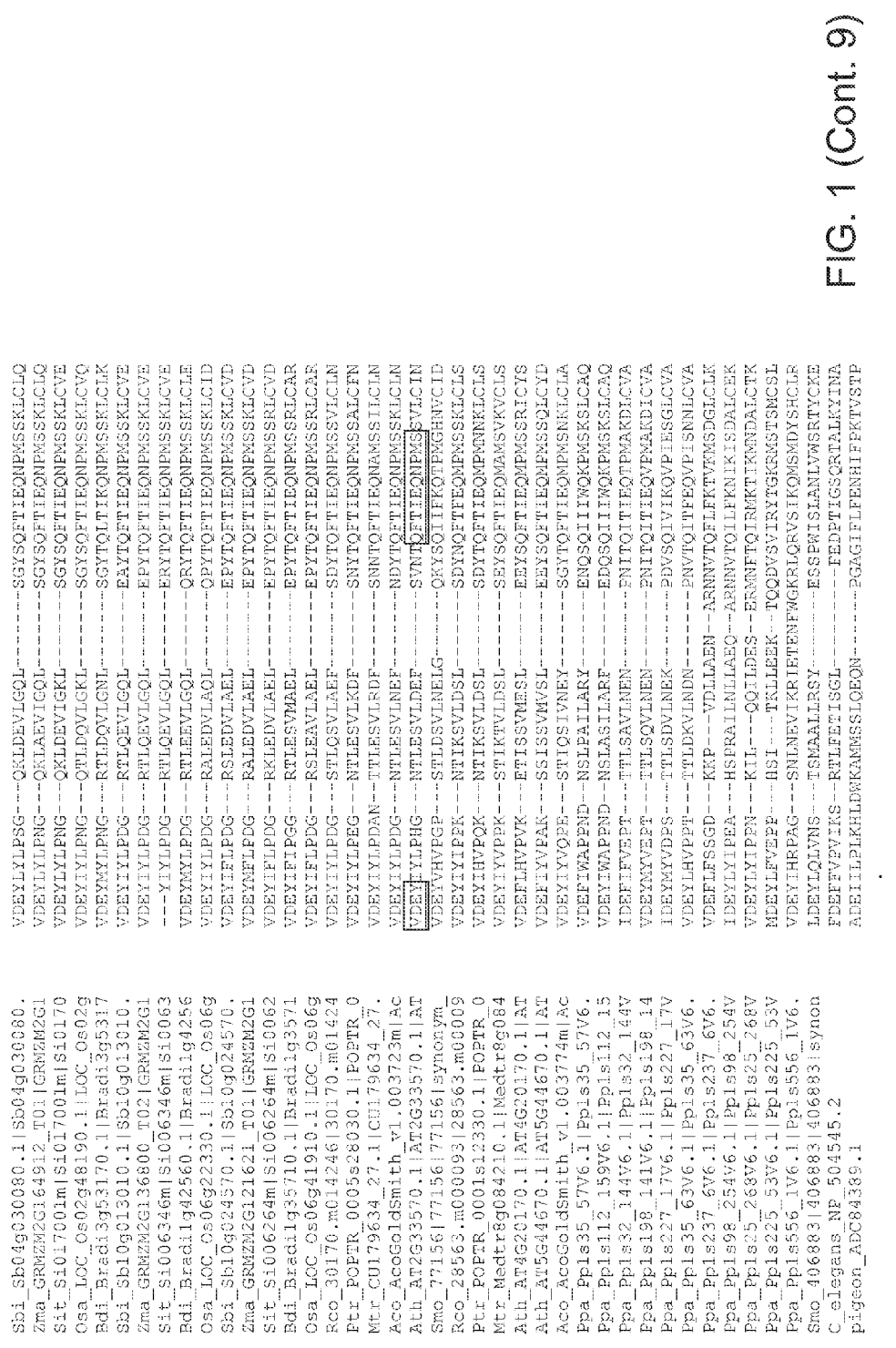
Figure 1:
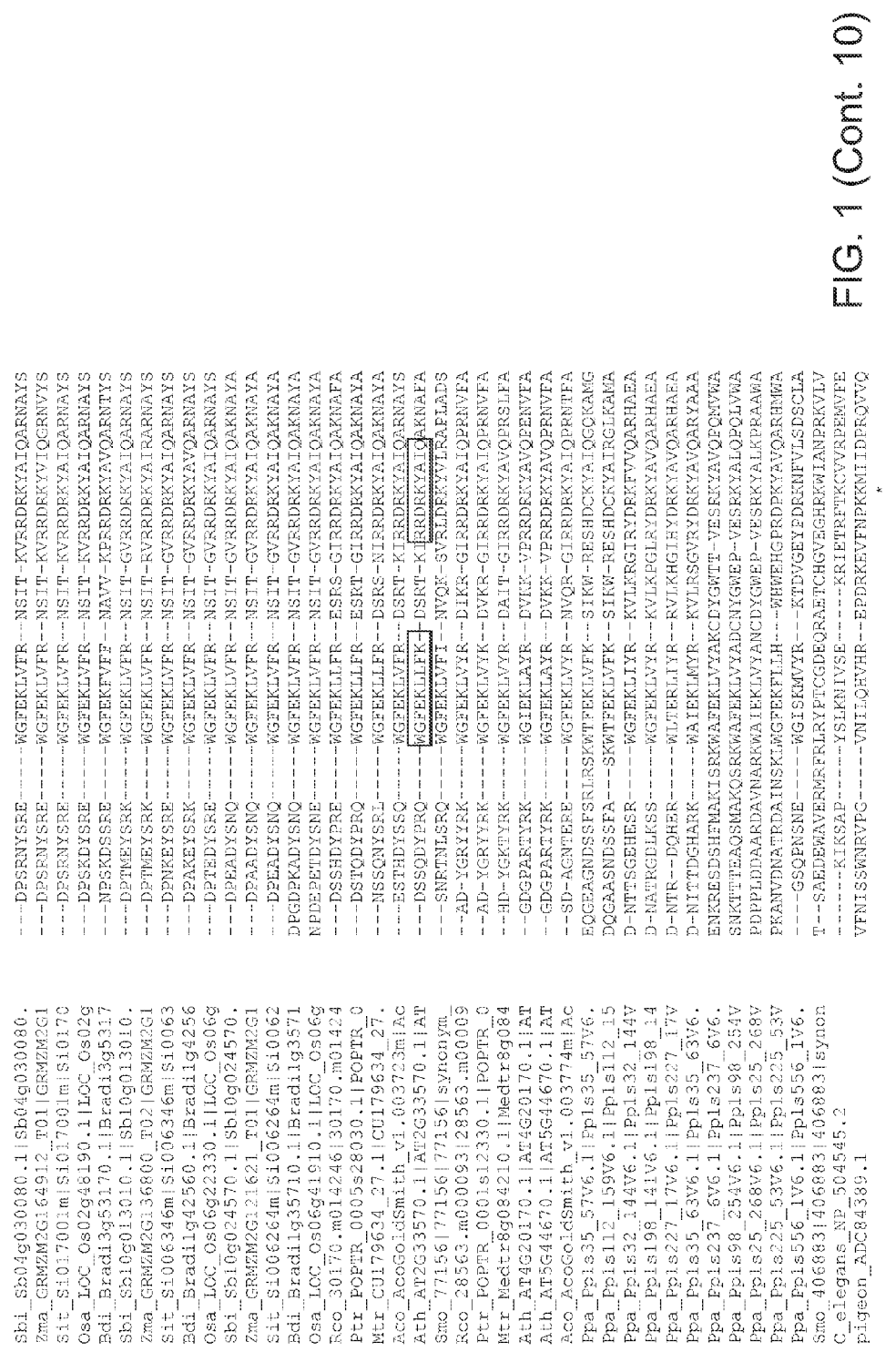
Figure 1:
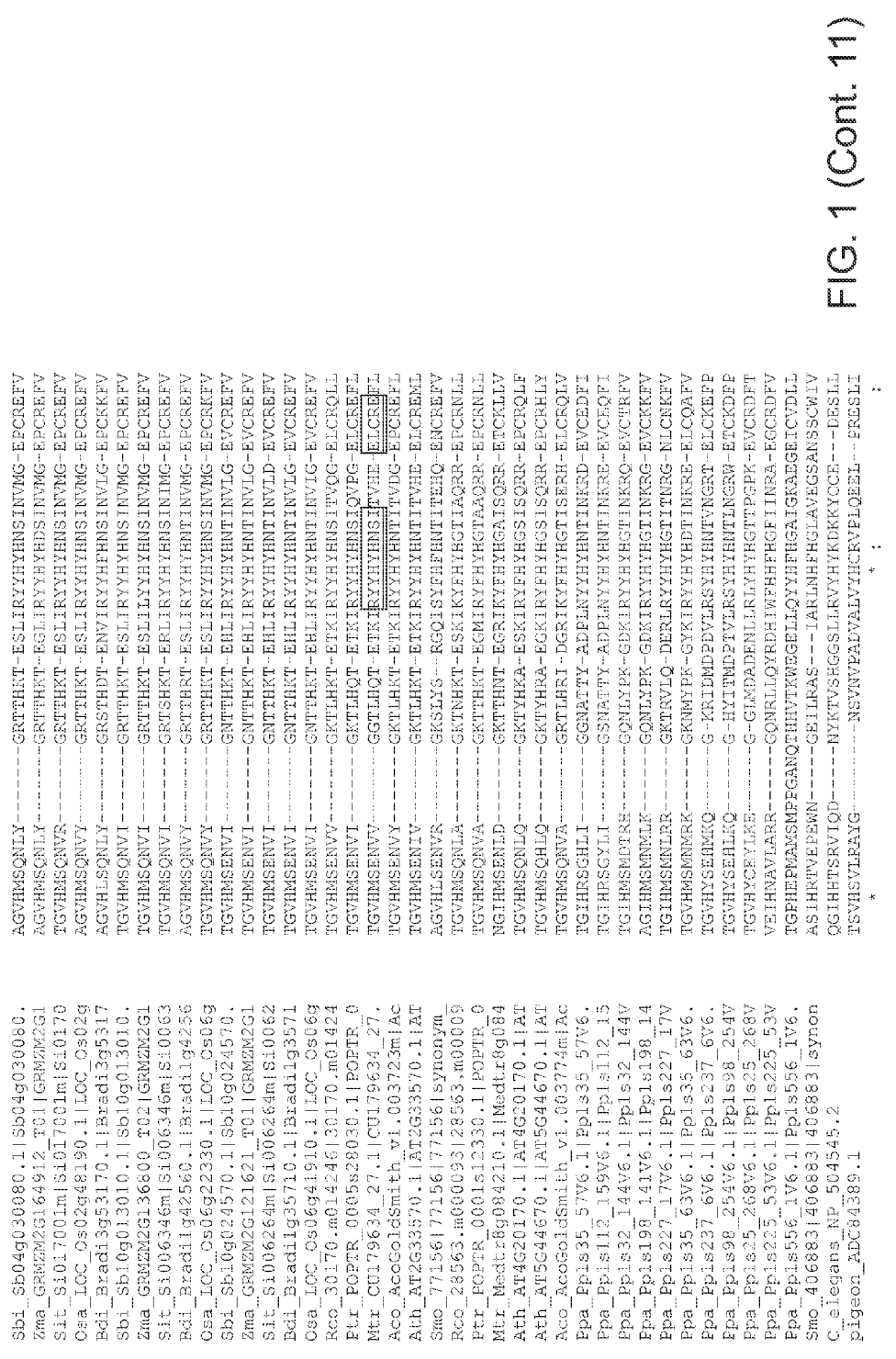
Figure 1:
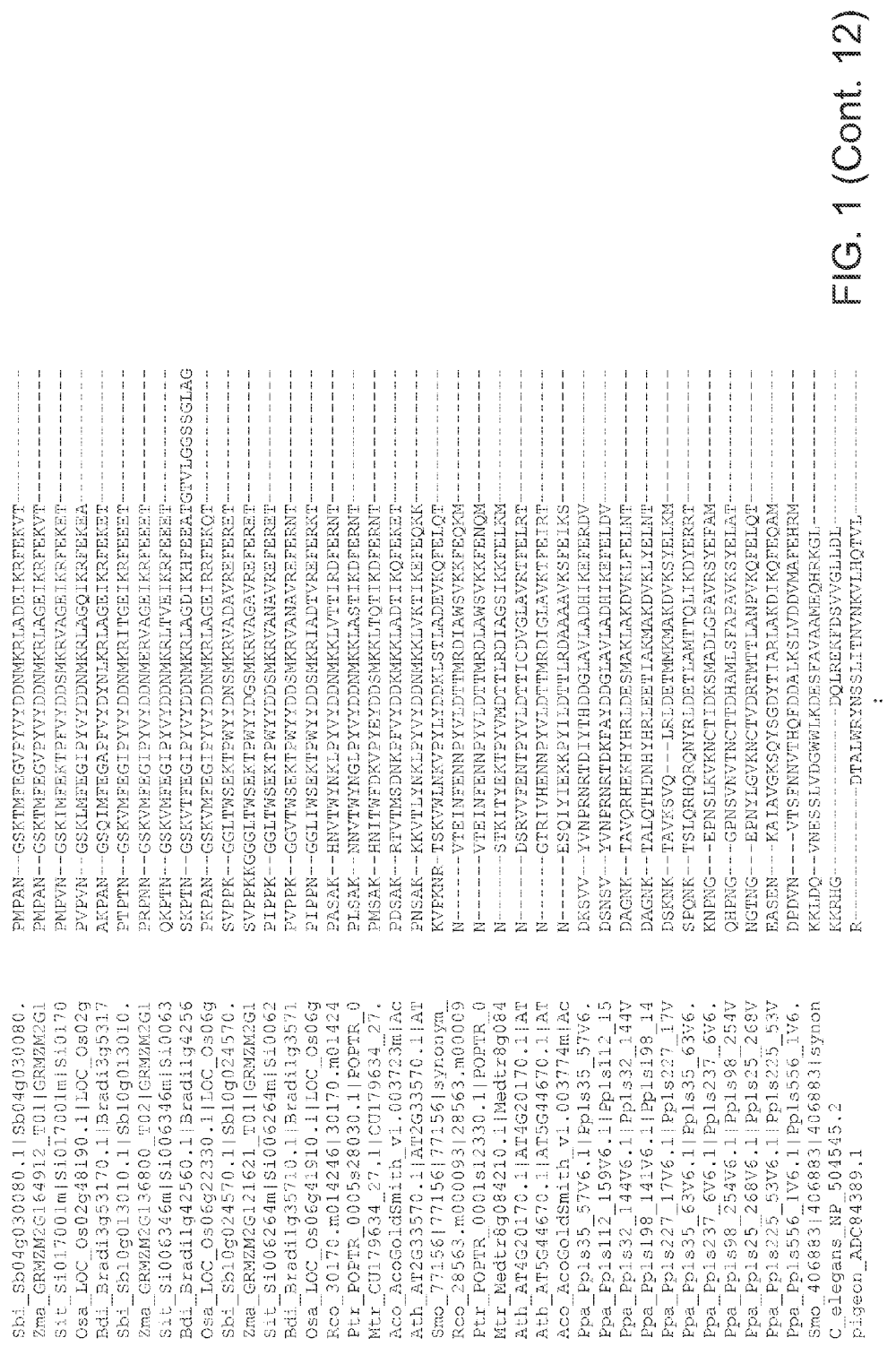
Figure 1:
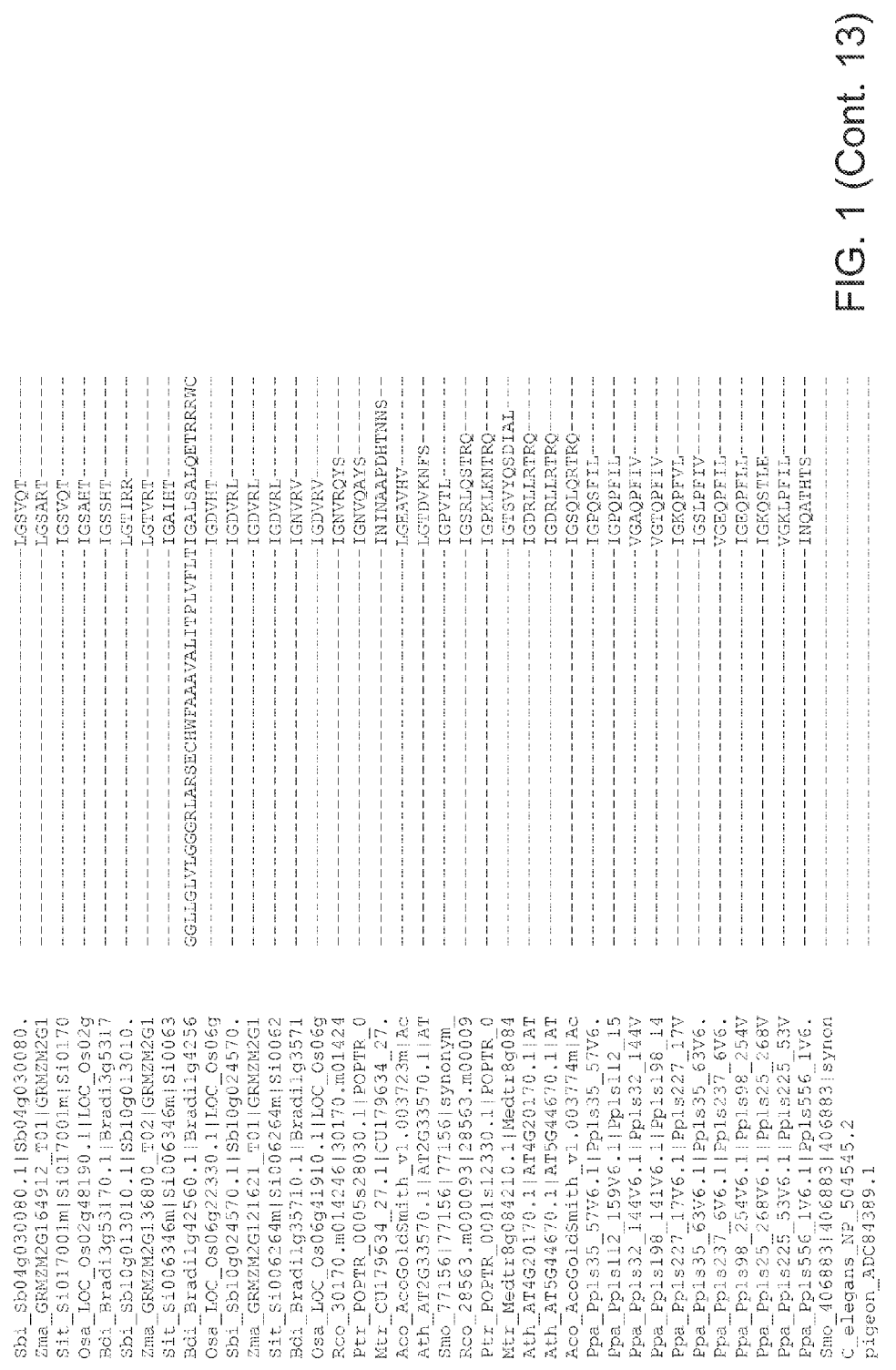
Figure 1:
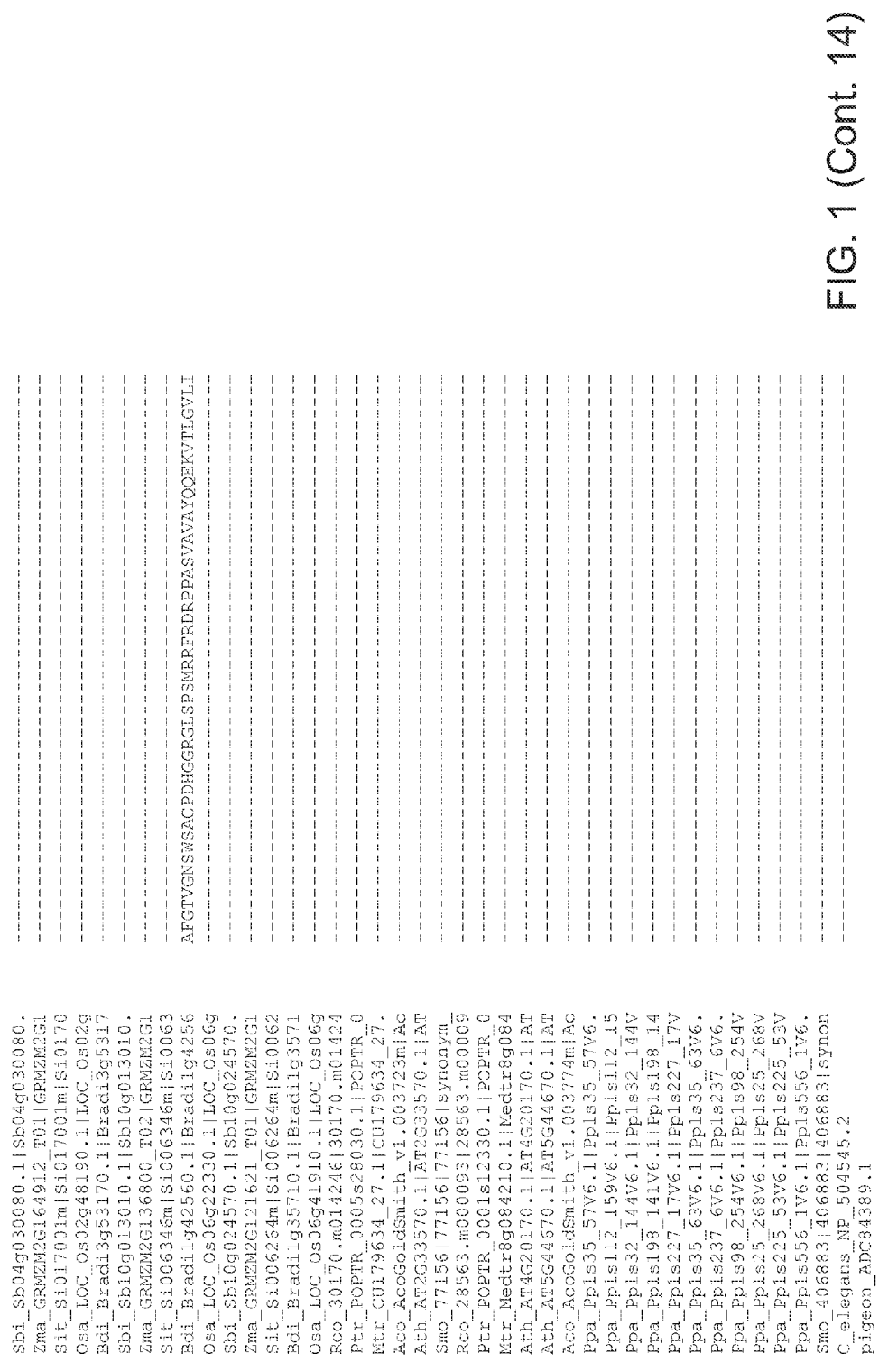
Figure 1:
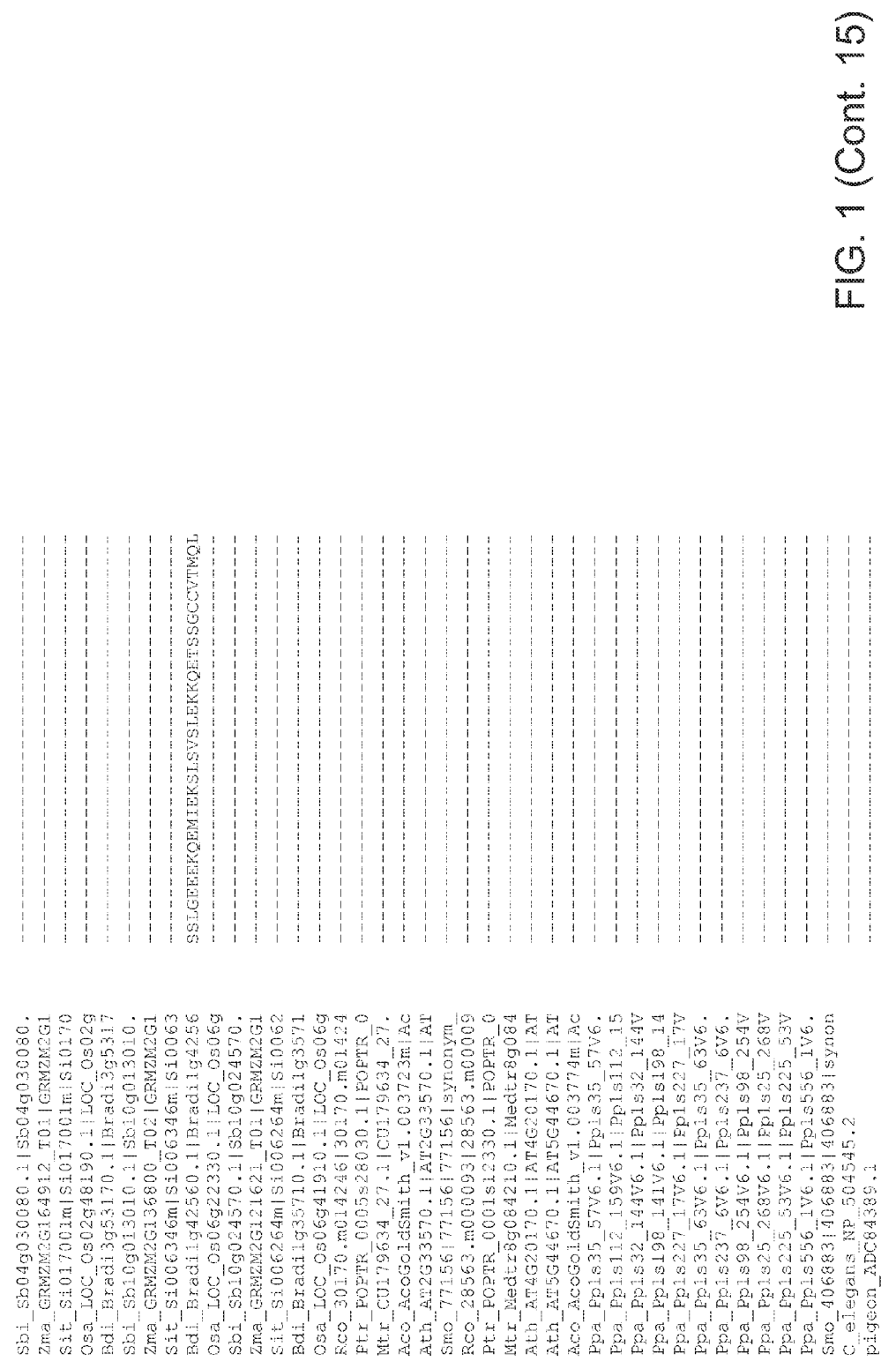

A comparison of GALS sequences is provided in FIG. 1. As shown in FIG. 1, there are highly conserved regions of the polypeptide sequences. For example, the sequence (F/Y/V)G(N/S/T)AAALFV(L/Q)MGAYRGGP (SEQ ID NO:46) (the corresponding sequence is shaded and underlined in SEQ ID NO:1 of FIG. 1) is highly conserved throughout diverse plant GALS sequences. Additional highly conserved sequences include SKPIHVYGKPWYKCEWISN (SEQ ID NO:47), KILPDWGYGRVYTVVVVNCTF (SEQ ID NO:48), GG(K JR)LI(L/V/I) (SEQ ID NO:49), Y(D/E)YLYCGSSL(Y/F)G (SEQ ID NO:50), REWMAYHAWFFG (SEQ ID NO:51), SHFVFHDAGG (SEQ ID NO:52), QNIRDQ (SEQ ID NO:53), GYYYNQFLIVND-CLHRYRYAANWTFFDVDEY (SEQ ID NO:54), FTIEQNPMS (SEQ ID NO:55), WGFEKLLFK (SEQ ID NO:56), RRDRKYAIQ (SEQ ID NO:57), RYYHYHNSI (SEQ ID NO:58), and ELCRE (SEQ ID NO:59) all of which are indicated in with reference to SEQ ID NO:1 shown in FIG. 1 by underlining and shading of SEQ ID NO:1. These conserved sequences are not strictly conserved 100% across the various plant protein sequences. One of skill can obtain a GALS variant by using the sequence alignments to identify residues within the conserved sequences that would be expected to retain GALS function as well as residues outside of the conserved regions that would be tolerant to substitution.

GALS activity can he assessed using any number of assays, including assays that evaluate transfer of galactose onto an acceptor. A convenient assay incubates an enzyme preparation in the presence of UDP-Gal and beta-1,4-galacto-oligosaccharides, e.g., beta-1,4-galactopentaose. The products consisting of the acceptor with addition of one or more galactose units can then be characterized by any number of methods. The simplest is to remove unincorporated UDP-Gal by ion exchange chromatography and analyze the product by liquid scintillation counting (provided that radiolabelled UDP-Gal was used). An alternative method is to use mass spectrometry, paper chromatography or thin layer chromatography. If a charged group is linked to the reducing end of the acceptor or product, it can also be analyzed by capillary electrophoresis or gel electrophoresis. If the charged group is also fluorescent it can be easily detected. A non-charged fluorescent labeled galacto-oligosaccharide has been used as acceptor in such assays where the products were separated by HPLC and detected by the fluorescent group (Ishii et al., Planta 219:310-318, 2004), Genetic modification of a plant to overexpress GALS is often performed in conjunction with modifying the plant to overexpress UDP-galactose epimerase (UGE) (EC 5.1.3.2). UDP-galactose epimerase nucleic acid and polypeptide sequences are well known in the art. Examples of UGE sequences that can be overexpressed are provided in U.S. Patent Application Publication Nos. 20030073828; 20070028332; and described by Barber et al. *J. Biol. Chem.* 281:17276-17285, 2006; and Kotake et al., *Biochem J.* 424:169-177, 2009; and Oomen et al. *Plant Science* 166: 1097-1104, 2004, each of which is incorporated by reference.

Isolation or generation GALS polynucleotide sequences (or UGE sequences) can be accomplished by a number of techniques. Cloning and expression of such technique will be addressed in the context of GALS genes. However, the same techniques can be used to isolate and express UGE family. In some embodiments, oligonucleotide probes based on the sequences disclosed here can be used to identify the desired polynucleotide in a cDNA or genomic DNA library from a desired plant species. Probes may be used to hybridize with genomic DNA or cDNA sequences to isolate homologous genes in the same or different plant species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying a GALS gene from plant cells such as moss or spikemoss, can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990).

GALS nucleic acid sequences for use in the invention includes genes and gene products identified and characterized by techniques such as hybridization and/or sequence analysis using exemplary nucleic acid sequences, e.g., SEQ ID NO:42, SEQ ID NO:43, or SEQ ID NO:44.

Preparation of Recombinant Vectors

To use isolated sequences in the above techniques, recombinant DNA vectors suitable for transformation of plant cells such as crop plant cells are prepared. Techniques for transformation are well known and described in the technical and scientific literature. For example, a DNA sequence encoding a GALS polypeptide (described in further detail below), can be combined with transcriptional and other regulatory sequences which will direct the transcription of the sequence from the gene in the intended cells, e.g., grass or other crop plant cells. In some embodiments. an expression vector that comprises an expression cassette that comprises the GALS gene further comprises a promoter operably linked to the GALS gene. In other embodiments, a promoter and/or other regulatory elements that direct transcription of the GALS gene are endogenous to the plant and an expression cassette comprising the GALS gene is introduced, e.g., by homologous recombination, such that the heterologous GALS gene is operably linked to an endogenous promoter and is expression driven by the endogenous promoter.

Regulatory sequences include promoters, which maybe either constitutive or inducible, or tissue-specific.

Tissue-Specific Promoters

In some embodiments, a plant promoter to direct expression of a GALS gene in a specific tissue is employed (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, cell walls, including e.g., roots or leaves. A variety of promoters specifically active in vegetative tissues, such as leaves, stems, roots and tubers are known. For example, promoters controlling patatin, the major storage protein of the potato tuber, can be used (see, e.g., Kim. *Plant Mol. Biol.* 26:603-615, 1994; Martin, *Plant J.* 11:53-62, 1997). The ORF13 promoter from *Agrobacterium rhizogenes* that exhibits high activity in roots can also be used (Hansen, *Mol. Gen. Genet.* 254:337-343, 1997). Other useful vegetative tissue-specific promoters include: the tarin promoter of the gene encoding a globulin from a major taro (*Colocasia esculenta* L. Schott) corm protein family, tarin (Bezerra, *Plant Mol. Biol.* 28:137-144, 1995); the curculin promoter active during taro corm development (de Castro, *Plant Cell* 4:1549-1559, 1992) and the promoter for the tobacco root-specific gene TobRB7, whose expression is localized to root meristem and immature central cylinder regions (Yamamoto, Plant Cell 3:371-382, 1991).

Leaf-specific promoters, such as the ribulose biphosphate carboxylase (RBCS) promoters can be used. For example, the tomato RBCS1, RBCS2. and RBCS3A genes are expressed in leaves and light-grown seedlings, only RBCS1 and RBCS2 are expressed in developing tomato fruits (Meier, *FEBS Lett.* 415:91-95, 1997). A ribulose bisphosphate carboxylase promoters expressed almost exclusively in mesophyll cells in leaf blades and leaf sheaths at high levels (e.g., Matsuoka., *Plant J.* 6:311-319, 1994), can be used. Another leaf-specific promoter is the light harvesting chlorophyll a/b binding protein gene promoter (see, e.g., Shiina, *Plant Physiol.* 115:477-483, 1997; Casal, *Plant Physiol.* 116:1533-1538, 1998). The *Arabidopsis thaliana* myb-related gene promoter (Atmyb5) (Li, et al., *FEBS's Lett.* 379:117-121 1996), is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize (e.g., Busk et at., *Plant J.* 11:1285-1295, 1997) can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, (e.g., Di Laurenzio, et al., *Cell* 86:423-433, 1996; and, Long, et al. Nature 379:66-69, 1996); can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, Plant Cell, 7:517-527, 1995). Also useful are kn1-related genes from maize and other species which show meristem-specific expression, (see, e.g., Granger, *Plant Mol. Biol.* 31:373-378, 1996; Kerstetter, *Plant Cell* 6:1877-1887, 1994; Hake, Philos. Trans. R. Soc. Lond. B. Biol. Sci. 350:45-51, 1995). For example, the *Arabidopsis thaliana* KNAT1 promoter (see, e.g., Lincoln, *Plant Cell* 6:1859-1876, 1994) can be used.

In some embodiments, the promoter is substantially identical to the native promoter of a promoter that drives expression of a gene involved in secondary wall deposition. Examples of such promoters are promoters from IRX1, IRX3, IRX5, IRX8, IRX9, IRX14, IRX7, TRX10, GAUT13, or GAUT14 genes. Specific expression in fiber cells can be accomplished by using a promoter such as the NST1 promoter and specific expression in vessels can be accomplished by using a promoter such as VND6 or VND7. (See, e.g., PCT/US2012/023182 for illustrative promoter sequences).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Constitutive Promoters

A promoter, or an active fragment thereof, can be employed which will direct expression of a nucleic acid encoding a fusion protein of the invention, in all or most transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless, *Arch. Virol.* 142:183-191, 1997); the 1'- or 2'-promoter derived from T-DNA of *Agrobacterium tumefaciens* (see, e.g., Mengiste supra (1997); O+Grady, Plant Mol. Biol. 29:99-108, 1995); the promoter of the tobacco mosaic virus; the promoter of Figwort mosaic virus (see, e.g., Maiti, *Transgenic Res.* 6:143-156, 1997); actin promoters, such as the *Arabidopsis* actin gene promoter (see, e.g., Huang, *Plant Mol. Biol.* 33:125-139, 1997); alcohol dehydrogenase (Adh) gene promoters (see, e.g., Millar, *Plant Mol. Biol.* 31:897-904, 1996); ACT11 from *Arabidopsis* (Huang et al., *Plant Mol. Biol.* 33:125-139, 1996), Cat3 from *Arabidopsis* (GenBank No. U43147, Zhong et al., *Mol. Gen. Genet.* 251:196-203, 1996), the gene encoding stearoyl-acyl carrier protein desaturase from *Brassica napus* (Genbank No. X74782, Solocombe et al., *Plant Physiol.* 104:1167-1176, 1994), GPc1 from maize (GenBank No. X15596, Martinez et al., *J. Mol. Biol.* 208:551-565, 1989), GPc2 from maize (GenBank No. U45855, Manjunath et al., *Plant Mol. Biol.* 33:97-112, 1997), other transcription initiation regions from various plant genes known to those of skill. See also Holtorf, "Comparison of different constitutive and inducible promoters for the overexpression of transgenes in *Arabidopsis thaliana,*" *Plant Mol. Biol.* 29:637-646, 1995).

Inducible Promoters

In some embodiments, a plant promoter may direct expression of the nucleic acids under the influence of changing environmental conditions or developmental conditions. Examples of environmental conditions that may effect transcription by inducible promoters include anaerobic conditions, elevated temperature, drought or other environmental stress, or the presence of light. Examples of developmental conditions that may effect transcription by inducible promoters include senescence and embryogenesis. Such promoters are referred to herein as "inducible" promoters. For example, the invention can incorporate drought-specific promoter such as the drought-inducible promoter of maize (Busk et al., *Plant J,* 11: 1285-95, 1997); or alternatively the cold, drought, and high salt inducible promoter from potato (Kirch *Plant Mol. Biol.* 33:897-909, 1997).

Suitable promoters responding to biotic or abiotic stress conditions include the pathogen inducible PRP1-gene promoter (Ward et al., *Plant. Mol. Biol.* 22:361-366, 1993), the heat inducible hsp80-promoter from tomato (U.S. Pat. No. 5,187,267), cold inducible alpha-amylase promoter from potato (PCT Publication No, WO 96/12814) or the wound-inducible pinII-promoter (European Patent No. 375091). For other examples of drought, cold, and salt-inducible promoters, such as the RD29A promoter, see, e.g., Yamaguchi-Shinozalei et al., *Mol. Gen. Genet.* 236:331-340. 1993 are also known.

Alternatively, plant promoters which are inducible upon exposure to plant hormones, such as auxins, may be used to express GALS genes. For example, the invention can use the auxin-response elements E1 promoter fragment (AuxREs) in the soybean (*Glycine max* L.) (Liu, *Plant Physiol.* 115: 397-407, 1997); the auxin-responsive *Arabidopsis* GST6 promoter (also responsive to salicylic acid and hydrogen peroxide) (Chen, Plant J. 10: 955-966, 1996); the auxin-inducible parC promoter from tobacco (Sakai, 37:906-913, 1996); a plant biotin response element (Streit, *Mol. Plant Microbe Interact.* 10:933-937, 1997); and, the promoter responsive to the stress hormone abscisic acid (Sheen, *Science* 274:1900-1902, 1996).

Plant promoters inducible upon exposure to chemicals reagents that may be applied to the plant, such as herbicides or antibiotics, are also useful for expressing a GALS gene in accordance with the invention. For example, the maize In2-2 promoter, activated by benzenesulfonamide herbicide safeners, can be used (De Veylder, *Plant Cell Physiol.* 38:568-577, 19997); application of different herbicide safeners induces distinct gene expression patterns, including expression in the root, hydathodes, and the shoot apical meristem. A GALS coding sequence can also be under the control of, e.g., a tetracycline-inducible promoter, such as described with transgenic tobacco plants containing the *Avena saliva* L. (oat) arginine decarboxylase gene (Masgrau, *Plant J.* 11:465-473, 1997); or, a salicylic acid-responsive element (Stange, *Plant J.* 11:1315-1324, 1997; Uknes et al., *Plant Cell* 5:159-169, 1993); Bi et al., *Plant J.* 8:235-245, 1995), Examples of useful inducible regulatory elements include copper-inducible regulatory elements (Mett et al., Proc, Natl. Acad. Sci. USA 90:4567-4571, 1993); Furst et al., *Cell* 55:705-717, 1988); tetracycline and chlor-tetracycline-inducible regulatory elements (Gatz et al., *Plant J.* 2:397-404, 1992); Röder et al., *Mol. Gen. Genet.* 243:32-38, 1994); Gatz, *Meth. Cell Biol,* 50:411-424, 1995); ecdysone inducible regulatory elements (Christopherson et al., *Proc. Natl. Acad. Sci. USA* 89:6314-6318, 1992; Kreutzweiser et al., *Ecotaxicol. Environ. Safety* 28:14-24, 1994); heat shock inducible regulatory elements (Takahashi et al., *Plant Physiol.* 99:383-390, 1992; Yabe et al., *Plant Physiol.* 35:1207-1219, 1994; Ueda et al., *Mol. Gen. Genet.* 250:533-539, 1996); and lac operon elements, which are used in combination with a constitutively expressed lac repressor to confer, for example, IPTG-inducible expression (Wilde et al., *EMBO J.* 11:1251-1259, 1992). An inducible regulatory element useful in the transgenic plants of the invention also can be, for example, a nitrate-inducible promoter derived from the spinach nitrite reductase gene (Back et al., Plant Mol. Biol. 17:9 (1991)) or, a light-inducible promoter, such as that associated with the small subunit of RuBP carboxy-lase or the LHCP gene families (Feinbaum et al., Mol. Gen. Genet. 226:449 (1991); Lam and Chua, Science 248:471 (1990)).

Expression Using a Positive Feed Back Loop

In further embodiments, a plant can be engineered to overexpress GALS using a positive feedback loop to express GALS in a desired tissue. In such an embodiment, a promoter for use in a GALS expression construct is responsive to a transcription factor that mediates expression in the desired tissue. The GALS expression construct is used in a genetically modified plant comprising an expression construct encoding a transcription factor where expression is also driven by a promoter that is responsive to the transcription factor. Examples of such expression systems are provided in PCT/US2012/023182.

In some embodiments in which a positive feed back loop is employed, the plant is genetically modified to express a transcription factor that regulates the production of secondary cell wall. Examples of such transcription factors include NST1, NST2, NST3, SND2, SND3, MYB103, MBY85, MYB46, MYB83, MYB58, and MYB63 (See, e.g., Mitsuda et al., *Plant Cell* 17:2993-3006 (2005); Mitsuda et al., *Plant Cell* 19:270-80 (2007); Ohashi-Ito et al., *Plant Cell* 22:3461-73 (2010); Zhong et al., *Plant Cell* 20:2763-82 (2008); Zhong et al., *Plant Cell* 19:2776-92 (2007); Ko et al., *Plant J.* 60:649-65 (2009); and McCarthy et al., *Plant Cell Physiol.* 50:1950-64 (2009)).

Illustrative examples of gene and protein sequences and/or accession numbers for NST1, NST2, NST3, SND2, SND3, MYB103, MBY85, MYB83, MYB58, and MYB63 are provided in PCT/US2012/023182.

In some embodiments, the polynucleotide encoding the transcription factor that regulates secondary cell wall production is operably linked to a promoter that is a downstream target of the transcription factor. Similarly, the GALS nucleic acid sequence is also linked to a promoter that is a downstream target of the transcription factor. The promoter may be the same promoter or different promoters. In such an embodiment, a promoter is suitable for use with the transcription factor that regulates secondary cell wall production if expression of the promoter is induced, directly or indirectly, by the transcription factor to be expressed, and if the promoter is expressed in the desired location, e.g., the stem of the plant.

In some embodiments, a native IRX1, IRX3, , IRX5, IRX8, IRX9, IRX14, IRX7, or IRX10, GAUT13, or GAUT14 promoter, or active variant thereof, is employed.

Additional Embodiments for Expressing GALS

In another embodiment, the GALS polynucleotide is expressed through a transposable element. This allows for constitutive, yet periodic and infrequent expression of the constitutively active polypeptide. The invention also provides for use of tissue-specific promoters derived from viruses including, e.g., the tobamovirus subgenomic promoter (Kumagai, *Proc. Natl. Acad., Sci. USA* 92:1679-1683, 1995); the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer, *Plant Mol. Biol.* 31:1129-1139, 1996).

A vector comprising GALS nucleic acid sequences will typically comprise a marker gene that confers a selectable phenotype on the cell to which it is introduced. Such markers are known. For example, the marker may encode antibiotic resistance, such as resistance to kanamycin, G418, bleomycin, hygromycin, and the like.

GALS nucleic acid sequences of the invention are expressed recombinantly in plant cells as described. As appreciated by one of skill in the art, expression constructs can be designed taking into account such properties as codon usage frequencies of the plant in which the GALS nucleic acid is to be expressed. Codon usage frequencies can be tabulated using known methods (see, e.g., Nakamura et al. *Nucl. Acids Res.* 28:292, 2000). Codon usage frequency tables are available in the art (e.g., from the Codon Usage Database at the internet site www.kazusa.or.jp/codon/.)

When two or more of GALS, UGE or transcription factors are expressed in combination, they can be expressed from individual promoters. In some embodiments. two or more proteins are expressed from a single promoter, e.g., by incorporating a 2A domain between the two coding sequences.

Additional sequence modifications may be made that are also known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence may also be modified to avoid predicted hairpin secondary mRNA structures.

Production of Transgenic Plants

As detailed herein, the present invention provides for transgenic plants comprising recombinant expression cassettes either for expressing heterologous GALS. it should be recognized that the term "transgenic plants" as used here encompasses the plant or plant cell in which the expression cassette is introduced as well as progeny of such plants or plant cells that contain the expression cassette, including the progeny that have the expression cassette stably integrated in a chromosome, Once an expression cassette comprising a polynucleotide encoding a GALS (or a polynucleotide sequence designed to suppress or inhibit GALS expression as described below) has been constructed, standard techniques may be used to introduce the polynucleotide into a plant in order to modify gene expression. See, e.g., protocols described in Ammirato et al. (1984) Handbook of Plant Cell Culture—Crop Species, Macmillan Publ. Co, Shimamoto et al. (1989) Nature 338: 274-276; Fromm et al. (1990) Bio/Technology 8:833-839; and Vasil et al. (1990) Bio/Technology 8:429-434.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Transformed plant cells derived by any of the above transformation techniques can be cultured to regenerate a whole plant that possesses the transformed genotype and thus the desired phenotype such as enhanced drought-resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts isolation and Culture, Handbook of Plant Cell Culture, pp. 124-176, MacMillan Publishing Company, New York, 1983; and Binding, Regeneration of Plants, Plant Protoplasts, pp. 21-73 CRC Press, Boca Raton, 1985. Regeneration can also be obtained from plant callus, explants, organs, or parts thereof. Such regeneration techniques are described generally, e.g., in Klee et al. *Ann. Rev. of Plant Phys.* 38:467-486, 1987.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The techniques described herein for obtaining and expressing GALS nucleic acid sequences in plant cells can also be employed to express nucleic acid sequences that encode UGE family members in order to modify plants to overexpress UGE proteins.

The expression constructs of the invention can be used to increase the galactan content of cell walls of essentially any plant. The plant may be a monocotyledonous plant or a dicotyledonous plant. In some embodiments of the invention, the plant is a green field plant. In some embodiments, the plant is a gymnosperm or conifer. Thus, the invention has use over a broad range of plants, including species from the genera *Asparagus, Atropa, Avena, Brassica, Cannabis, Citrus, Citrullus, Cameliria, Capsicum, Cucumis, Cucurbita, Daucus, Fragaria, Glycine, Gossypium, Hellman's, Heterocallis, Hordeum, Hyoscyamus, Lactuca, Linum, Lolium, Lycopersicon, Mattis, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum*, and, *Zea*. In some embodiments, the plant is corn, switchgrass, sorghum, miscanthus, sugarcane, poplar, pine, wheat, rice, soy, cotton, barley, turf grass, tobacco, potato, bamboo, rape, sugar beet, sunflower, willow, and eucalyptus. In further embodiments, the plant is reed canarygrass (*Phalaris arundinacea*), *Miscanthus x giganteus, Miscanthus* sp., sericea lespedeza (*Lespedeza cuneata*), ryegrass (*Lolium multiflorum, Lolium* sp.), timothy, Kochia (*Kochia scoparia*), forage soybeans, alfalfa, clover, sunn hemp, kenaf, bahiagrass, bermudagrass, dallisgrass, parigolagrass, big bluestem, indiarigrass, fescue (*Festuca* sp.), *Dactylis* sp., *Brachypodium distachyon*, smooth bromegrass, orchardgrass, or Kentucky bluegrass among others. In some embodiments, the plant is an ornamental plant. In some embodiment, the plant is a vegetable- or fruit-producing plant. In some embodiments, the plant is a plant that is suitable for generating biomass, including plants as noted above, e.g., *Arabidopsis*, poplar, eucalyptus, rice, corn, switchgrass, sorghum, millet, miscanthus, sugarcane, pine, alfalfa, wheat, soy, barley, turfgrass, tobacco, hemp, bamboo, rape, sunflower, willow, *Jatropha*, and *Brachypodium*.

In some embodiments, the plant into which the expression construct comprising a nucleic acid sequence that encodes GALS (or that is designed to inhibit expression of GALS) is introduced is the same species of plant from which the GALS sequence, and or the promoter driving expression of the GALS sequence, is obtained. In some embodiments, the plant into which the expression construct is introduced is a different species of plant compared to the species from which the GALS and/or promoter sequence was obtained.

Plants that overexpress GALS can be identified using any known assay, including analysis of RNA, protein, or galactan composition With respect to this aspect of the invention, the plants have enhanced galactan levels. Galactan levels can be determined directly or indirectly. For example, in some embodiments, galactan is assessed using an immunoassay employing an antibody that specifically binds beta-1,4, galactan to determine galactan levels. In some embodiments, GALS enzymatic activity can be directly measured in a plant by determining the activity of the enzyme to transfer galactose to an acceptor.

Modification of Plants to Decrease Galactan Production

In one aspect, the invention also provides a plant in which expression of GALS is inhibited, thereby resulting in reduced levels of galactan in the plant. In some embodiments, the plant is modified to have a level of GALS activity that is reduced throughout the entire plant. In some embodiments, the plant is modified to reduce GALS activity in a subset of cells or tissues of the plant. The genetic background of the plant can be modified according to any method known in the art, such as antisense, siRNA, microRNA, dsRNA, sense suppression, mutagenesis, or use of a dominant negative inhibition strategy. In some embodiments, the level of expression of the protein is reduced.

Gene Silencing Techniques

In some embodiments, expression of a GALS is inhibited by an antisense oligonucleotide. In antisense technology, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of a GALS-encoding sequence can be useful for producing a plant in which expression of GALS is inhibited. For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. In some embodiments, a sequence of at least, e.g., 20, 25, 30, 50, 100, 200, or more continuous nucleotides (up to mRNA full length) substantially identical to a GALS mRNA, or a complement thereof, can be used.

Catalytic RNA molecules or ribozymes can also be used to inhibit expression of a gene encoding a GALS polypeptide. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) Of with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature*, 334:585-591 (1988).

Another method by which expression of a gene encoding a GALS polypeptide can be inhibited is by sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes, see Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous GALS sequence intended to be repressed. This minimal identity will typically be greater than about 65%, but a higher identity can exert a more effective repression of expression of the endogenous sequences. In some embodiments, sequences with substantially greater identity are used, e.g., at least about 80%, at least about 95%, or 100% identity are used. As with antisense regulation, further discussed below, the effect can be designed and tested to apply to any other proteins within a similar family of genes exhibiting homology or substantial homology.

For sense suppression, the introduced sequence in the expression cassette needing less than absolute identity, also need not be full length, relative to either the primary transcription product or fully processed mRNA. Furthermore, the introduced sequence need not have the same intron or exon pattern, and identity of non-coding segments will be equally effective. In some embodiments, a sequence of the size ranges noted above for antisense regulation is used, i.e., 30-40, or at least about 20, 50, 100, 200, 500 or more nucleotides.

Endogenous gene expression may also be suppressed by means of RNA interference (RNAi) (and indeed co-suppression can be considered a type of RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (200)); Waterhouse et al., *Proc. Natl. Acad. Sci. USA* 95:13959-13964 (1998); Tabara et al. Science 282:430-431 (1998); Matthew, *Comp Funct Genom* 5: 240-244 (2004); Lu, et al., *Nucleic Acids Res.* 32 (21):e171 (2004)).

Thus, in some embodiments, inhibition of a gene encoding a GALS polypeptide is accomplished using RNAi techniques. For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting plants may then be screened for a phenotype associated with the target protein, for example, screening for an increase in the extractability of sugar from the plants as compared to wild-type plants, and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

Yet another way to suppress expression of an endogenous GALS gene is by recombinant expression of a microRNA that suppresses a target GALS. Artificial microRNAs are single-stranded RNAs (e.g., between 18-25-mers, generally 21-mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, U.S. Patent Publication No. 2008/0313773.

Another example of a method to reduce levels of GALS employs riboswitch techniques (see, e.g., U.S. Patent Application Publication Nos. U.S.20100286082, and U.S.20110245326).

Plants Having Mutant Backgrounds

In some embodiments, the level of expression of GALS is reduced by generating a plant that has a mutation in a gene encoding the GALS enzyme. One method for abolishing or decreasing the expression of a gene encoding GALS is by insertion mutagenesis using the T-DNA of *Agrobacterium tumefaciens*. After generating the insertion mutants, the mutants can be screened to identify those containing the insertion in the gene of interest. Mutants containing a single mutation event at the desired gene may be crossed to generate homozygous plants for the mutation (Koncz et al. (1992) Methods in *Arabidopsis* Research. World Scientific).

Alternatively, random mutagenesis approaches may be used to generate new alleles that will generate truncated or defective (non-functional or poorly active) enzymes or unstable RNA, or to disrupt or "knock-out" the expression of a gene encoding a GALS enzyme using either chemical or insertional mutagenesis or irradiation. For example, a procedure known as TILLING (see, e.g. Colbert et al., *Plant Physiol* 126:480-484, 2001; McCallum et al., *Nature Biotechnology* 18:455-457, 2000), may be used. In this method, mutations are induced in the seed of a plant of interest. The resulting plants are grown and self-fertilized, and the progeny are assessed, e.g., by PCR, to identify whether a mutated plant has a mutation in the gene of interest, or by evaluating whether the plant has reduced galactan content in a part of the plant that expressed the gene of interest.

An expression cassette comprising a polynucleotide encoding the GALS, or transcription factor regulating the production of secondary cell wall and operably linked to a promoter, as described herein, can be expressed in various kinds of plants. The plant may be a monocotyledonous plant or a dicotyledonous plant. In some embodiments of the invention, the plant is a green field plant. In some embodiments, the plant is a gymnosperm or conifer.

In some embodiments, the plant is a plant that s suitable for generating biomass. Examples of suitable plants include, but are not limited to, *Arabidopsis*, poplar, eucalyptus, rice, corn, switchgrass, sorghum, millet, miscanthus, sugarcane, pine, alfalfa, wheat, soy, barley, turfgrass, tobacco, hemp, bamboo, rape, sunflower, willow, *Jatropha*, and *Brachypodium*.

In some embodiments, the plant into which the expression cassette is introduced is the same species of plant as the promoter and/or as the polynucleotide encoding GALS or transcription factor (e.g., a vessel-specific promoter, GALS enzyme, and/or transcription factor from *Arabidopsis* is expressed in an *Arabidopsis* plant). In some embodiments, the plant into which the expression cassette is introduced is a different species of plant than the promoter and/or than the polynucleotide encoding GALS or transcription factor (e.g., a vessel-specific promoter, GALS enzyme, and/or transcription factor from *Arabidopsis* is expressed in a poplar plant). See, e.g., McCarthy et al., *Plant Cell Physiol*. 51:1084-90 (2010); and Zhong et al., *Plant Physiol*. 152:1044-55 (2010).

Methods of Using Plants Having Modified GALS Expression

Plants, parts of plants, or plant biomass material from plants having modified GALS expression can be used for a variety of purposes. In embodiments, in which GALS is overexpressed, the plants, parts of plants, or plant biomass material may be used in a conversion reaction to generate an increased amount of bioenergy as compared to wild-type plants. For example, the plants, parts of plants, or plant biomass material can be used in a saccharification reaction to generate an increased amount of soluble and fermentable sugar compared to wild-type plants. In some embodiments, the plants, parts of plants, or plant biomass material are used to increase biomass yield or simplify downstream processing for wood industries (such as paper, pulping, and construction) as compared to wild-type plants. In some embodiments, the plants, parts of plants, or plant biomass material are used to increase the quality of wood for construction purposes. In some embodiments the plants, or parts of plants are used to improve the quality of textile fiber or simplify the downstream processing for textile industry. In some embodiments the plants, or parts of plants, are used as a raw material for pectin production.

Methods of conversion, for example biomass gasification, are known in the art. Briefly, in gasification plants or plant biomass material (e.g., leaves and stems) are ground into small particles and enter the gasifier along with a controlled amount of air or oxygen and steam. The heat and pressure of the reaction break apart the chemical bonds of the biomass, forming syngas, which is subsequently cleaned to remove impurities such as sulfur, mercury, particulates, and trace materials. Syngas can then be converted to products such as ethanol or other biofuels.

Methods of enzymatic saccharification are also known in the art. Briefly, plants or plant biomass material (e.g., leaves and stems) are optionally pre-treated with hot water, dilute acid, alkali, or ionic liquid followed by enzymatic saccharification using a mixture of cellulases and hemicellulases and pectinases in buffer and incubation of the plants or plant biomass material with the enzymatic mixture. Following incubation, the yield of the saccharification reaction can be readily determined by measuring the amount of reducing sugar released, using a standard method for sugar detection, e.g. the dinitrosalicylic acid method well known to those skilled in the art. Plants engineered in accordance with the invention provide a higher sugar yield as compared to wild-type plants.

In some embodiments, plants in which GALS expression is inhibited that have decreased levels of galactan relative to wild type plants can be used in applications in which it may be desirable to increase the pectin yield and quality. For example in some embodiments, tubers may be genetically modified to inhibit expression of one or more GALS genes, thereby decreasing levels of galactan.

EXAMPLES

The following examples are provided to illustrate, but not limit the claimed invention.

1. Identification and Expression of GALS

Plant cell walls are predominantly composed of different polysaccharides, which can be grouped into cellulose, hemicelluloses and pectin. Pectin is a class of polysaccharide characterized by a high content of galacturonic acid residues and consists of two major types: homogalacturonan entirely composed of alpha-1,4-linked galacturonosyl residues, and rhamnogalacturonan I (RGI) composed of a backbone of alternating rhamnose and galacturonic acid residues with sidechains composed of arabinans and galactans. In example 1, we identified galactan synthase enzymes in plants. In this example, we investigated enzymes in glycosyltransferases family 92 (GT92), which has three members in *Arabidopsis*. Loss-of-function mutants in the corresponding genes showed a decreased content of beta-1,4-galactan. The plants did not have an obvious growth phenotype but pectin was more easily extracted from the cell walls of the mutants, and saccharification was improved. The GT92 enzymes were shown to be ubiquitously expressed and located in the Golgi apparatus. Heterologous expression of one of the proteins showed a high activity in transferring galactose residues from UDP-Gal onto beta-1,4-galactopentaose, confirming the identity of the GT92 enzyme as beta-1,4-galactan synthase.

Results

Glycosyltransferase Family GT92 Contains beta-1,4-galactosyltransferases

To identify candidate enzymes for beta-1,4-galactan synthase, we explored the CAZy database of carbohydrate active enzymes (www.cazy.org) (Cantarel et al., 2009). Glycosyltransferases in CAZy are divided into 91 families, 42 of which are represented in angiosperms. Many glycosyltransferases in a range of families have already been investigated in loss-of-function mutants, in many cases without clear indication of the role of the specific glycosyltransferases under study, and previous studies have not led to identification of good candidates for beta-1,4-galactan synthase. GT family 92 was added to CAZy recently with the identification of beta-1,4-galactosyltransferases in animals. The GT92 proteins are reported from pigeon, but not from chicken and not from mammals, where they catalyze the transfer of beta-1,4-linked galactose unto beta-1,4-linked galactose in N-glycan structures. In *C. elegans*, a member of GT92 has been shown to be a beta-1,4-galactosyltransferase that adds galactose onto core fucose in N-linked glycans. All plants that have had their genomes sequenced have members of GT92, but beta-1,4-galactose is not known from plant glycoproteins. Furthermore, GT92 genes have been identified in transcriptomic studies of tension wood, which is known to be rich in galactan. We investigated the role of GT92 proteins in *Arabidopsis*. In this species there are three members of GT92.

*Arabidopsis* Loss-of-function Mutants in GT92 Genes are Deficient in beta-1,4-galactan Mutants with T-DNA insertions in exons were identified for all three genes and required from the *Arabidopsis* Biological Resource Center (abro.osu.edu) and the European *Arabidopsis* Stock Centre (arabidopsis.info). Homozygous mutants were identified by PCR. Based on the results shown below, the enzymes were designated Galactan Synthase 1 (GALS1, At2g33570), GALS2 (At5g44670) and GALS3 (At4g20170).

Figure 2:
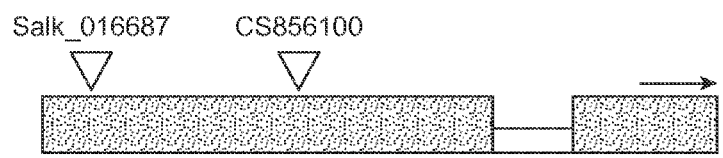
FIG. 2 provides a schematic illustration of inserts in mutant lines.
Figure 2:
Figure 2:
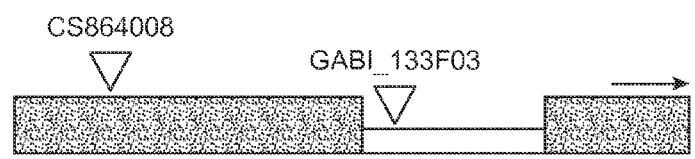
Figure 3:
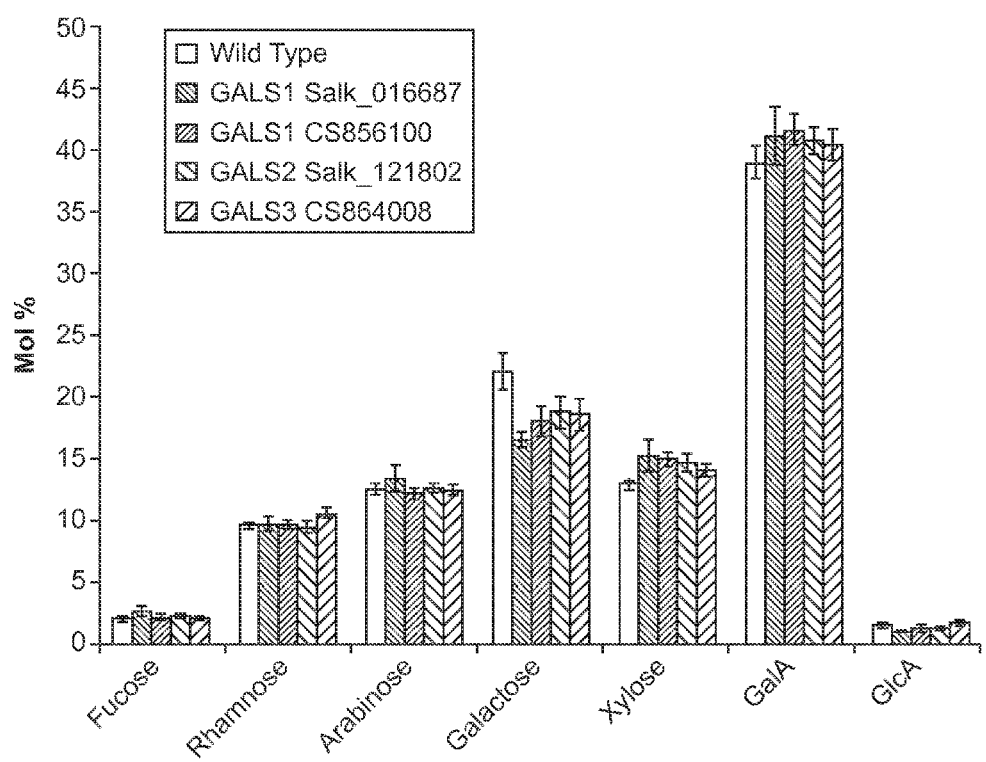
FIG. 3 provides illustrative data of the sugar composition in mutant and wildtype plants.
Figure 4:
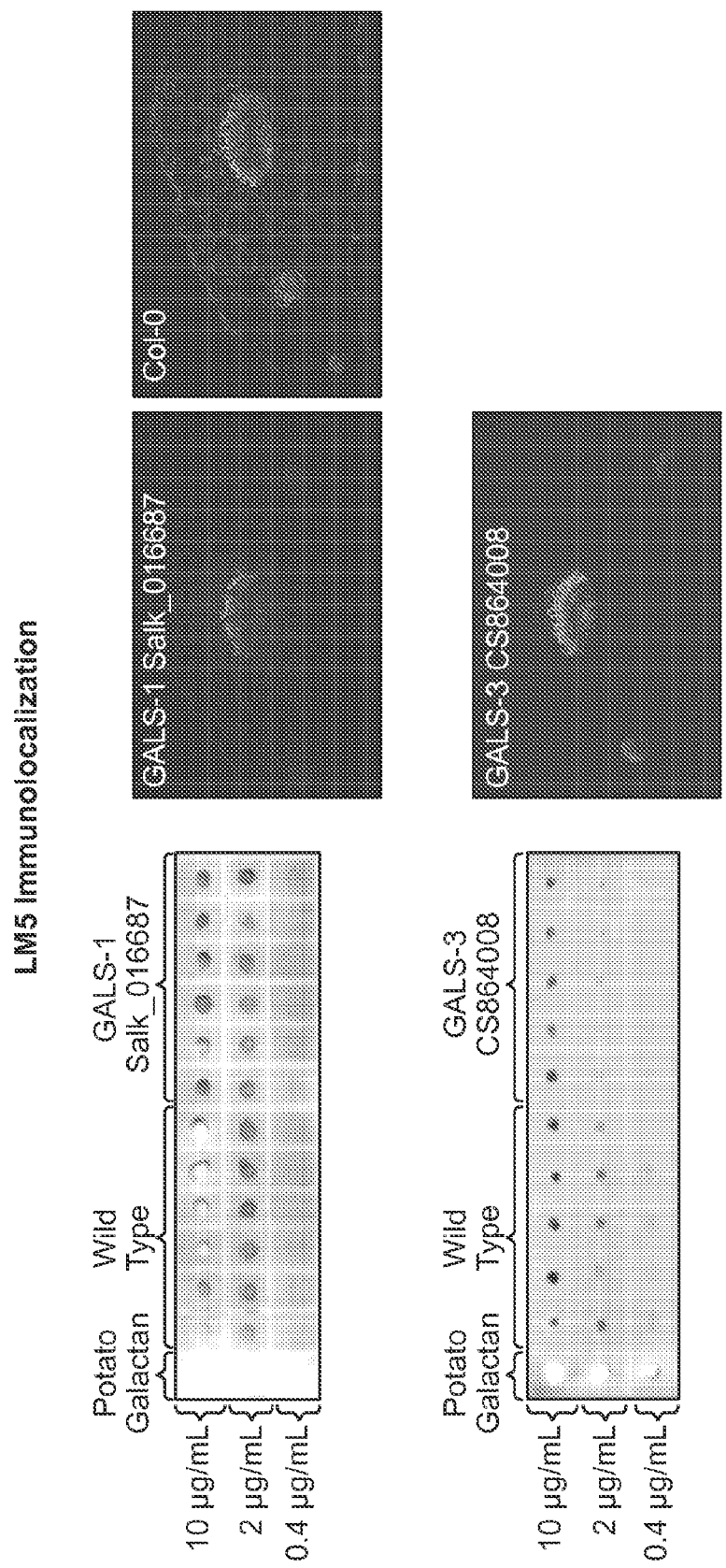
FIG. 4 provides illustrative data using an antibody specific for beta-1,4-galactan (LM5) that showed less galactan in the mutants compared to wildtype plants and that petioles had significantly less LM5 labeling in the mutants. Petioles were evaluated because GT92 enzymes are relatively highly expressed in this tissue.

None of the mutants showed any obvious growth or developmental alteration. Cell walls were prepared from leaves and stems and analyzed for sugar composition. Mutants in any of the three genes resulted in a decrease in total cell wall galactose content whereas no other sugar was changed (FIG. 2). Galactose is a component of several different cell wall components besides galactan. However, dot blots using the LM5 antibody, which is specific for beta-1,4-galactan, showed an effect in the mutants (FIG. 4), whereas an antibody recognizing arabinogalactan proteins did not show any difference in binding. The specific effect on beta-1,4-galactan was further shown by immunofluorescence microscopy of petioles, which had significantly less LM5 labeling in the mutants (FIG. 4). These data indicated that the GT92 enzymes were specifically involved in biosynthesis of beta-1,4-galactan.

GALS1, GALS2 and GALS3 are Golgi Localized Enzymes with Overlapping Expression Pattern The GALS proteins are predicted to be Type II membrane proteins targeted to the secretory pathway. The subcellular localization was investigated by heterologous expression of YFP fusion proteins in *Nicotiana benthamiana* and confocal laser scanning microscopy. This analysis showed that GALS proteins were targeted to Golgi vesicles, consistent with a role in pectin biosynthesis.

To investigate the expression of GALS in more detail we expressed the beta-glucuronidase gene under control of the native promoters of the three genes. The data confirmed that all three genes are expressed in several different tissues, but also showed some important differences in expression pattern.

GALS1 is a beta-1,4-galactosyltransferase

Figure 5:
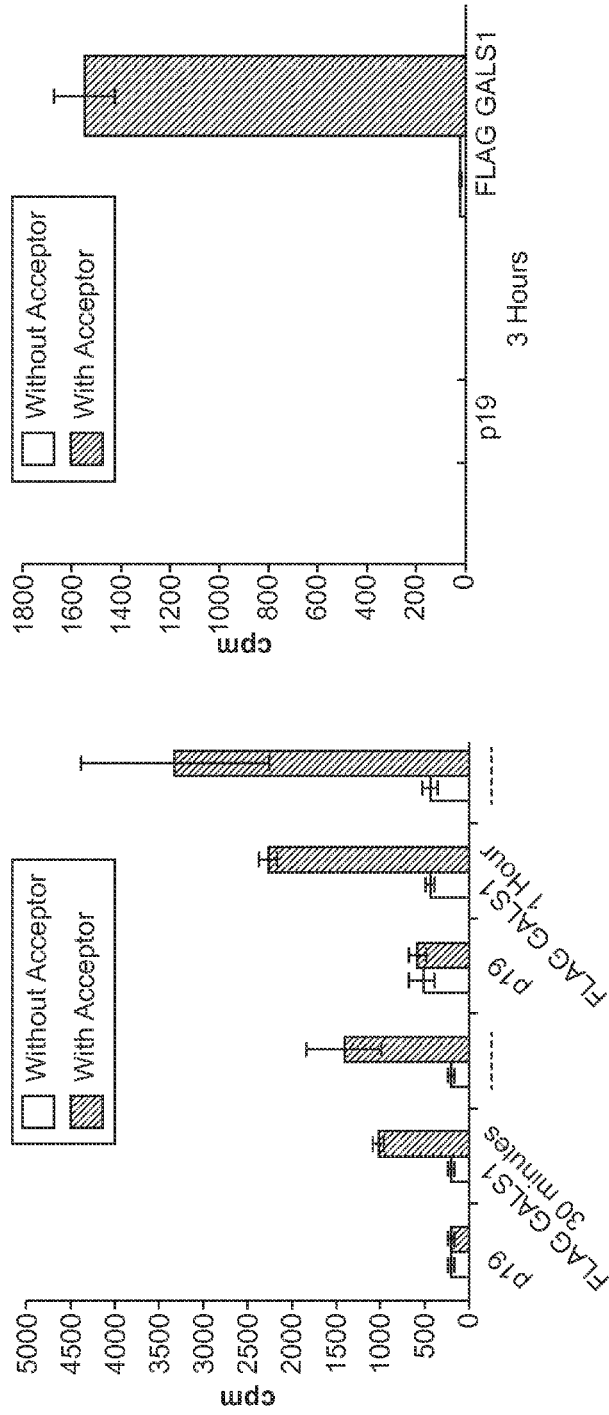
FIG. 5 shows illustrative data demonstrating galactosyltransferase activity. Activity assays were performed with a beta-1,4-galacto-pentaose acceptor and microsome (left panel) or affinity purified GALS1 protein (right panel).

Because the animal GT92 enzymes include beta-1,4-glactosyltransferases and the *Arabidopsis* mutants had specific deficiency in beta-1,4-galactan, the *Arabidopsis* GT92 enzymes were strong candidates for beta-1,4-galactan synthase. To further investigate this, the GALS1 protein was heterologously expressed in *N. benthamiana* as fusion protein with N-terminal FLAG or YFP tags. Galactan synthase assays using microsomal proteins and endogenous acceptors showed a very high activity. The identity of the product as beta-1,4-galactan was confirmed by digestion with beta-1,4-galactanase. To further characterize the galactosyltransferase activity we chemically synthesized beta-1,4-galactopentaose. The purity and identity of the beta-1,4-galactopentaose were confirmed by NMR (data not shown). After solubilization of microsomal membranes with Triton X-100 and incubation in the presence of the acceptor, the unincorporated UDP-Galactose was removed by anion exchange chromatography. The results showed a highly significant activity of transfer of galactose onto the acceptor with microsomes from plants expressing GALS1 (FIG. 5). The galactan synthase activity was high, but not very stable as seen from the comparison of 20 min and 1 hr incubation times.

While the data using microsomal protein strongly indicated that GALS1 was indeed beta-1,4-galactan synthase, it must always be considered that microsomes contain many proteins, including endogenous galactan synthase, and that the expression of a heterologous protein could alter the background of endogenous enzyme activities. This is not normally a problem for this type of assay, but must nevertheless be considered. We therefore affinity purified the FLAG-GALS1 fusion protein. The purified protein retained acceptor dependent activity, whereas the control reactions (mock purified protein from p19 expressing microsomes) had no detectable activity (FIG. 5).

Evaluation of GALS1 overexpressors demonstrated that the plants have 250% galactose in the cell wall compared to the control (data not shown).

Discussion

Pectin synthesis requires many different proteins for it synthesis and identifying these proteins has been very challenging. Only one enzyme—GAUT1—has had its activity unambiguously shown previously (Sterling et al., 2006). The XGD1 protein appears to add xylose to the backbone of homogalaturonan, but the activity was only shown with crude membrane preparations and not with isolated protein (Jensen et al., 2008). Here we provide clear biochemical evidence that glycosyltransferases of family GT92 in plants are beta-1,4-galactan synthases. The GALS1 enzyme showed a high activity with galactooligosaccharide acceptors and is hence capable of elongating beta-1,4-galactans. It is not clear if the same enzymes will add the first galactose residue onto the RGI backbone, but we find that unlikely due to the very different properties of the acceptor polysaccharide. Most likely one or two as yet unidentified galactosyltransferases are required to initiate the beta-1,4-galactan sidechains.

GT92 proteins are encoded in the genomes of all plants that have been investigated and are found in a limited range of animal species. They are not found in fungi, nor in green algae such as *Chlamydomonas reinhardtii*, but they are reported in apicomplexan of the *Cryptosporidium* genus. In animals the proteins are known to add beta-1,4-galactose to various NT-glycans, but this particular decoration is not well conserved and the phylogeny indicates that GT92 members have been lost in many taxonomic groups. In plants, the proteins are also beta-1,4-galactosyltransferases but have evolved specifically to synthesize pectic beta-1,4-galactans. The GT92 proteins contain Domain of Unknown Function 23 (DUF23), which is also found in a few bacteria. However, these bacterial proteins are quite divergent form the eukaryotic proteins and none of them have been characterized.

The three *Arabidopsis* GALS show overlapping but not identical expression. This explains why biochemical phenotypes could be observed for mutants in all three genes while all the mutants retained significant amounts of residual galactan. Mutants with combinations of two or three gene mutations can be generated to observe larger reductions in galactan. The mutants did not show any obvious phenotype on growth.

2. Overexpression of Galactan Synthase and Epimerase Increases Galactan Accumulation in Plants Overexpression of galactan synthase (GALS1 and homologs of this) led to increased galactan accumulation in plants. This example provides illustrative data showing that even higher accumulation can be achieved by coexpressing galactan synthase and an enzyme that produces the substrate of galactan synthase, i.e. UDP-glucose 4-epimerase (UGE).

Plants have different isoforms of UGE, which may differ in substrate specificity (some also convert UDP-xylose) and in specificity for certain polysaccharide products. For example, the *Arabidopsis thaliana* genome encodes five isoforms of UGE. These belong to a larger family of epimerases that also include UDP-glucuronic acid epimerases and UDP-xylose epimerases. The sequence of *Arabidopsis* UGE2 (see, e.g., Kotake et al., Biochem. J. 2009, supra) is provided as SEQ ID NO:45. Similar, although not necessarily identical, results with respect to further increasing galactan accumulation can be expected with different isoforms of UGE, e.g. UGE1, UGE2, UGE3, UGE4 and UGE5 from *Arabidopsis thaliana*. UGE2 was chosen for this example because it has low activity with UDP-xylose and because it has previously been implicated in pectin biosynthesis (whereas, e.g. UGE4 which has been implicated in arabinogalactan and xyloglucan biosynthesis).

Since an optimal biofuel feedstock would contain less xylose (pentose) and less lignin (recalcitrant), it would be desirable to generate a plant where hexoses, such as galactan, replace the xylans. Plants with a decrease in xylan have been engineered by expressing xylan GTs under control of vessel-specific promoters in xylan deficient mutants (see, e.g., Petersen et al., 2012). Similarly, plants with reduced lignin levels have been engineered by replacing the promoter of a key lignin gene (C4H) with a vessel-specific promoter (Yang et al., 2012). These low-lignin plants additionally contain an artificial positive feedback loop, with the NST1 transcription factor under control of the fiber-specific pIRX8 promoter, which it induces. This positive feedback loop results in plants with enhanced polysaccharide deposition in stems. An approach to add galactan to fibers cells of plants was therefore employed in this example where AtUGE2 was expressed in combination with the mentioned positive feedback loop, under control of the fiber-specific pIRX5 promoter.

Thus, two different strategies were employed to increase galactan (and thereby hexose) levels beyond what could be achieved by overexpression of GALS1 alone: Simultaneous overexpression of a UGE with GalS1, and tissue-specific expression of a UGE combined with a positive feedback loop for increased polysaccharide deposition.

Cloning Strategy—Construction of Transformation Vectors

Arabidopsis thaliana UGE2 was overexpressed in A. thaliana. In order to track the expression of the transgenic protein, constructs were designed to contain an N-terminal FLAG-tag or an N-terminal GFP-tag as well as the N-terminal FLAG-tag. The FLAG-tag was introduced by a PCR reaction using overlapping primers, while the GFP tag is part of the vector pMDC43. Both vectors pMDC32 and pMDC43 contain two consecutive copies of the Cauliflower Mosaic Virus 35S promoter. An empty vector control was generated by inserting a non-coding 15 bp sequence in the pMDC32 vector. Finally, a construct for fiber-specific expression of AtUGE2 was created with the pIRX5 promoter. IRX5 is a component of the cellulose synthase complex, and thus expression under its promoter leads to secondary cell wall expression (Taylor, 2003). The construct was designed so that after the promoter is the coding sequence of the transcription factor NAC Secondary Wall Thickening Promoting Factor 1 (NST1), followed by the autoproteolytic peptide 2A (Halpin et al., 1999), and then AtUGE2. NST1 is an important factor for activation of secondary wall biosynthesis including the deposition of cellulose in the interfascicular fibers, and affects several cellulose synthesis related genes, including inducing pIRX5. Therefore, by expressing this construct, a positive feedback loop is created, where expression of NST1 leads to an increased expression of the secondary cell wall synthesizing genes including pIR5X, which in turn leads to higher NST1 expression and as a result increased cell wall deposition.

All of the 35S constructs were transformed into Col-0 plants as controls. The 35S promoter FLAG-tagged AtUGE2 was also transformed in GalS1-overexpressing transformants in a Col-0 background. Likewise, the IRX5 promoter construct was transformed into GalS1 overexpressors. The GalS1 overexpressing lines containing BASTA resistance and YFP tagged GalS1 are described in Liwanag et al. (2012).

Monosaccharide Composition

The monosaccharide composition of the cell wall was determined by high-performance anion exchange chromatography (HPAEC) as described (Harholt et al., 2006), Destarched, TFA-hydrolyzed, Alcohol Insoluble (AIR) samples were run on an Ion Chromatography System 3000 (Dionex) using a CarboPac PA20 anion exchange column (Dionex) and gold electrode to determine the monosaccharide composition. Sugar standard solutions of 5, 10, 25, 50, 100, 150 and 200 µM of glucose, fucose rhamnose, arabinose, galactose, xylose, galacturonic acid and glucuronic acid (Sigma-Aldrich) were run as references. A NaOH gradient program from 10 mM to 45 mM NaOH was used to elute the sugars.

Results

Transformants were selected on plates with the appropriate antibiotic and transferred to soil. Among several recovered transformants, plants with high expression of the transgene were identified by RT-PCR. The selected plants were grown to maturity and the seeds harvested for analysis of cell wall composition in the subsequent plant generation.

Figure 6:
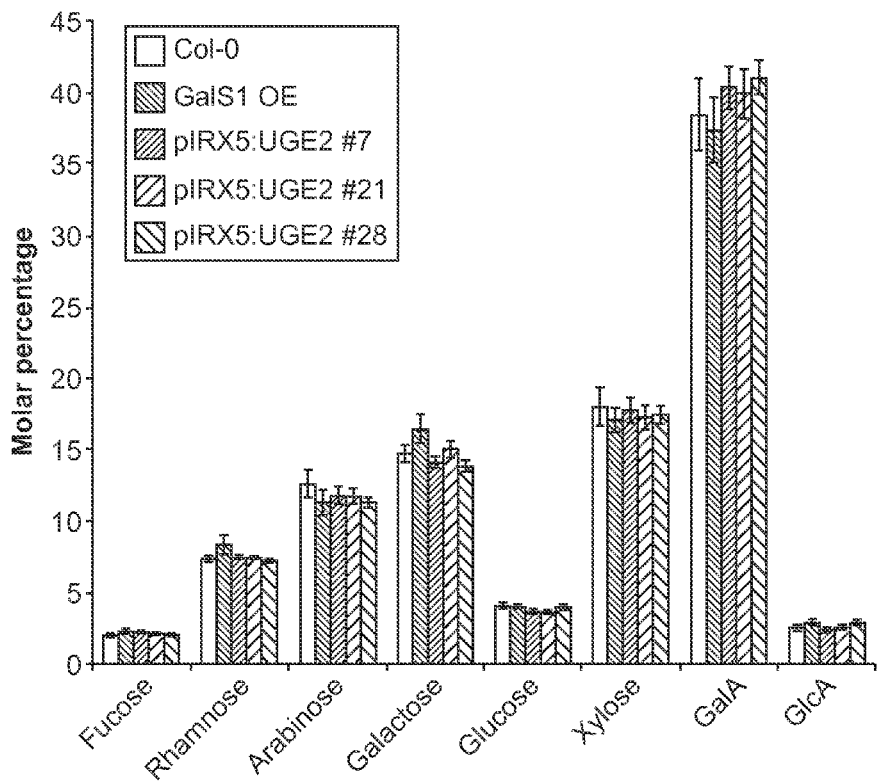
FIG. 6 provides illustrative data showing monosaccharide composition of leaf cell wall of plants overexpressing GalS1 or expressing NST1-2A-AtUGE2 under the fiber specific pIRX5 promoter in a Col-0 background. '2A' is a sequence from foot-and-mouth-disease virus that can be used to express multiple proteins from the same ORF. Sugar levels are described as molar percentage, ±SE (n=6). From left to right for each sugar, the bars are: Col-0, GalS1 OE, pIRX5: UGE2#7; pIRX5: UGE2#21, and pIRX5: UGE2#25

The cell walls of control plants expressing only UGE2 under the 35S promoter or the pIRX:NST1-2A-UGE2 construct were analyzed and compared to wild-type plants and GALS1 overexpressor plants. Only GALS1 overexpressing plants showed an increase in cell wall galactose (FIG. 6). Thus, under these conditions, expression of UGE2 NST1-2A-UGE2 alone did not result in increased galactan deposition in leaves.

When leaves were analyzed from plants that coexpressed GALS1 and UGE2, no increase was observed above that achieved with GALS1 alone (FIG. 7). However, leaves from plants coexpressing GALS1 and the NST1-2A-UGE2 construct had significantly higher galactose content in the cell walls over what was observed with GALS1 alone.

The pIRX5 promoter is not very active in leaves, and we therefore investigated cell walls of stems, which is also more relevant for biofuel and biorefinery applications. The results (FIG. 8) showed that coexpression of both UGE2 and GALS1 and of NST1-2A-UGE2 and GALS1 lead to increased cell galactose compared to expression of GALS1 alone. The plants responded by incorporating relatively less xylose in the cell walls. To better see the change in cell wall monosaccharides besides xylose, the data was also shown without xylose (FIG. 9). Clearly, the coexpression increased the galactose content substantially over that achieved with GALS1 overexpression alone. GALS1 overexpression alone with the 35S promoter does not lead to significant increase in galactose in stem cell walls. The figures also show that overexpression of the pIRX5:NST1-2A-UGE2 construct alone did not lead to increased galactose in stems.

The GALS1 gene in these experiments was expressed with the 35S promoter. For a higher expression in fiber cells and improved galactan accumulation in this cell type, the GALS1 gene or a homologous GALS gene is expressed under a promoter with high activity in fiber cells, e.g. pIRX8, pIRX5, or other as described in Loque D, Scheller H V (2012) Spatially modified gene expression in plants. PCT/US2012/023182. The GALS gene is expressed under a separate promoter distinct from the NST1-2A-UGE2 sequence or in one construct such as pIRX5:GALS1-2A-NST1-2A-UGE2 where all three open reading frames are transcribed from the same promoter.

Citations for References Cited by Author, Date

Cantarel B L, Coutinho P M, Rancurel C, Bernard T, Lombard V, Henrissat B (2009) The Carbohydrate-Active EnZymes database (CAZy): an expert resource for Glycogenomics. Nucleic Acids Res 37: D233-238

Harholt J, Jensen J K, Sorensen S O, Orfila C, Pauly M, Scheller H (2006) ARABINAN DEFICIENT 1 is a putative arabinosyltransferase involved in biosynthesis of pectic arabinan in Arabidopsis, Plant Physiol 140: 49-58

Harholt J, Jensen J K, Verhertbruggen Y, Sogaard C, Bernard S, Nafisi M, Poulsen C P, Geshi N, Sakuragi Y, Driouich A, Knox J P, Scheller H V (2012) ARAD proteins associated with pectic Arabinan biosynthesis form complexes when transiently overexpressed in planta. Planta Harholt J, Suttangkakul A, Vibe Scheller H (2010) Biosynthesis of pectin. Plant Physiol 153: 384-395

Jensen J K, Sorensen S O, Harholt J, Cieshi N, Sakuragi Y, Moller I, Zandleven J, Bernal A J, Jensen N B, Sorensen C, Pauly M, Beldman G, Willats W G, Scheller H V (2008) Identification of a xylogalacturonan xylosyltransferase involved in pectin biosynthesis in *Arabidopsis*. Plant Cell 20: 1289-1302

Mohnen D (2008) Pectin structure and biosynthesis. Curr Opin Plant Biol 11: 266-277

Sterling J D, Atmodjo M A, Inwood S E, Kumar Kolli V S, Quigley H F, Hahn M G, Mohnen D (2006) Functional identification of an *Arabidopsis* pectin biosynthetic homogalacturonan galacturonosyltransferase Proc Natl Acad Sci USA 103: 5236-5241

Kotake, T., Takata, R., Verma, R., Takaba, M., Yamaguchi, D., Orita, T., Kaneko, S., Matsuoka, K., Koyama, T., Reiter, W. D., Tsumuraya, Y. (2009). Bifunctional cytosol UDP-glucose 4-epimerases catalyse the interconversion between UDP-D-xylose and UDP-L-arabinose in plants. Biochemical Journal, 424, 169-177.

Petersen, P. D., Lau, J., Ebert, B., Yang, F., Verhertbruggen, Y., Kim, J. S., Varanasi, P., Suttangkakul, A., Auer, M., Loque, D., Scheller, H. V. (2012). Engineering of plants with improved properties as biofuels feedstocks by vessel-specific complementation of xylan biosynthesis mutants. Biotechnology for Biofuels, 5 (84).

Taylor, N. G. (2008). Cellulose biosynthesis and deposition in higher plants. New Phytologist, 178 (2), 239-252.

Yang, F., Mitra, P., Zhang, L., Prak, L., Verhertbruggen, Y., Kim, J., Sun, L., Zheng, K., Tang, K., Auer, M, Scheller, H. V., Loqué, D. (2012). Engineering secondary cell wall deposition in plants. Plant Biotechnology Journal.

Halpin, C. et al. (1999) Self-processing 2A-polyproteins—a system for co-ordinate expression of multiple proteins in transgenic plants. The Plant Journal 17, 453-459

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession numbers, and patent applications cited herein are hereby incorporated by reference in their entirety for all purposes.

Illustrative Sequences

GALS1 (*ARABIDOPSIS THALIANA*_ATG2G33570)
ACCESSION NUMBER: NP_565768.1 GENE ID: 817922
SEQ ID NO: 1
MRKEVLPPVLSTTTVCFEKKPIIATLLALSLVMIVWNLPPYYHNLISTA
RPCSAVTTTTTTLLSSSNFTSAENFTTSLSTTTAAASQKYDSTPSDPN
KRVFQPFGNAAALFVLMGAYRGGPTTFSVIGLASKPIHVYGKPWYKCEW
ISNNGTSIRAKAQKILPDWGYGRVYTVVVVNCTFNSNPNSDNTGGKLIL
NAYYNESPKLFERFTTLEESAGIYDESKYSPPYQYDYLYCGSSLYGNVS
ASRMREWMAYHAWFFGDKSHFVFHDAGGVSPEVRKVLEPWIRAGRVTVQ
NIRDQSQYDGYYYNQFLIVNDCLHRYRYAANWTFFFDVDEYIYLPHGNT
LESVLDEFSVNTQFTIEQNPMSSVLCINDSSQDYPRQWGFEKLLFKDSR
TKIRRDRKYAIQAKNAFATGVHMSENIVGKTLHKTETKIRYYHYHNTIT
VHEELCREMLPNSAKKKVTLYNKLPYVYDDNMKKLVKTIKEFEQKKLGT
DVKNFS*

GALS2 (*ARABIDOPSIS THALIANA*_AT5G44670)
ACCESSION NO: NP_199280.1 GENE ID: 834496
SEQ ID NO: 2
MAKERDQNTKDKNLLICFLWNFSAELKLALMALLVLCTLATLLPFLPSS
FSISASELRFCISRIAVNSTSVNFTTVVEKPVLDNAVKLTEKPVLDNGV
TKQPLTEEKVLNNGVIKRTFTGYGWAAYNFVLMNAYRGGVNTFAVIGLS
SKPLHVYSHPTYRCEWIPLNQSDNRILTDGTKILTDWGYGRVYTTVVVN
CTFPSNTVINPKNTGGTLLLHATTGDTDRNITDSIPVLTETPNTVDFAL
YESNLRRREKYDYLYCGSSLYGNLSPQRIREWIAYHVRFFGERSHFVLH
DAGGITEEVFEVLKPWIELGRVTVHDIREQERFDGYYHNQFMVVNDCLH
RYRFMAKWMFFFDVDEFIYVPAKSSISSVMVSLEEYSQFTIEQMPMSSQ
LCYDGDGPARTYRKWGFEKLAYRDVKKVPRRDRKYAVQPRNVFATGVHM
SQHLQGKTYHRAEGKIRYFHYHGSISQRREPCRHLYNGTRIVHENNPYV
LDTTMRDIGLAVKTFEIRTIGDRLLRTRQ*

-continued
GALS3 (*ARABIDOPSIS THALIANA*_AT4G20170)
PROTEIN ACCESSION NO: NP_193750.1 GENE ID: 827763
SEQ ID NO: 3
MAMVKEKEQNTKDKKLLVGVIWNFSAELKLTFMALLVLCTLATLLPFIP
SSFSLSTSDFRFCISRFSSAVPLNTTTTVEESSSSPSPEKNLDRVLDNG
VIKRTFTGYGSAAYNFVSMSAYRGGVNSFAVIGLSSKPLHVYGHPSYRC
EWVSLDPTQDPISTTGFKILTDWGYGRIYTTVVVNCTFSSISAVNPQNS
GGTLILHATTGDPTLNLTDSISVLTEPPKSVDFDLYNSTKKTKKYDYLY
CGSSLYGNLSPQRVREWIAYHVRFFGERSHFVLHDAGGIHEEVFEVLKP
WIELGRVTLHDIRDQERFDGYYHNQFMIVNDCLHRYRFMTKWMFFFDVD
EFLHVPVKETISSSVMESLEEYSQFTIEQMPMSSRICYSGDGPARTYRKW
GIEKLAYRDVKKVPRRDRKYAVQPENVFATGVHMSQNLQGKTYHKAESK
IRYFHYHGSISQRREPCRQLFNDSRVVFENTPYVLDTTICDVGLAVRTF
ELRTIGDRLLRTRQ*

GALS1 (*ARABIDOPSIS THALIANA* AT2G33570)
ACCESSION NUMBER: NM_128917' 1838 BP MRNA
SEQ ID NO: 42

```
  1  CTAATTTCTA CACGCCGTGT CGGCAAAGCC TCTCGTCACT
     TCTCTCTGAC GCTTGTCGTC

61  ACTTTTGAAT TTTTTTAATT TTTAAATAAT TGATAACCGA
     AACGGTGCGT TTTACTCACC

121  GTCGTCGGGA AAAAAACAT GAGGAAGGAA GTTTTGCCGC
     CGGTGTTATC AACCACCACA

181  GTATGTTTCG AGAAGAAACC AATAATTGCT ACATTACTAG
     CTCTCTCTCT CGTCATGATT

241  GTCTGGAACC TTCCTCCTTA CTACCACAAC CTCATCTCCA
     CCGCTCGTCC CTGCTCCGCC

301  GTCACCACCA CCACCACCAC CACCTTACTC TCCTCATCGA
     ACTTCACTTC GGCGGAGAAT

361  TTCACCACCT CTCTCTCAAC GACAACTGCA GCAGCTTCTC
     AGAAGTACGA TTCAACTCCC

421  TCAGATCCGA ACAAACGCGT TTTCCAACCG TTCGGAAACG
     CGGCGGCGTT ATTCGTACTA

481  ATGGGAGCTT ACCGCGGCGG TCCAACGACG TTTTCCGTTA
     TCGGACTCGC GTCGAAACCG

541  ATCCACGTTT ACGGAAAACC ATGGTACAAG TGTGAGTGGA
     TATCTAACAA TGGAACTTCG

601  ATTCGAGCTA AAGCACAGAA GATTCTACCA GATTGGGGAT
     ACGGACGAGT CTACACCGTC

661  GTCGTCGTCA ATTGCACTTT CAATTCAAAC CCTAACTCCG
     ATAACACCGG AGGTAAACTC

721  ATTCTCAACG CTTACTACAA CGAATCTCCC AAACTCTTTG
     AACGATTCAC TACGTTAGAA

781  GAATCAGCTG GAATCTACGA CGAATCGAAA TACTCGCCGC
     CGTATCAGTA CGATTACCTC

841  TATTGTGGCT CGTCACTGTA CGGTAACGTG AGCGCGTCGC
     GTATGAGAGA GTGGATGGCT

901  TACCACGCTT GGTTCTTTGG TGACAAATCG CATTTTGTTT
     TCCACGATGC TGGTGGTGTG

961  TCGCCGGAAG TTAGGAAGGT TCTTGAGCCG TGGATTCGAG
     CTGGGAGGGT CACGGTTCAG

1021 AATATTCGGG ATCAGTCGCA GTATGATGGT TACTACTATA
     ATCAGTTTCT TATTGTTAAT

1081 GATTGCTTGC ATCGGTATCG ATACGCTGCG AATTGGACCT
     TCTTCTTCGA TGTCGATGAG

1141 TATATCTATT TGCCGCATGG TAATACACTC GAATCCGTGC
     TCGATGAGTT CTCGGTTAAC

1201 ACGCAGTTTA CGATTGAGCA GAATCCAATG TCTAGTGTTC
     TTTGCATAAA CGACTCTTCT
```

| 1261 | CAAGATTATC CAAGGCAATG GGGATTTGAG AAATTGTTAT TTAAGGATTC AAGGACGAAG |
| 1321 | ATACGACGTG ATAGAAAATA TGCAATCCAA GCGAAGAACG CATTTGCTAC AGGAGTTCAT |
| 1381 | ATGTCTGAAA ACATTGTAGG CAAAACACTA CACAAGACAG AGACAAAGAT TCGTTATTAC |
| 1441 | CATTACCACA ACACCATAAC TGTGCATGAG GAGCTTTGTA GAGAGATGTT ACCAAATTCA |
| 1501 | GCCAAGAAGA AGGTGACATT GTACAATAAG CTTCCGTATG TGTATGATGA CAACATGAAG |
| 1561 | AAGCTAGTGA AGACGATTAA AGAGTTTGAG CAGAAAAAAC TTGGGACGGA TGTGAAGAAT |
| 1621 | TTCTCATGAC CATAATATAG CTGTAATCTC TCTGATAAGC ATTTTGTCTA TAAAGGTATA |
| 1681 | GTTGTTTCTA CATTACATGT ATCATTTTTC ATTCTGTTTT GTCCTCTTTT ACTATTTCAT |
| 1741 | TAATGACTTT GATCAATATT TTTGAAAATT ACTTGTGTTT TCTTTTGTTA TGTATTGAAC |
| 1801 | TTAATAGAAA TTAGAGTTAC TCAAGACCTT GGA-CATAC// |

GALS2 (*ARABIDOPSIS THALIANA* AT5G44670)
ACCESSION NUMBER: NM_123834; 1983 BP MRNA
SEQ ID NO: 43

| 1 | AAATTCTCCA AATTTTTTCT TCTCTCTCTC TTCCCTCTGT CGCTTCACTT TCCCTCTGCT |
| 61 | TCATAGTTCA TACGATTCTT CGATTCGTCT TCTTCAATCA GTGAAGAAGA ACTCAAAAGA |
| 121 | TGGCTAAAGA GAGAGACCAA AACACTAAAG ACAAAAACCT CCTCATCTGT TTCTTATGGA |
| 181 | ACTTCTCCGC CGAGCTTAAG CTAGCTCTAA TGGCGTTACT CGTTCTCTGC ACTTTAGCTA |
| 241 | CTCTCCTCCC TTTTCTACCT TCTTCTTTCT CCATCTCCGC TTCCGAACTC CGTTTCTGCA |
| 301 | TCTCACGCAT CGCCGTAAAC TCCACCTCCG TCAACTTCAC CACCGTCGTC GAAAAGCCAG |
| 361 | TCTTAGATAA CGCTGTCAAG TTAACTGAGA AGCCGGTGTT GGATAACGGC GTTACGAAAC |
| 421 | AGCCGTTAAC TGAAGAGAAG GTGTTAAATA ACGGCGTTAT TAAACGGACG TTTACTGGTT |
| 481 | ACGGCTGGGC AGCTTATAAC TTCGTGTTAA TGAACGCTTA CAGAGGCGGC GTTAACACAT |
| 541 | TCGCCGTTAT CGGTTATCA TCTAAACCAC TTCACGTTTA CTCTCATCCC ACTTACCGTT |
| 601 | GCGAATGGAT TCCACTAAAC CAATCCGATA ACCGGATTTT AACCGACGGT ACCAAAATCT |
| 661 | TAACCGATTG GGGTTACGGT AGAGTTTACA CAACCGTCGT CGTAAACTGT ACTTTTCCGT |
| 721 | CAAACACCGT GATAAACCCT AAAAACACCG GAGGTACTCT TCTCCTCCAC GCAACCACCG |
| 781 | GAGATACAGA CCGGAACATC ACCGATTCAA TTCCGGTACT CACCGAAACT CCAAACACCG |
| 841 | TCGATTTTGC TCTCTACGAA TCCAATCTCC GCCGGCGAGA GAAGTACGAT TATCTCTATT |
| 901 | GTGGATCTTC TCTCTACGGC AACTTATCAC CACAGAGAAT CAGAGAATGG ATCGCTTACC |

| 961 | ATGTAAGGTT CTTCGGTGAA AGATCTCATT TTGTTCTACA TGACGCCGGA GGGATTACAG |
| 1021 | AGGAAGTGTT TGAGGTTTTA AAGCCATGGA TAGAGCTTGG GAGAGTTACT GTTCATGATA |
| 1081 | TTAGAGAACA AGAGAGATTT GATGGTTATT ATCATAATCA ATTCATGGTG GTGAATGATT |
| 1141 | GTTTGCATAG GTATAGATTC ATGGCGAAGT GGATGTTTTT CTTCGATGTT GATGAGTTTA |
| 1201 | TTTATGTTCC GGCGAAGAGT TCGATTTCGT CGGTGATGGT ATCTTTGGAG GAATATTCTC |
| 1261 | AGTTTACTAT TGAACAGATG CCTATGAGTA GTCAGCTTTG TTACGACGGT GATGGTCCGG |
| 1321 | CGAGGACTTA CAGGAAATGG GGATTTGAGA AATTGGCGTA TAGAGATGTG AAGAAAGTAC |
| 1381 | CACGACGGGA TAGGAAGTAT GCGGTTCAAC CGCGGAACGT ATTTGCGACA GGGGTTCACA |
| 1441 | TGTCTCAGCA TCTACAAGGA AAGACGTATC ACAGAGCGGA AGGGAAAATA CGCTATTTTC |
| 1501 | ACTACCATGG TTCAATCTCG CAGCGTCGTG AGCCTTGTCG TCATCTTTAT AACGGTACCC |
| 1561 | GTATCGTTCA TGAGAACAAT CCTTACGTGC TTGATACCAC AATGCGTGAT ATTGGTCTCG |
| 1621 | CGGTGAAGAC GTTTGAGATT AGGACGATTG GAGATCGCTT GCTTAGGACG AGACAATGAA |
| 1681 | GGCAGGAGAA GAATGGTTAA AGACATGTTA TCATCATTAT GCGTTGTAAC GTAAATCTTT |
| 1741 | TAGAGTATTA TTTAGGCCAA TGTAACAATT TTCATGGTTT TTTGTTTAGT ATATTCTTTT |
| 1801 | ATTGTATTAT AAAATGGGTT CGTACATAGA GATCATCATA CAGCTCAGAT TCTTGGTATA |
| 1861 | TAAGCATCTT TTTTATGGGC TTTATAATTT TTTCCGTTAT TTATGAAAA GTGCTTTATA |
| 1921 | TAAATTAGTG AAAGTTGTTG TGGTCTTCCA TGGATCTTTG TCGTGTTAAT TAAAAGTTTC |
| 1981 | CAC // |

GALS3 (*ARABIDOPSIS THALIANA* AT4G20170)
ACCESSION NUMBER: NM_118136 1993 BP MRNA
SEQ ID NO: 44

| 1 | AAAAGTGAGA GACACACAAC TTCGGAGCGA ATCTATTCTT CTTCTTCTTC TTCTTCTTCT |
| 61 | TCTTCTTCTT CCTCCGTTTT TTTCATCTTC TTCTCTGTTT CGAGAGATCC ACTAGTGAAA |
| 121 | GAGTCAGCAC CATGGCCATG GTCAAAGAGA AGAACAAAA CACTAAAGAC AAAAACTCC |
| 181 | TCGTCGGCGT CATTTGGAAC TTCTCCGCCG AGCTCAAGCT CACTTTCATG GCGTTACTTG |
| 241 | TTCTCTGCAC TTTAGCTACT CTCTTACCTT TCATACCTTC TTCATTCTCT CTCTCCACTT |
| 301 | CCGATTTCCG CTTCTGCATC TCACGCTTCT CCTCCGCCGT CCCTCTCAAC ACCACCACCA |
| 361 | CCGTAGAAGA ATCATCATCC TCACCGTCAC CGGAGAAGAA CCTAGATCGA GTTTTGGATA |
| 421 | ACGGAGTTAT TAACGGACG TTTACTGGCT ACGGCTCAGC AGCTTATAAC TTCGTCTCAA |

```
 481  TGAGTGCTTA CAGAGGCGGC GTTAACTCAT TCGCCGTTAT
      CGGATTATCA TCAAAACCAT

541  TACACGTGTA CGGTCATCCT TCGTATAGAT GCGAATGGGT
      CTCATTAGAC CCGACTCAAG

601  ATCCGATTTC AACAACGGGT TTTAAAATCT TAACCGATTG
      GGGTTACGGA CGGATCTACA

661  CAACAGTCGT CGTTAACTGT ACTTTCTCAT CAATCTCCGC
      CGTGAATCCA CAAAACTCCG

721  GTGGAACTCT CATCCTCCAC GCCACCACCG GAGATCCAAC
      TCTCAATCTC ACCGATTCAA

781  TCTCAGTCCT AACCGAACCT CCCAAATCCG TCGATTTCGA
      TCTCTATAAC TCCACGAAGA

841  AGACGAAGAA GTACGATTAT CTCTATTGCG GATCGTCCTT
      ATACGGTAAC CTAAGTCCGC

901  AACAGTTAG AGAATGGATC GCTTACCACG TTAGATTCTT
      CGGTGAACGG TCACATTTCG

961  TGCTACACGA CGCCGGAGGG ATTCATGAGG AAGTGTTCGA
      GGTTTTAAAG CCATGGATTG

1021  AGCTAGGGAG AGTGACGTTA CATGATATTA GAGATCAAGA
      ACGATTCGAT GGATATTATC

1081  ATAATCAGTT CATGATAGTG AATGATTGTT TGCATAGGTA
      TAGATTCATG ACGAAGTGGA

1141  TGTTCTTCTT TGATGTTGAT GAGTTTTTAC ATGTTCCAGT
      GAAAGAGACG ATTTCGTCTG

1201  TGATGGAATC TTTGGAGGAA TATTCTCAGT TTACTATTGA
      ACAGATGCCT ATGAGTAGTC

1261  GGATTTGTTA TTCCGGTGAT GGTCCGGCGA CAACTTACAG
      GAAATGGGGA ATTGAGAAAC

1321  TGGCATATAG AGACGTCAAG AAGGTTCCAA GACGGGATCG
      AAAATACGCT GTCCAGCCGG
```
```
1381  AGAATGTATT CGCGACAGGC GTACACATGT CTCAGAATCT
      ACAAGGGAAA ACATACCACA

1441  AGGCTGAAAG CAAAATCCGT TACTTCCACT ACCATGGTTC
      GATCTCTCAG CGCCGCGAGC

1501  CTTGTCGTCA ACTTTTTAAC GATTCTCGAG TCGTGTTCGA
      GAACACTCCT TATGTGCTAG

1561  ACACTACAAT ATGTGATGTT GGCCTTGCTG TGAGAACGTT
      CGAGTTGAGA ACGATCGGTG

1621  ATCGGCTGCT ACGGACAAGA CAATGAAGAG ATGGCAAAAA
      TGAATAGTGA ATGTAATCAA

1681  TCTTTAGAAA GAAGAATTAG AAGGTGTTAA GATGAGTTAC
      TTTGTATTAT TTTCTTTTGG

1741  GGGTATATTC TTTTATTGTA TCATATAATT TGGGTAATGG
      GTTCATTAAT ACAGCTTGAA

1801  AATACTCTTT GGTATATATA TTCTGTATGA TGTATGATTT
      AGAAAAAAGG TCTCTGAGTA

1861  TATAATCTAG TGATGATAAT TGTGGAGATC AAGTAATATC
      ACTGTTTGTA TTTGATTACT

1921  GTACTCTTAG TTGACAAAAA GAAAATGTCA ATATCCATTG
      GTGTTACTCC AGTAATCCAT

1981  ATGGAACGTT GAT //

UDP-D-GLUCOSE/UDP-D-GALACTOSE 4-EPIMERASE 2
(ARABIDOPSIS THALIANA)
GI|332659427|GB|AEE84827.1
                                    SEQ ID NO: 45
MAKSVLVTGGAGYIGSHTVLQLLEGGYSAVVVDNYDNSSAASLQRVKKL
AGENGNRLSPHQVDLRDRPALEKIFSETKFDAVIHFAGLKAVGESVEKP
LLYYNNNIVGTVTLLEVMAQYGCKNLVFSSSATVYGWPKEVPCTEESPI
SATNPYGRTKLFIEEICRDVHRSDSEWKIILLRYFNPVGAHPSGYIGED
PLGVPNNLMPYVQQVAVGRRPHLTVFGTDYKTKDGTGVRDYIHVMDLAD
GHIAALRKLDDLKISCEVYNLGTGNGTSVLEMVAAFEKASGKKIPLVMA
GRRPGDAEVVYASTEKAERELNWKAKNGIEEMCRDLWNWASNNPYGYNS
SSNGSSS
```

What is claimed is:

1. A method of engineering a plant to increase the galactan content in a desired tissue, the method comprising:
introducing an expression cassette into the plant, wherein the expression cassette comprises a polynucleotide encoding a β-1,4-galactan synthase (GALS) having beta-1,4 galactosyltransferase activity operably linked to a heterologous promoter, wherein the GALS has at least 70% identity to SEQ ID NO:1, and comprises (F/Y/V)G(N/S/T)AAALFV(L/Q)MGAYRGGP (SEQ ID NO:46), SKPIHVYGKPWYKCEWISN (SEQ ID NO:47), KILPDWGYGRVYTVVVVNCTF (SEQ ID NO:48), GG(K/R)LI(L/V/I) (SEQ ID NO:49), Y(D/E)YLYCGSSL(Y/F)G (SEQ ID NO:50), REWMAYHAWFFG (SEQ ID NO:51), SHFVFHDAGG (SEQ ID NO:52), QNIRDQ (SEQ ID NO:53), GYYYNQFLIVNDCLHRYRYAANWTFFDVDEY (SEQ ID NO:54), FTIEQNPMS (SEQ ID NO:55), WGFEKLLFK (SEQ ID NO:56), RRDRKYAIQ (SEQ ID NO:57), RYYHYHNSI (SEQ ID NO:58), and ELCRE (SEQ ID NO:59);

culturing the plant under conditions in which the GALS is expressed; and selecting a plant that has increased beta-1,4-galactan content or increased galactose content in the tissue in which the GALS1 is expressed compared to a wild-type plant that is not engineered to contain the expression cassette.

2. The method of claim 1, wherein the plant is genetically modified to overexpress a UDP-galactose epimerase in the same plant tissue in which GALS is overexpressed.

3. The method of claim 1, wherein the plant is genetically modified to overexpress a transcription factor that induces expression through the heterologous promoter.

4. The method of claim 3, wherein expression of the transcription factor is driven by a promoter that is activated by the transcription factor.

5. The method of claim 1, wherein the plant is genetically modified to overexpress a UDP-galactose epimerase in the same plant tissue in which GALS is overexpressed and is genetically modified to overexpress a transcription factor that induces expression through the heterologous promoter.

6. The method of claim 5, wherein expression of the GALS, UDP-galactose epimerase and the transcription factor is driven by a promoter that is activated by the transcription factor.

7. The method of claim 1, wherein promoter is an IRX1, IRX3, IRX5, IRX8, IRX9, IRX14, IRX7, IRX10, GAUT13, GAUT14, or CESA4 promoter.

8. The method of claim 7, wherein the promoter is an IRX5 or IRX8 promoter.

9. The method of claim 3, wherein the transcription factor is NST1.

10. The method of claim 1, wherein the GALS has at least 90% identity to SEQ ID NO:1.

11. The method of claim 10, wherein the GALS has at least 95% identity to SEQ ID NO:1.

12. The method of claim 1, wherein the plant is Arabidopsis, poplar, eucalyptus, rice, corn, cotton, switchgrass, sorghum, millet, miscanthus, sugarcane, pine, alfalfa, wheat, soy, barley, turfgrass, tobacco, hemp, bamboo, rape, sunflower, willow, or Brachypodium.

13. A method of obtaining an increased amount of soluble sugars from a plant in a saccharification reaction, the method comprising:

subjecting a plant selected by the method of claim 1, or a progeny of said plant comprising the polynucleotide encoding the GALS operably linked to the heterologous promoter, to a saccharification reaction, thereby increasing the amount of soluble sugars that can be obtained from the plant as compared to a wild-type plant.

14. A method of engineering a plant having decreased galactan content, the method comprising:

introducing a polynucleotide that targets and inactivates expression of a gene encoding a GALS having at least 60% identity to SEQ ID NO:1, wherein the polynucleotide is operably linked to a heterologous promoter;

culturing the plant under conditions in which the polynucleotide is expressed;

and selecting a plant that has decreased beta-1,4-galactan content or decreased cell wall galactose content compared to a wild-type plant that is not engineered to inhibit expression of the gene encoding GALS.

15. The method of claim 1, wherein the polynucleotide encoding the GALS encodes the polypeptide of SEQ ID NO:1.

* * * * *

SEQUENCE LISTING

<160> NUMBER OF SEQ ID NOS: 59

<210> SEQ ID NO 1
<211> LENGTH: 496
<212> TYPE: PRT
<213> ORGANISM: Arabidopsis thaliana
<220> FEATURE:
<223> OTHER INFORMATION: GALS1, At2g33570, glycosyltransferase family 92
      (GT92) member, galactan synthase 1,
      beta-1,4,galactan synthase, beta-1,4
      galactosyltransferase (GALS)

<400> SEQUENCE: 1

Met Arg Lys Glu Val Leu Pro Pro Val Leu Ser Thr Thr Val Cys
 1               5                  10                  15

Phe Glu Lys Lys Pro Ile Ile Ala Thr Leu Leu Ala Leu Ser Leu Val
                20                  25                  30

Met Ile Val Trp Asn Leu Pro Pro Tyr Tyr His Asn Leu Ile Ser Thr
            35                  40                  45

Ala Arg Pro Cys Ser Ala Val Thr Thr Thr Thr Thr Thr Leu Leu
        50                  55                  60

Ser Ser Ser Asn Phe Thr Ser Ala Glu Asn Phe Thr Thr Ser Leu Ser
65                  70                  75                  80

-continued

```
Thr Thr Thr Ala Ala Ala Ser Gln Lys Tyr Asp Ser Thr Pro Ser Asp
                 85                  90                  95

Pro Asn Lys Arg Val Phe Gln Pro Phe Gly Asn Ala Ala Ala Leu Phe
            100                 105                 110

Val Leu Met Gly Ala Tyr Arg Gly Pro Thr Thr Phe Ser Val Ile
            115                 120                 125

Gly Leu Ala Ser Lys Pro Ile His Val Tyr Gly Lys Pro Trp Tyr Lys
            130                 135                 140

Cys Glu Trp Ile Ser Asn Gly Thr Ser Ile Arg Ala Lys Ala Gln
145                 150                 155                 160

Lys Ile Leu Pro Asp Trp Gly Tyr Gly Arg Val Tyr Thr Val Val
            165                 170                 175

Val Asn Cys Thr Phe Asn Ser Asn Pro Asn Ser Asp Asn Thr Gly Gly
            180                 185                 190

Lys Leu Ile Leu Asn Ala Tyr Tyr Asn Glu Ser Pro Lys Leu Phe Glu
            195                 200                 205

Arg Phe Thr Thr Leu Glu Glu Ser Ala Gly Ile Tyr Asp Glu Ser Lys
            210                 215                 220

Tyr Ser Pro Pro Tyr Gln Tyr Asp Tyr Leu Tyr Cys Gly Ser Ser Leu
225                 230                 235                 240

Tyr Gly Asn Val Ser Ala Ser Arg Met Arg Glu Trp Met Ala Tyr His
            245                 250                 255

Ala Trp Phe Phe Gly Asp Lys Ser His Phe Val Phe His Asp Ala Gly
            260                 265                 270

Gly Val Ser Pro Glu Val Arg Lys Val Leu Glu Pro Trp Ile Arg Ala
            275                 280                 285

Gly Arg Val Thr Val Gln Asn Ile Arg Asp Gln Ser Gln Tyr Asp Gly
            290                 295                 300

Tyr Tyr Tyr Asn Gln Phe Leu Ile Val Asn Asp Cys Leu His Arg Tyr
305                 310                 315                 320

Arg Tyr Ala Ala Asn Trp Thr Phe Phe Asp Val Asp Glu Tyr Ile
            325                 330                 335

Tyr Leu Pro His Gly Asn Thr Leu Glu Ser Val Leu Asp Glu Phe Ser
            340                 345                 350

Val Asn Thr Gln Phe Thr Ile Glu Gln Asn Pro Met Ser Ser Val Leu
            355                 360                 365

Cys Ile Asn Asp Ser Ser Gln Asp Tyr Pro Arg Gln Trp Gly Phe Glu
            370                 375                 380

Lys Leu Leu Phe Lys Asp Ser Arg Thr Lys Ile Arg Arg Asp Arg Lys
385                 390                 395                 400

Tyr Ala Ile Gln Ala Lys Asn Ala Phe Ala Thr Gly Val His Met Ser
            405                 410                 415

Glu Asn Ile Val Gly Lys Thr Leu His Lys Thr Glu Thr Lys Ile Arg
            420                 425                 430

Tyr Tyr His Tyr His Asn Thr Ile Thr Val His Glu Glu Leu Cys Arg
            435                 440                 445

Glu Met Leu Pro Asn Ser Ala Lys Lys Val Thr Leu Tyr Asn Lys
            450                 455                 460

Leu Pro Tyr Val Tyr Asp Asp Asn Met Lys Lys Leu Val Lys Thr Ile
465                 470                 475                 480

Lys Glu Phe Glu Gln Lys Lys Leu Gly Thr Asp Val Lys Asn Phe Ser
            485                 490                 495
```

<210> SEQ ID NO 2
<211> LENGTH: 519
<212> TYPE: PRT
<213> ORGANISM: Arabidopsis thaliana
<220> FEATURE:
<223> OTHER INFORMATION: GALS2, At5g44670, glycosyltransferase family 92
      (GT92) member, galactan synthase 2,
      beta-1,4,galactan synthase, beta-1,4
      galactosyltransferase (GALS)

<400> SEQUENCE: 2

| | | | | | | | | | | | | | | |
|---|---|---|---|---|---|---|---|---|---|---|---|---|---|---|
| Met | Ala | Lys | Glu | Arg | Asp | Gln | Asn | Thr | Lys | Asp | Lys | Asn | Leu | Leu | Ile |
| 1 | | | | 5 | | | | | 10 | | | | | 15 | |
| Cys | Phe | Leu | Trp | Asn | Phe | Ser | Ala | Glu | Leu | Lys | Leu | Ala | Leu | Met | Ala |
| | | | 20 | | | | | 25 | | | | | 30 | | |
| Leu | Leu | Val | Leu | Cys | Thr | Leu | Ala | Thr | Leu | Leu | Pro | Phe | Leu | Pro | Ser |
| | | | 35 | | | | | 40 | | | | | 45 | | |
| Ser | Phe | Ser | Ile | Ser | Ala | Ser | Glu | Leu | Arg | Phe | Cys | Ile | Ser | Arg | Ile |
| | | | 50 | | | | | 55 | | | | | 60 | | |
| Ala | Val | Asn | Ser | Thr | Ser | Val | Asn | Phe | Thr | Thr | Val | Val | Glu | Lys | Pro |
| 65 | | | | | 70 | | | | | 75 | | | | | 80 |
| Val | Leu | Asp | Asn | Ala | Val | Lys | Leu | Thr | Glu | Lys | Pro | Val | Leu | Asp | Asn |
| | | | | 85 | | | | | 90 | | | | | 95 | |
| Gly | Val | Thr | Lys | Gln | Pro | Leu | Thr | Glu | Glu | Lys | Val | Leu | Asn | Asn | Gly |
| | | | 100 | | | | | 105 | | | | | 110 | | |
| Val | Ile | Lys | Arg | Thr | Phe | Thr | Gly | Tyr | Gly | Trp | Ala | Ala | Tyr | Asn | Phe |
| | | | 115 | | | | | 120 | | | | | 125 | | |
| Val | Leu | Met | Asn | Ala | Tyr | Arg | Gly | Gly | Val | Asn | Thr | Phe | Ala | Val | Ile |
| | | | 130 | | | | | 135 | | | | | 140 | | |
| Gly | Leu | Ser | Ser | Lys | Pro | Leu | His | Val | Tyr | Ser | His | Pro | Thr | Tyr | Arg |
| 145 | | | | | 150 | | | | | 155 | | | | | 160 |
| Cys | Glu | Trp | Ile | Pro | Leu | Asn | Gln | Ser | Asp | Asn | Arg | Ile | Leu | Thr | Asp |
| | | | | 165 | | | | | 170 | | | | | 175 | |
| Gly | Thr | Lys | Ile | Leu | Thr | Asp | Trp | Gly | Tyr | Gly | Arg | Val | Tyr | Thr | Thr |
| | | | 180 | | | | | 185 | | | | | 190 | | |
| Val | Val | Val | Asn | Cys | Thr | Phe | Pro | Ser | Asn | Thr | Val | Ile | Asn | Pro | Lys |
| | | | 195 | | | | | 200 | | | | | 205 | | |
| Asn | Thr | Gly | Gly | Thr | Leu | Leu | Leu | His | Ala | Thr | Thr | Gly | Asp | Thr | Asp |
| | | | 210 | | | | | 215 | | | | | 220 | | |
| Arg | Asn | Ile | Thr | Asp | Ser | Ile | Pro | Val | Leu | Thr | Glu | Thr | Pro | Asn | Thr |
| 225 | | | | | 230 | | | | | 235 | | | | | 240 |
| Val | Asp | Phe | Ala | Leu | Tyr | Glu | Ser | Asn | Leu | Arg | Arg | Arg | Glu | Lys | Tyr |
| | | | | 245 | | | | | 250 | | | | | 255 | |
| Asp | Tyr | Leu | Tyr | Cys | Gly | Ser | Ser | Leu | Tyr | Gly | Asn | Leu | Ser | Pro | Gln |
| | | | 260 | | | | | 265 | | | | | 270 | | |
| Arg | Ile | Arg | Glu | Trp | Ile | Ala | Tyr | His | Val | Arg | Phe | Phe | Gly | Glu | Arg |
| | | | 275 | | | | | 280 | | | | | 285 | | |
| Ser | His | Phe | Val | Leu | His | Asp | Ala | Gly | Gly | Ile | Thr | Glu | Glu | Val | Phe |
| | | | 290 | | | | | 295 | | | | | 300 | | |
| Glu | Val | Leu | Lys | Pro | Trp | Ile | Glu | Leu | Gly | Arg | Val | Thr | Val | His | Asp |
| 305 | | | | | 310 | | | | | 315 | | | | | 320 |
| Ile | Arg | Glu | Gln | Glu | Arg | Phe | Asp | Gly | Tyr | Tyr | His | Asn | Gln | Phe | Met |
| | | | | 325 | | | | | 330 | | | | | 335 | |
| Val | Val | Asn | Asp | Cys | Leu | His | Arg | Tyr | Arg | Phe | Met | Ala | Lys | Trp | Met |
| | | | 340 | | | | | 345 | | | | | 350 | | |
| Phe | Phe | Phe | Asp | Val | Asp | Glu | Phe | Ile | Tyr | Val | Pro | Ala | Lys | Ser | Ser |

```
            355                 360                 365
Ile Ser Ser Val Met Val Ser Leu Glu Glu Tyr Ser Gln Phe Thr Ile
    370                 375                 380

Glu Gln Met Pro Met Ser Ser Gln Leu Cys Tyr Asp Gly Asp Gly Pro
385                 390                 395                 400

Ala Arg Thr Tyr Arg Lys Trp Gly Phe Glu Lys Leu Ala Tyr Arg Asp
                405                 410                 415

Val Lys Lys Val Pro Arg Arg Asp Arg Lys Tyr Ala Val Gln Pro Arg
            420                 425                 430

Asn Val Phe Ala Thr Gly Val His Met Ser Gln His Leu Gln Gly Lys
                435                 440                 445

Thr Tyr His Arg Ala Glu Gly Lys Ile Arg Tyr Phe His Tyr His Gly
            450                 455                 460

Ser Ile Ser Gln Arg Arg Glu Pro Cys Arg His Leu Tyr Asn Gly Thr
465                 470                 475                 480

Arg Ile Val His Glu Asn Asn Pro Tyr Val Leu Asp Thr Thr Met Arg
                485                 490                 495

Asp Ile Gly Leu Ala Val Lys Thr Phe Glu Ile Arg Thr Ile Gly Asp
            500                 505                 510

Arg Leu Leu Arg Thr Arg Gln
            515

<210> SEQ ID NO 3
<211> LENGTH: 504
<212> TYPE: PRT
<213> ORGANISM: Arabidopsis thaliana
<220> FEATURE:
<223> OTHER INFORMATION: GALS3, At4g20170, glycosyltransferase family 92
      (GT92) member, galactan synthase 3,
      beta-1,4,galactan synthase, beta-1,4
      galactosyltransferase (GALS)

<400> SEQUENCE: 3

Met Ala Met Val Lys Glu Lys Glu Gln Asn Thr Lys Asp Lys Lys Leu
1               5                   10                  15

Leu Val Gly Val Ile Trp Asn Phe Ser Ala Glu Leu Lys Leu Thr Phe
            20                  25                  30

Met Ala Leu Leu Val Leu Cys Thr Leu Ala Thr Leu Leu Pro Phe Ile
        35                  40                  45

Pro Ser Ser Phe Ser Leu Ser Thr Ser Asp Phe Arg Phe Cys Ile Ser
    50                  55                  60

Arg Phe Ser Ser Ala Val Pro Leu Asn Thr Thr Thr Val Glu Glu
65                  70                  75                  80

Ser Ser Ser Ser Pro Ser Pro Glu Lys Asn Leu Asp Arg Val Leu Asp
                85                  90                  95

Asn Gly Val Ile Lys Arg Thr Phe Thr Gly Tyr Gly Ser Ala Ala Tyr
            100                 105                 110

Asn Phe Val Ser Met Ser Ala Tyr Arg Gly Gly Val Asn Ser Phe Ala
        115                 120                 125

Val Ile Gly Leu Ser Ser Lys Pro Leu His Val Tyr Gly His Pro Ser
    130                 135                 140

Tyr Arg Cys Glu Trp Val Ser Leu Asp Pro Thr Gln Asp Pro Ile Ser
145                 150                 155                 160

Thr Thr Gly Phe Lys Ile Leu Thr Asp Trp Gly Tyr Gly Arg Ile Tyr
                165                 170                 175

Thr Thr Val Val Val Asn Cys Thr Phe Ser Ser Ile Ser Ala Val Asn
```

```
            180                 185                 190
Pro Gln Asn Ser Gly Gly Thr Leu Ile Leu His Ala Thr Thr Gly Asp
        195                 200                 205
Pro Thr Leu Asn Leu Thr Asp Ser Ile Ser Val Leu Thr Glu Pro Pro
        210                 215                 220
Lys Ser Val Asp Phe Asp Leu Tyr Asn Ser Thr Lys Lys Thr Lys Lys
225                 230                 235                 240
Tyr Asp Tyr Leu Tyr Cys Gly Ser Ser Leu Tyr Gly Asn Leu Ser Pro
                245                 250                 255
Gln Arg Val Arg Glu Trp Ile Ala Tyr His Val Arg Phe Phe Gly Glu
                260                 265                 270
Arg Ser His Phe Val Leu His Asp Ala Gly Gly Ile His Glu Glu Val
                275                 280                 285
Phe Glu Val Leu Lys Pro Trp Ile Glu Leu Gly Arg Val Thr Leu His
                290                 295                 300
Asp Ile Arg Asp Gln Glu Arg Phe Asp Gly Tyr Tyr His Asn Gln Phe
305                 310                 315                 320
Met Ile Val Asn Asp Cys Leu His Arg Tyr Arg Phe Met Thr Lys Trp
                325                 330                 335
Met Phe Phe Phe Asp Val Asp Glu Phe Leu His Val Pro Val Lys Glu
                340                 345                 350
Thr Ile Ser Ser Val Met Glu Ser Leu Glu Glu Tyr Ser Gln Phe Thr
                355                 360                 365
Ile Glu Gln Met Pro Met Ser Ser Arg Ile Cys Tyr Ser Gly Asp Gly
                370                 375                 380
Pro Ala Arg Thr Tyr Arg Lys Trp Gly Ile Glu Lys Leu Ala Tyr Arg
385                 390                 395                 400
Asp Val Lys Lys Val Pro Arg Arg Asp Arg Lys Tyr Ala Val Gln Pro
                405                 410                 415
Glu Asn Val Phe Ala Thr Gly Val His Met Ser Gln Asn Leu Gln Gly
                420                 425                 430
Lys Thr Tyr His Lys Ala Glu Ser Lys Ile Arg Tyr Phe His Tyr His
                435                 440                 445
Gly Ser Ile Ser Gln Arg Arg Glu Pro Cys Arg Gln Leu Phe Asn Asp
                450                 455                 460
Ser Arg Val Val Phe Glu Asn Thr Pro Tyr Val Leu Asp Thr Thr Ile
465                 470                 475                 480
Cys Asp Val Gly Leu Ala Val Arg Thr Phe Glu Leu Arg Thr Ile Gly
                485                 490                 495
Asp Arg Leu Leu Arg Thr Arg Gln
                500

<210> SEQ ID NO 4
<211> LENGTH: 524
<212> TYPE: PRT
<213> ORGANISM: Unknown
<220> FEATURE:
<223> OTHER INFORMATION: synthetic GALS Sbi_Sb04g030080.1,
      glycosyltransferase family 92 (GT92) member,
      galactan synthase, beta-1,4,galactan synthase,
      beta-1,4 galactosyltransferase (GALS)

<400> SEQUENCE: 4

Met Lys Tyr Asn Thr Arg Lys Asp Ala Gly Gly Gly Gly Gly Ala Pro
1               5                   10                  15

Phe Ala Val Pro Cys Val Asp Ile Lys Ser Phe Val Ala Ser Leu Ala
```

```
                20              25              30
Phe Leu Thr Leu Phe Val Ala Phe Trp Gln Leu Gln Pro Tyr Gly Ser
            35                  40                  45
Leu Leu Thr Ala Ala Arg Thr Thr Ala Ser Ser Pro Cys Thr Leu
    50                  55                  60
Leu Thr Thr Thr Ala Ala Thr Asp Leu Ala Ser Pro Asp Ala Thr Ser
65                  70                  75                  80
Gly Thr Ala Ala Asn Thr Asn Gln Pro Ala Ala Lys Ala Ala Ala
                85                  90                  95
Ser Asp Thr Ala Ala Ala Ser Asn Ala Ala Pro Val Arg Leu Ala Glu
                100                 105                 110
Ala Ala Arg Leu Ala Arg Pro Glu Asp Pro Asn Lys Arg Val Leu Arg
            115                 120                 125
Pro Tyr Gly Ser Ala Ala Leu Phe Val Gln Met Gly Ala Tyr Arg
            130                 135                 140
Gly Gly Pro Arg Thr Phe Ala Ile Val Gly Leu Ala Ser Lys Pro Thr
145                 150                 155                 160
His Val Phe Gly Thr Pro Tyr Phe Lys Cys Glu Trp Leu Pro Asn Pro
                165                 170                 175
Thr Ala Gly Glu Pro Ser Pro Arg Pro Val Arg Thr Lys Ala Tyr Lys
                180                 185                 190
Met Leu Pro Asp Trp Gly Tyr Gly Arg Val Tyr Thr Val Val Val
        195                 200                 205
Asn Cys Thr Phe Pro Ser Asn Pro Asn Ala Gly Asn Ala Gly Gly Lys
    210                 215                 220
Leu Leu Val His Ala Tyr Tyr Ser Thr Ala Ser Arg Arg Tyr Glu Arg
225                 230                 235                 240
Phe Val Ala Leu Glu Glu Ala Pro Gly Ser Tyr Asp Glu Ser Leu Phe
                245                 250                 255
Ser Pro Pro Phe Gln Tyr Asp Tyr Leu Tyr Cys Gly Ser Ser Leu Tyr
                260                 265                 270
Gly Asn Leu Ser Ala Ser Arg Met Arg Glu Trp Val Ala Tyr His Ala
                275                 280                 285
His Phe Leu Gly Ala Arg Ser His Phe Val Leu His Asp Ala Gly Gly
            290                 295                 300
Ile Ser Pro Glu Val Lys Ala Val Leu Asp Pro Trp Val Arg Ala Gly
305                 310                 315                 320
Arg Val Thr Val Gln Asp Ile Arg Ala Gln Ala Glu Tyr Asp Gly Tyr
                325                 330                 335
Tyr Tyr Asn Gln Phe Leu Val Val Asn Asp Cys Leu His Arg Tyr Arg
            340                 345                 350
His Ala Ala Asn Trp Thr Phe Phe Asp Val Asp Glu Tyr Leu Tyr
            355                 360                 365
Leu Pro Ser Gly Gln Lys Leu Asp Glu Val Leu Gly Gln Leu Ser Gly
        370                 375                 380
Tyr Ser Gln Phe Thr Ile Glu Gln Asn Pro Met Ser Ser Lys Leu Cys
385                 390                 395                 400
Leu Gln Asp Pro Ser Arg Asn Tyr Ser Arg Glu Trp Gly Phe Glu Lys
                405                 410                 415
Leu Val Phe Arg Asn Ser Ile Thr Lys Val Arg Arg Asp Arg Lys Tyr
            420                 425                 430
Ala Ile Gln Ala Arg Asn Ala Tyr Ser Ala Gly Val His Met Ser Gln
            435                 440                 445
```

```
Asn Leu Tyr Gly Arg Thr Thr His Lys Thr Glu Ser Leu Ile Arg Tyr
    450                 455                 460

Tyr His Tyr His Asn Ser Ile Asn Val Met Gly Glu Pro Cys Arg Glu
465                 470                 475                 480

Phe Val Pro Met Pro Ala Asn Gly Ser Lys Thr Met Phe Glu Gly Val
                485                 490                 495

Pro Tyr Val Tyr Asp Asp Asn Met Lys Arg Leu Ala Asp Glu Ile Lys
            500                 505                 510

Arg Phe Glu Lys Val Thr Leu Gly Ser Val Gln Thr
            515                 520

<210> SEQ ID NO 5
<211> LENGTH: 523
<212> TYPE: PRT
<213> ORGANISM: Unknown
<220> FEATURE:
<223> OTHER INFORMATION: synthetic GALS Zma_GRMZM2G164912_T01,
      glycosyltransferase family 92 (GT92) member,
      galactan synthase, beta-1,4,galactan synthase,
      beta-1,4 galactosyltransferase (GALS)

<400> SEQUENCE: 5

Met Lys Tyr Asn Thr Arg Lys Asp Ala Ser Gly Gly Gly Gly Gly Ala
1               5                   10                  15

Pro Phe Ala Ile Pro Cys Val Asp Ile Lys Ser Phe Val Ala Ser Leu
            20                  25                  30

Ala Phe Leu Thr Leu Phe Val Val Phe Trp Gln Leu Gln Pro Tyr Gly
            35                  40                  45

Ser Val Leu Thr Ala Ala Arg Thr Ser Ala Ser Pro Pro Cys Thr Leu
    50                  55                  60

Leu Pro Thr Thr Ala Ala Ile Asp Leu Ala Ser Pro Asp Thr Thr Ser
65                  70                  75                  80

Ser Thr Ala Ala Lys Thr Asp Gln Pro Ala Ala Ala Ala Val Ser
                85                  90                  95

Ala Thr Ala Ala Gly Ala Asn Ala Ala Pro Val Trp Leu Ala Lys Ala
            100                 105                 110

Ala Arg Pro Ala Arg Pro Glu Asp Pro Asn Lys Arg Val Phe Arg Pro
            115                 120                 125

Tyr Gly Ser Ala Ala Ala Leu Phe Val Gln Met Gly Ala Tyr Arg Gly
    130                 135                 140

Gly Pro Arg Thr Phe Ala Ile Val Gly Leu Ala Ser Lys Pro Thr His
145                 150                 155                 160

Val Phe Gly Thr Pro Tyr Phe Lys Cys Glu Trp Leu Pro Asn Pro Thr
                165                 170                 175

Ala Gly Asp Pro Ser Pro Arg Pro Val Arg Thr Lys Ala Tyr Lys Met
            180                 185                 190

Leu Pro Asp Trp Gly Tyr Gly Arg Val Tyr Thr Val Val Val Asn
            195                 200                 205

Cys Thr Phe Pro Ser Asn Pro Asn Ala Arg Asn Ala Gly Gly Lys Leu
    210                 215                 220

Leu Val His Ala Tyr Tyr Ser Thr Ala Ser Arg Arg His Glu Arg Phe
225                 230                 235                 240

Val Ala Leu Glu Glu Ala Pro Gly Ser Tyr Asp Glu Ser Arg Phe Ser
                245                 250                 255

Pro Pro Phe Gln Tyr Asp Tyr Leu Tyr Cys Gly Ser Ser Leu Tyr Gly
            260                 265                 270
```

```
Asn Leu Ser Ala Ser Arg Val Arg Glu Trp Val Ala Tyr His Ala Arg
        275                 280                 285

Phe Leu Gly Pro Arg Ser His Phe Val Leu His Asp Ala Gly Gly Ile
    290                 295                 300

Ser Pro Glu Val Lys Ala Val Leu Asp Pro Trp Val Arg Ala Gly Arg
305                 310                 315                 320

Val Thr Val Gln Asp Ile Arg Ala Gln Ala Glu Tyr Asp Gly Tyr Tyr
                325                 330                 335

Tyr Asn Gln Phe Leu Val Val Asn Asp Cys Leu His Arg Tyr Arg His
            340                 345                 350

Ala Ala Asn Trp Thr Phe Phe Asp Val Asp Glu Tyr Leu Tyr Leu
        355                 360                 365

Pro Asn Gly Gln Lys Leu Ala Glu Val Ile Gly Gln Leu Ser Gly Tyr
    370                 375                 380

Ser Gln Phe Thr Ile Glu Gln Asn Pro Met Ser Ser Lys Leu Cys Leu
385                 390                 395                 400

Gln Asp Pro Ser Arg Asn Tyr Ser Arg Glu Trp Gly Phe Glu Lys Leu
                405                 410                 415

Val Phe Arg Asn Ser Ile Thr Lys Val Arg Arg Asp Arg Lys Tyr Val
            420                 425                 430

Ile Gln Gly Arg Asn Val Tyr Ser Ala Gly Val His Met Ser Gln Asn
        435                 440                 445

Leu Tyr Gly Arg Thr Thr His Lys Thr Glu Gly Leu Ile Arg Tyr Tyr
    450                 455                 460

His Tyr His Asp Ser Ile Asn Val Met Gly Glu Pro Cys Arg Glu Phe
465                 470                 475                 480

Val Pro Met Pro Ala Asn Gly Ser Lys Thr Met Phe Glu Gly Val Pro
                485                 490                 495

Tyr Val Tyr Asp Asp Asn Met Lys Arg Leu Ala Gly Glu Ile Lys Arg
            500                 505                 510

Phe Glu Lys Val Thr Leu Gly Ser Ala Arg Thr
    515                 520
```

<210> SEQ ID NO 6
<211> LENGTH: 498
<212> TYPE: PRT
<213> ORGANISM: Unknown
<220> FEATURE:
<223> OTHER INFORMATION: synthetic GALS Sit_Si017001m,
      glycosyltransferase family 92 (GT92) member, galactan synthase,
      beta-1,4,galactan synthase, beta-1,4
      galactosyltransferase (GALS)

<400> SEQUENCE: 6

```
Met Lys Tyr Asn Ala Arg Lys Asp Ala Gly Gly Gly Gly Gly Gly Ala
1               5                   10                  15

Pro Phe Ala Ile Pro Cys Val Asp Val Lys Ser Phe Val Ala Ser Leu
            20                  25                  30

Ala Phe Leu Thr Leu Phe Val Ala Phe Trp Gln Leu Gln Pro Tyr Gly
        35                  40                  45

Ser Met Leu Thr Ala Ala Arg Thr Ser Ala Ser Pro Cys Ser Leu
    50                  55                  60

Leu Ala Thr Thr Ala Ala Ala Asp Leu Pro Ser Tyr Asn Ala Thr Ala
65                  70                  75                  80

Gly Ala Ala Ala Asp Thr Lys Gln Pro Ala Ala Val Ser Gly Thr Thr
                85                  90                  95
```

```
Thr Ala Ala Ala Asn Ala Ala His Val Arg Leu Ala Arg Pro Ala Arg
            100                 105                 110

Pro Glu Asp Pro Asn Lys Arg Val Leu Arg Pro Tyr Gly Ser Ala Ala
            115                 120                 125

Ala Leu Phe Val Gln Met Gly Ala Tyr Arg Gly Gly Pro Arg Thr Phe
            130                 135                 140

Ala Val Val Gly Leu Ala Ser Lys Pro Thr His Val Phe Gly Thr Pro
145                 150                 155                 160

Tyr Phe Lys Cys Glu Trp Leu Pro Asn Pro Thr Ala Ser Asp Pro Ser
                165                 170                 175

Pro Arg Pro Val Arg Thr Lys Ala Tyr Lys Met Leu Pro Asp Trp Gly
                180                 185                 190

Tyr Gly Arg Val Tyr Thr Val Val Val Asn Cys Thr Phe Pro Ser
                195                 200                 205

Asn Pro Asn Ala Gly Asn Ala Gly Gly Lys Leu Leu Val His Ala Tyr
            210                 215                 220

Tyr Ser Thr Ala Ser Arg Arg Pro Pro Phe Gln Tyr Asp Tyr Leu Tyr
225                 230                 235                 240

Cys Gly Ser Ser Leu Tyr Gly Asn Leu Ser Ala Ser Arg Met Arg Glu
                245                 250                 255

Trp Val Ala Tyr His Ala His Phe Phe Gly Pro Arg Ser His Phe Val
                260                 265                 270

Leu His Asp Ala Gly Gly Ile Ser Pro Glu Val Lys Ala Val Leu Asp
            275                 280                 285

Pro Trp Val Arg Ala Gly Arg Val Thr Val Gln Asp Ile Arg Ala Gln
            290                 295                 300

Ala Glu Tyr Asp Gly Tyr Tyr Tyr Asn Gln Phe Leu Val Val Asn Asp
305                 310                 315                 320

Cys Leu His Arg Tyr Arg His Ala Ala Asn Trp Thr Phe Phe Phe Asp
                325                 330                 335

Val Asp Glu Tyr Leu Tyr Leu Pro Asn Gly Gln Lys Leu Asp Glu Val
            340                 345                 350

Ile Gly Lys Leu Ser Gly Tyr Ser Gln Phe Thr Ile Glu Gln Asn Pro
            355                 360                 365

Met Ser Ser Lys Leu Cys Val Glu Asp Pro Ser Arg Asn Tyr Ser Arg
            370                 375                 380

Glu Trp Gly Phe Glu Lys Leu Val Phe Arg Asn Ser Ile Thr Lys Val
385                 390                 395                 400

Arg Arg Asp Arg Lys Tyr Ala Ile Gln Ala Arg Asn Ala Tyr Ser Thr
                405                 410                 415

Gly Val His Met Ser Gln Asn Val Arg Gly Arg Thr Thr His Lys Thr
            420                 425                 430

Glu Ser Leu Ile Arg Tyr Tyr His Tyr His Asn Ser Ile Asn Val Met
            435                 440                 445

Gly Glu Pro Cys Arg Glu Phe Val Pro Met Pro Val Asn Gly Ser Lys
            450                 455                 460

Ile Met Phe Glu Lys Thr Pro Phe Val Tyr Asp Asp Ser Met Lys Arg
465                 470                 475                 480

Val Ala Gly Glu Ile Lys Arg Phe Glu Lys Glu Thr Ile Gly Ser Val
                485                 490                 495

Gln Thr
```

-continued

<210> SEQ ID NO 7
<211> LENGTH: 518
<212> TYPE: PRT
<213> ORGANISM: Unknown
<220> FEATURE:
<223> OTHER INFORMATION: synthetic GALS Osa_LOC_Os02g48190.1,
      glycosyltransferase family 92 (GT92) member,
      galactan synthase, beta-1,4,galactan synthase,
      beta-1,4 galactosyltransferase (GALS)

<400> SEQUENCE: 7

Met Lys Asn Gly Ala Arg Lys Asp Ala Gly Gly Gly Gly Gly Gly Val
1               5                   10                  15

Phe Val Pro Cys Val Asp Ile Lys Ser Phe Val Leu Ser Leu Ala Phe
            20                  25                  30

Leu Thr Val Phe Val Ala Leu Trp Gln Leu Gln Pro Tyr Gly Ser Leu
        35                  40                  45

Leu Thr Ala Ala Arg Ser Thr Ala Ser Val Ser Ala Ser Pro Cys Ser
    50                  55                  60

Leu Ile Ala Thr Pro Ala Ala Ala Ala Ser Ala Gly Val Ile Arg
65                  70                  75                  80

Ser Glu Asn Ser Thr Ala Asp Thr Ala Lys Thr Ala Pro Ala Ala Val
                85                  90                  95

Ala Ser Ala Val Pro Ala Arg Leu Ala Arg Ala Ala Arg Pro Ala Arg
            100                 105                 110

Val Glu Asp Pro Asn Lys Arg Glu Leu Arg Pro Tyr Gly Ser Ala Ala
        115                 120                 125

Ala Leu Phe Val Gln Met Gly Ala Tyr Arg Gly Gly Pro Arg Thr Phe
    130                 135                 140

Ala Ile Val Gly Leu Ala Ser Lys Pro Thr His Val Phe Ser Asn Pro
145                 150                 155                 160

Tyr Phe Lys Cys Glu Trp Leu Pro Asn Pro Thr Ala Gly Asn Pro Ser
                165                 170                 175

Pro Arg Pro Val Arg Thr Lys Ala Tyr Lys Met Leu Pro Asp Trp Gly
            180                 185                 190

Tyr Gly Arg Val Tyr Thr Val Val Val Asn Cys Thr Phe Pro Ser
        195                 200                 205

Asn Pro Asn Ala Asp Asn Ala Gly Gly Lys Leu Leu Val His Ala Tyr
    210                 215                 220

Tyr Ser Thr Thr Ser Arg Arg Tyr Glu Arg Phe Val Ala Leu Glu Glu
225                 230                 235                 240

Ala Pro Gly Ser Tyr Asp Glu Ser Arg Phe Ser Pro Pro Phe Pro Tyr
                245                 250                 255

Asp Tyr Leu Tyr Cys Gly Ser Ser Leu Tyr Gly Asn Leu Ser Ala Ser
            260                 265                 270

Arg Met Arg Glu Trp Val Ala Tyr His Ala His Phe Gly Pro Arg
        275                 280                 285

Ser His Phe Val Phe His Asp Ala Gly Gly Ile Ser Pro Glu Val Lys
    290                 295                 300

Ala Val Leu Asp Pro Trp Val Arg Ala Gly Arg Leu Thr Val Gln Asp
305                 310                 315                 320

Ile Arg Ala Gln Ala Glu Tyr Asp Gly Tyr Tyr Asn Gln Phe Leu
                325                 330                 335

Val Val Asn Asp Cys Leu His Arg Tyr Arg His Ala Ala Asn Trp Thr
            340                 345                 350

Phe Phe Phe Asp Val Asp Glu Tyr Ile Tyr Leu Pro Asn Gly Gln Thr

```
                355                 360                 365
Leu Asp Gln Val Leu Gly Lys Leu Ser Gly Tyr Ser Gln Phe Thr Ile
370                 375                 380

Glu Gln Asn Pro Met Ser Ser Lys Leu Cys Val Gln Asp Pro Ser Lys
385                 390                 395                 400

Asp Tyr Ser Arg Glu Trp Gly Phe Glu Lys Leu Val Phe Arg Asn Ser
                405                 410                 415

Ile Thr Lys Val Arg Arg Asp Arg Lys Tyr Ala Ile Gln Ala Arg Asn
                420                 425                 430

Ala Tyr Ser Ala Gly Val His Met Ser Gln Asn Val Tyr Gly Arg Thr
                435                 440                 445

Thr His Lys Thr Glu Ser Leu Ile Arg Tyr Tyr His Tyr His Asn Ser
            450                 455                 460

Ile Asn Val Met Gly Glu Pro Cys Arg Glu Phe Val Pro Val Pro Val
465                 470                 475                 480

Asn Gly Ser Lys Leu Met Phe Glu Gly Ile Pro Tyr Val Tyr Asp Asp
                485                 490                 495

Asn Met Lys Arg Leu Ala Gly Gln Ile Lys Arg Phe Glu Lys Glu Ala
                500                 505                 510

Ile Gly Ser Ala His Thr
            515

<210> SEQ ID NO 8
<211> LENGTH: 528
<212> TYPE: PRT
<213> ORGANISM: Unknown
<220> FEATURE:
<223> OTHER INFORMATION: synthetic GALS Bdi_Bradi3g53170.1,
      glycosyltransferase family 92 (GT92) member,
      galactan synthase, beta-1,4,galactan synthase,
      beta-1,4 galactosyltransferase (GALS)

<400> SEQUENCE: 8

Met Lys Gln Asn Ala Arg Lys Asp Pro Gly Gly Gly Gly Gly Gly Ala
1               5                   10                  15

Phe Val Ile Ala Cys Val Asp Ile Lys Leu Phe Val Val Ser Leu Ala
                20                  25                  30

Phe Leu Thr Leu Leu Gly Leu Trp Gln Leu Gln Pro Tyr Gly Ser
            35                  40                  45

Phe Met Ala Ala Ala Arg Ser Ser Ala Asn Ala Pro Pro Cys Phe Leu
        50                  55                  60

Leu Ser Thr Thr Val Ala Ala Val Asn Asn Glu Val Ala Ser Ser Asp
65                  70                  75                  80

Ser Ile Pro Ile Lys Gly Thr Ala Ala Thr Ser Asp Val Pro Ala Asn
                85                  90                  95

Ile Ala Thr Val Pro Ala Arg Pro Ala Arg Pro Ala Arg Val Glu Asn
                100                 105                 110

Gln Asn Lys Arg Val Leu Arg Pro Ala Pro Ala Val Asp Pro Asn Lys
            115                 120                 125

Arg Ala Leu Arg Pro Tyr Gly Ser Ala Ala Leu Phe Val Gln Phe
            130                 135                 140

Gly Ala Tyr Arg Gly Gly Pro Arg Thr Phe Ala Ile Val Gly Leu Ala
145                 150                 155                 160

Ser Lys Pro Thr His Val Phe Gly Thr Pro Tyr Phe Lys Cys Glu Trp
                165                 170                 175

Leu Pro Asn Pro Ser Ala Ala Asp Pro Ala Pro Arg Pro Val Arg Thr
```

```
            180                 185                 190
Lys Ala Tyr Lys Met Leu Pro Asp Trp Gly Tyr Gly Arg Val Tyr Thr
            195                 200                 205
Thr Val Val Asn Cys Thr Phe Pro Ser Asn Pro Asn Val Asp Asn
210                 215                 220
Ala Gly Gly Lys Leu Leu Val His Ala Tyr Tyr Ser Ile His Ser Arg
225                 230                 235                 240
Arg Tyr Glu Arg Phe Val Ala Leu Glu Glu Ala Pro Gly Ser Tyr Asp
            245                 250                 255
Glu Ser Arg Phe Ser Pro Pro Phe Gln Tyr Asp Tyr Leu Tyr Cys Gly
            260                 265                 270
Ser Ser Leu Tyr Gly Asn Leu Ser Ala Ser Arg Met Arg Glu Trp Met
            275                 280                 285
Ala Tyr His Ala His Phe Phe Gly Pro Arg Ser His Phe Val Phe His
            290                 295                 300
Asp Ala Ser Gly Phe Ser Pro Glu Val Lys Ala Val Leu Asp Pro Trp
305                 310                 315                 320
Val Arg Ala Gly Arg Leu Thr Val Gln Asp Val Arg Ala Glu Ala Glu
            325                 330                 335
Tyr Asp Ser Tyr Tyr Asn Gln Phe Leu Val Val Asn Asp Cys Leu
            340                 345                 350
His Arg Tyr Arg His Ala Ala Asn Trp Thr Phe Phe Asp Val Asp
            355                 360                 365
Glu Tyr Met Tyr Leu Pro Asn Gly Arg Thr Leu Asp Gln Val Leu Gly
            370                 375                 380
Asn Leu Ser Gly Tyr Thr Gln Leu Thr Ile Lys Gln Asn Pro Met Ser
385                 390                 395                 400
Ser Lys Leu Cys Leu Lys Asn Pro Ser Lys Asp Ser Ser Arg Glu Trp
            405                 410                 415
Gly Phe Glu Lys Phe Val Phe Phe Asn Ala Val Val Lys Pro Arg Arg
            420                 425                 430
Asp Arg Lys Tyr Ala Val Gln Ala Arg Asn Thr Tyr Ser Ala Gly Val
            435                 440                 445
His Leu Ser Gln Asn Leu Tyr Gly Arg Ser Thr His Asp Thr Glu Asn
            450                 455                 460
Val Ile Arg Tyr Tyr His Phe His Asn Ser Ile Asn Val Leu Gly Glu
465                 470                 475                 480
Pro Cys Lys Lys Phe Val Ala Lys Pro Ala Asn Gly Ser Gln Ile Met
            485                 490                 495
Phe Glu Gly Ala Pro Phe Val Tyr Asp Tyr Asn Leu Lys Arg Leu Ala
            500                 505                 510
Gly Glu Ile Lys Arg Phe Glu Lys Glu Thr Ile Gly Ser Ser His Thr
            515                 520                 525

<210> SEQ ID NO 9
<211> LENGTH: 522
<212> TYPE: PRT
<213> ORGANISM: Unknown
<220> FEATURE:
<223> OTHER INFORMATION: synthetic GALS Sbi_Sb10g013010.1,
      glycosyltransferase family 92 (GT92) member,
      galactan synthase, beta-1,4,galactan synthase,
      beta-1,4 galactosyltransferase (GALS)

<400> SEQUENCE: 9

Met Lys Pro Asp Ala Arg Lys Asp Ala Gly Gly Gly Val Ala Ala Leu
```

```
1               5                    10                   15
Gly Val Ser Cys Phe Asp Ile Lys Ser Phe Val Ala Ser Leu Ala Leu
                20                  25                  30

Leu Thr Leu Val Met Ala Leu Trp Gln Leu His Pro Tyr Gln Pro Leu
            35                  40                  45

Leu Ser Ala Ser Arg Pro Ser Thr Thr Cys Pro Leu Leu Pro Arg Pro
        50                  55                  60

Pro Ile Ser Ala Ser Ser Arg Ala Ala Ala Thr Val Ala Pro Phe Pro
65                  70                  75                  80

Ser Gly Asn Ser Ser Ala Asn Ala Ala Ser Thr Lys Ala Ala Ser Ser
                85                  90                  95

Ala Val Pro Ala Val Thr Thr Thr Lys Pro Ala Ala Ser Val Val Pro
                100                 105                 110

Ala Ala Arg Pro Arg Asp Pro Asn Lys Arg Glu Phe Arg Ser Tyr Gly
            115                 120                 125

Ser Ala Ala Leu Phe Val Gln Met Gly Ala Tyr Arg Gly Gly Pro
        130                 135                 140

Arg Thr Phe Ala Val Ile Gly Leu Ala Ser Lys Pro Ala His Val Tyr
145                 150                 155                 160

Gly Thr Pro Tyr Phe Lys Cys Glu Trp Val Pro Asn Gln Asp Pro Ser
                165                 170                 175

Ser Pro Ala Pro Pro Arg Ala Val Arg Thr Lys Ala Tyr Lys Met Leu
                180                 185                 190

Pro Asp Trp Gly Tyr Gly Arg Ile Tyr Thr Val Val Val Asn Cys
            195                 200                 205

Thr Phe Pro Thr Asn Pro Asn Ala Asp Asn Arg Gly Gly Lys Leu Leu
210                 215                 220

Ile His Ala Tyr Tyr Ser Thr Ala Ser Arg Arg Tyr Glu Arg Phe Val
225                 230                 235                 240

Ala Leu Glu Glu Thr Arg Gly Ser Tyr Asp Glu Ser Arg Phe Arg Pro
            245                 250                 255

Pro Phe Pro Tyr Glu Tyr Leu Tyr Cys Gly Ser Ser Leu Tyr Gly Asn
            260                 265                 270

Leu Ser Ala Ala Arg Met Arg Glu Trp Leu Ala Tyr His Ala His Phe
        275                 280                 285

Phe Gly Pro Ala Ser His Phe Val Leu His Asp Ala Gly Gly Val Ser
        290                 295                 300

Pro Glu Val Arg Ala Val Leu Asp Pro Trp Val Arg Ala Gly Arg Val
305                 310                 315                 320

Thr Val Gln Asp Ile Arg Ala Gln Ala Glu Tyr Asp Gly Tyr Tyr Tyr
                325                 330                 335

Asn Gln Phe Leu Val Val Asn Asp Cys Leu His Arg Tyr Arg His Ala
            340                 345                 350

Ala Asn Trp Thr Phe Phe Asp Val Asp Glu Tyr Ile Tyr Leu Pro
            355                 360                 365

Asp Gly Arg Thr Leu Gln Glu Val Leu Gly Gln Leu Glu Ala Tyr Thr
        370                 375                 380

Gln Phe Thr Ile Glu Gln Asn Pro Met Ser Ser Lys Leu Cys Val Glu
385                 390                 395                 400

Asp Pro Thr Met Glu Tyr Ser Arg Lys Trp Gly Phe Glu Lys Leu Val
                405                 410                 415

Phe Arg Asn Ser Ile Thr Gly Val Arg Arg Asp Arg Lys Tyr Ala Ile
            420                 425                 430
```

```
Gln Ala Arg Asn Ala Tyr Ser Thr Gly Val His Met Ser Gln Asn Val
        435                 440                 445

Ile Gly Arg Thr Thr His Lys Thr Glu Ser Leu Ile Arg Tyr Tyr His
    450                 455                 460

Tyr His Asn Ser Ile Asn Val Met Gly Glu Pro Cys Arg Glu Phe Val
465                 470                 475                 480

Pro Thr Pro Thr Asn Gly Ser Lys Val Met Phe Glu Gly Ile Pro Tyr
            485                 490                 495

Val Tyr Asp Asp Asn Met Lys Arg Ile Thr Gly Glu Ile Lys Arg Phe
                500                 505                 510

Glu Glu Glu Thr Leu Gly Thr Ile Arg Arg
        515                 520

<210> SEQ ID NO 10
<211> LENGTH: 522
<212> TYPE: PRT
<213> ORGANISM: Unknown
<220> FEATURE:
<223> OTHER INFORMATION: synthetic GALS Zma_GRMZM2G136800_T02,
      glycosyltransferase family 92 (GT92) member,
      galactan synthase, beta-1,4,galactan synthase,
      beta-1,4 galactosyltransferase (GALS)

<400> SEQUENCE: 10

Met Lys Pro Asp Val Arg Lys Asp Ala Gly Cys Gly Val Thr Ala Phe
1               5                   10                  15

Gly Val Ser Cys Phe Asp Ile Lys Ser Phe Val Ala Ser Leu Ala Leu
            20                  25                  30

Leu Thr Leu Val Met Ala Leu Trp Gln Leu His Pro Tyr Gln Pro Leu
        35                  40                  45

Leu Ser Ala Ser Arg Pro Ser Ser Ile Cys Pro Leu Leu Pro Arg Pro
    50                  55                  60

Thr Ile Ser Ala Ser Ser Arg Ala Ala Ser Thr Ala Ala Ala Phe Pro
65                  70                  75                  80

Ser Ala Asn Ser Ser Thr Asn Ala Ala Ser Thr Lys Ala Ala Ser Ser
                85                  90                  95

Ala Ala Pro Ala Val Thr Thr Lys Pro Ala Ala Ser Val Leu Pro
            100                 105                 110

Ala Ala Arg Pro Arg Asp Pro Asn Lys Arg Glu Phe Arg Ser Tyr Gly
        115                 120                 125

Ser Ala Ala Ala Leu Phe Val Gln Met Gly Ala Tyr Arg Gly Gly Pro
    130                 135                 140

Arg Thr Phe Ala Val Ile Gly Leu Ala Ser Lys Pro Ala His Val Tyr
145                 150                 155                 160

Asp Thr Pro Tyr Phe Lys Cys Glu Trp Val Pro Asn Gln Glu Pro Ser
                165                 170                 175

Ser Pro Ala Pro Pro Arg Ala Val Arg Thr Lys Ala Tyr Lys Met Leu
            180                 185                 190

Pro Asp Trp Gly Tyr Gly Arg Ile Tyr Thr Val Val Val Asn Cys
        195                 200                 205

Thr Phe Pro Thr Asn Pro Asn Ala Asp Asn Arg Gly Gly Lys Leu Phe
    210                 215                 220

Ile Gln Ala Tyr Tyr Ser Thr Ala Ser Arg Arg Tyr Glu Arg Phe Val
225                 230                 235                 240

Ala Leu Glu Glu Val Pro Gly Ser Tyr Asp Glu Ser Arg Phe Arg Pro
                245                 250                 255
```

```
Pro Phe Pro Tyr Glu Tyr Leu Tyr Cys Gly Ser Ser Leu Tyr Gly Asn
            260                 265                 270

Leu Ser Ala Ala Arg Met Arg Glu Trp Leu Ala Tyr His Ala His Phe
        275                 280                 285

Phe Gly Pro Lys Ser His Phe Val Leu His Asp Ala Gly Gly Val Ser
    290                 295                 300

Thr Glu Val Arg Ala Val Leu Asp Pro Trp Ile Arg Ala Gly Arg Val
305                 310                 315                 320

Thr Val Gln Asp Ile Arg Ala Gln Ala Glu Tyr Asp Gly Tyr Tyr Tyr
                325                 330                 335

Asn Gln Phe Leu Val Val Asn Asp Cys Leu His Arg Tyr Arg His Ala
                340                 345                 350

Ala Asn Trp Thr Phe Phe Asp Val Asp Glu Tyr Ile Tyr Leu Pro
            355                 360                 365

Asp Gly Arg Thr Leu Gln Glu Val Leu Gly Gln Leu Glu Pro Tyr Thr
    370                 375                 380

Gln Phe Thr Ile Glu Gln Asn Pro Met Ser Ser Lys Leu Cys Val Glu
385                 390                 395                 400

Asp Pro Thr Met Glu Tyr Ser Arg Lys Trp Gly Phe Glu Lys Leu Val
                405                 410                 415

Phe Arg Asn Ser Ile Thr Arg Val Arg Arg Asp Arg Lys Tyr Ala Ile
            420                 425                 430

Arg Ala Arg Asn Ala Tyr Ser Thr Gly Val His Met Ser Gln Asn Val
        435                 440                 445

Ile Gly Arg Thr Thr His Lys Thr Glu Ser Leu Ile Leu Tyr Tyr His
    450                 455                 460

Tyr His Asn Ser Ile Asn Val Met Gly Glu Pro Cys Arg Glu Phe Val
465                 470                 475                 480

Pro Arg Pro Asn Asn Gly Ser Lys Val Met Phe Glu Gly Ile Pro Tyr
                485                 490                 495

Val Tyr Asp Asp Asn Met Glu Arg Val Ala Gly Glu Ile Lys Arg Phe
            500                 505                 510

Glu Glu Glu Thr Leu Gly Thr Val Arg Thr
        515                 520

<210> SEQ ID NO 11
<211> LENGTH: 474
<212> TYPE: PRT
<213> ORGANISM: Unknown
<220> FEATURE:
<223> OTHER INFORMATION: synthetic GALS Sit_Si006346m,
      glycosyltransferase family 92 (GT92) member, galactan synthase,
      beta-1,4,galactan synthase, beta-1,4
      galactosyltransferase (GALS)

<400> SEQUENCE: 11

Met Lys Pro Ala Ala Arg Lys Asp Ala Gly Ala Ala Gly Val Ala
1               5                   10                  15

Ala Phe Gly Val Ser Cys Phe Asp Ile Lys Ser Phe Val Ala Ser Leu
            20                  25                  30

Ala Leu Leu Thr Leu Val Met Ala Leu Trp Gln Leu His Pro Tyr Gln
        35                  40                  45

Pro Leu Leu Ser Thr Ser Arg Ser Ser Cys Pro Leu Leu Pro Ser
    50                  55                  60

Gln Pro Ile Ser Ala Ser Ser Arg Ala Ala Thr Ala Ala Ala Leu Pro
65                  70                  75                  80
```

-continued

Thr Ala Asn Ser Thr Ala Asp Ala Ala Asp Thr Lys Thr Ala Pro
            85                  90                  95

Ser Thr Val Pro Ala Ala Thr Ala Thr Lys Pro Asp Ala Ala Val Leu
                100                 105                 110

Pro Ala Ala Arg Pro Arg Asp Pro Asn Lys Arg Asp Leu Arg Pro Tyr
                115                 120                 125

Gly Ser Ala Ala Ala Leu Phe Val Gln Met Gly Ala Tyr Arg Gly Gly
            130                 135                 140

Pro Arg Thr Phe Ala Val Val Gly Leu Ala Ser Lys Pro Ala His Val
145                 150                 155                 160

Phe Gly Thr Pro Tyr Phe Lys Cys Glu Trp Val Pro Asn Leu Asp Pro
                165                 170                 175

Ser Ser Pro Ala Pro Arg Pro Val Arg Thr Lys Ala Tyr Lys Met
                180                 185                 190

Leu Pro Asp Trp Gly Tyr Gly Arg Ile Tyr Thr Val Val Val Asn
            195                 200                 205

Cys Thr Phe Pro Thr Asn Pro Asn Ala Gly Asn Arg Gly Gly Lys Leu
            210                 215                 220

Leu Val His Ala Tyr Tyr Ser Thr Ala Ser Arg Arg Tyr Glu Arg Phe
225                 230                 235                 240

Val Ala Leu Glu Glu Ala Pro Gly Ser Tyr Asp Glu Ser Arg Phe Arg
                245                 250                 255

Pro Pro Phe Pro Tyr Glu Tyr Leu Tyr Cys Gly Ser Ser Leu Tyr Gly
                260                 265                 270

Asn Leu Ser Ala Ala Arg Met Arg Glu Trp Leu Ala Tyr His Ala His
            275                 280                 285

Phe Phe Gly Pro Ser Ser His Phe Val Leu His Asp Ala Gly Gly Val
            290                 295                 300

Ser Pro Glu Val Trp Ala Val Leu Asp Pro Trp Tyr Ile Tyr Leu Pro
305                 310                 315                 320

Asp Gly Arg Thr Leu Gln Glu Val Leu Gly Gln Leu Glu Arg Tyr Thr
                325                 330                 335

Gln Phe Thr Ile Glu Gln Asn Pro Met Ser Ser Lys Leu Cys Val Glu
            340                 345                 350

Asp Pro Asn Lys Glu Tyr Ser Arg Glu Trp Gly Phe Glu Lys Leu Val
            355                 360                 365

Phe Arg Asn Ser Ile Thr Gly Val Arg Arg Asp Arg Lys Tyr Ala Ile
370                 375                 380

Gln Ala Arg Asn Ala Tyr Ser Thr Gly Val His Met Ser Gln Asn Val
385                 390                 395                 400

Ile Gly Arg Thr Ser His Lys Thr Glu Arg Leu Ile Arg Tyr Tyr His
                405                 410                 415

Tyr His Asn Ser Ile Asn Ile Met Gly Glu Pro Cys Arg Glu Phe Val
            420                 425                 430

Gln Lys Pro Thr Asn Gly Ser Lys Val Met Phe Glu Gly Ile Pro Tyr
            435                 440                 445

Val Tyr Asp Asp Asn Met Lys Arg Leu Thr Val Glu Ile Lys Arg Phe
450                 455                 460

Glu Glu Glu Thr Ile Gly Ala Ile His Thr
465                 470

<210> SEQ ID NO 12
<211> LENGTH: 502

<212> TYPE: PRT
<213> ORGANISM: Unknown
<220> FEATURE:
<223> OTHER INFORMATION: synthetic GALS Bdi_Bradi1g42560.1,
    glycosyltransferase family 92 (GT92) member,
    galactan synthase, beta-1,4,galactan synthase,
    beta-1,4 galactosyltransferase (GALS)

<400> SEQUENCE: 12

```
Met Lys Pro Ala Val Lys Lys Asp Ala Gly Val Gly Gly Gly Ala
1               5                   10                  15

Phe Gly Ile Ser Cys Leu Asp Ile Lys Ser Phe Ala Ala Ser Leu Ala
                20                  25                  30

Leu Leu Thr Leu Ile Met Ala Leu Trp Gln Leu His Pro Cys Gln Pro
            35                  40                  45

Leu Leu Ala Ile Thr Arg Ser Pro Ser Cys Pro Ile Leu Pro Leu Ser
        50                  55                  60

His Thr Thr Asn Ala Thr Ala Ala Leu Pro Ser Ser Thr Thr Lys Leu
65                  70                  75                  80

Pro Ser Ser Asn Phe Thr Thr Asp Arg Ala Pro Pro Thr Ala Ala Ala
                85                  90                  95

Ala Arg Pro Ala Pro Leu Arg Asp Pro Asn Lys Arg Glu Leu Arg Pro
            100                 105                 110

Tyr Gly Ser Ala Ala Ala Leu Phe Val Gln Met Gly Ala Tyr Arg Gly
        115                 120                 125

Gly Pro Arg Thr Phe Ala Val Val Gly Leu Ala Ser Lys Pro Ala Phe
    130                 135                 140

Val Phe Asn Thr Pro Tyr Phe Lys Cys Glu Trp Val Pro Asn Pro Gly
145                 150                 155                 160

Ala Gly Glu Pro Val Arg Thr Lys Ala Tyr Lys Met Leu Pro Asp Trp
                165                 170                 175

Gly Tyr Gly Arg Val Tyr Thr Val Val Val Asn Cys Thr Phe Pro
            180                 185                 190

Ser Asn Pro Asn Ala Gly Asn Arg Gly Gly Lys Leu Leu Val His Ala
        195                 200                 205

Tyr Tyr Ser Thr Lys Ser Arg Arg Tyr Glu Arg Phe Leu Ala Leu Glu
    210                 215                 220

Glu Ala Pro Gly Ser Tyr Asp Glu Ser Arg Phe Arg Pro Pro Phe Pro
225                 230                 235                 240

Tyr Glu Tyr Leu Tyr Cys Gly Ser Ser Leu Tyr Gly Asn Leu Ser Ala
                245                 250                 255

Pro Arg Leu Arg Glu Trp Leu Ala Tyr His Ala Arg Phe Phe Gly Pro
            260                 265                 270

Arg Ser His Phe Val Leu His Asp Ala Gly Gly Val Ser Pro Glu Val
        275                 280                 285

Arg Ala Val Leu Asp Pro Trp Val Arg Ala Gly Arg Val Thr Val Gln
    290                 295                 300

Asp Ile Arg Ala Gln Ala Glu Tyr Asp Gly Tyr Tyr Asn Gln Phe
305                 310                 315                 320

Leu Val Val Asn Asp Cys Leu His Arg Tyr Arg His Ala Ala Asn Trp
                325                 330                 335

Thr Phe Phe Phe Asp Val Asp Glu Tyr Met Tyr Leu Pro Asp Gly Arg
            340                 345                 350

Thr Leu Glu Glu Val Leu Gly Gln Leu Gln Arg Tyr Thr Gln Phe Thr
        355                 360                 365
```

```
Ile Glu Gln Asn Pro Met Ser Ser Lys Leu Cys Leu Glu Asp Pro Ala
370                 375                 380

Lys Glu Tyr Ser Arg Lys Trp Gly Phe Glu Lys Leu Val Phe Arg Asn
385                 390                 395                 400

Ser Ile Thr Gly Val Arg Arg Asp Arg Lys Tyr Ala Val Gln Ala Arg
            405                 410                 415

Asn Ala Tyr Ser Ala Gly Val His Met Ser Gln Asn Val Tyr Gly Arg
            420                 425                 430

Thr Thr His Arg Thr Glu Ser Leu Ile Arg Tyr Tyr His Tyr His Asn
        435                 440                 445

Thr Ile Asn Val Met Gly Glu Pro Cys Arg Glu Phe Val Ser Lys Pro
450                 455                 460

Thr Asn Gly Ser Lys Val Thr Phe Glu Gly Ile Pro Tyr Val Tyr Asp
465                 470                 475                 480

Asp Asn Met Lys Arg Leu Ala Gly Asp Ile Lys His Phe Glu Glu Ala
            485                 490                 495

Thr Val Gly Pro Thr Ser
            500

<210> SEQ ID NO 13
<211> LENGTH: 521
<212> TYPE: PRT
<213> ORGANISM: Unknown
<220> FEATURE:
<223> OTHER INFORMATION: synthetic GALS Osa_LOC_Os06g22330.1,
      glycosyltransferase family 92 (GT92) member,
      galactan synthase, beta-1,4,galactan synthase,
      beta-1,4 galactosyltransferase (GALS)

<400> SEQUENCE: 13

Met Lys Pro Ala Gly Gly Arg Ser Lys Asp Gly Gly Gly Gly Gly Ala
1               5                   10                  15

Ala Leu Leu Gly Gly Gly Gly Val Thr Cys Phe Asp Val Lys Ser Phe
            20                  25                  30

Val Ala Ser Leu Ala Leu Leu Thr Leu Ile Met Ala Leu Trp Gln Leu
        35                  40                  45

His Pro Tyr Gln Pro Leu Val Leu Leu Pro Ala Ala Leu Ser Ser Ser
    50                  55                  60

Pro Cys Pro Leu Leu Pro Arg Ser Pro Thr Ser Gly Ile Ala Val Ser
65                  70                  75                  80

Phe Leu Ser Thr Ala Ala Ala Thr Asn Ser Thr Asp Thr Ala Thr Val
                85                  90                  95

Pro Thr Thr Thr Ala Ala Ala Arg Val Ala Ala Thr Thr Arg Pro Thr
            100                 105                 110

Leu Pro Ala Arg Gln Arg Glu Arg Asp Pro Asn Lys Arg Glu Leu Arg
        115                 120                 125

Pro Tyr Gly Thr Ala Ala Leu Phe Val Gln Met Gly Ala Tyr Arg
130                 135                 140

Gly Gly Pro Arg Thr Phe Ala Val Val Gly Leu Ala Ser Lys Pro Ala
145                 150                 155                 160

His Val Phe Ser Asn Pro Tyr Phe Lys Cys Glu Trp Leu Pro Asn Ala
                165                 170                 175

Pro Ala Gly Ala Pro Pro Val Arg Thr Lys Ala Tyr Lys Met Leu Pro
            180                 185                 190

Asp Trp Gly Tyr Gly Arg Val Tyr Thr Val Val Val Asn Cys Thr
        195                 200                 205
```

Phe Pro Ser Asn Pro Asn Ala Asp Asn Leu Gly Gly Lys Leu Leu Val
    210                 215                 220

His Ala Tyr Tyr Ser Thr Ala Ser Arg Arg Tyr Glu Arg Phe Val Ala
225                 230                 235                 240

Leu Glu Glu Ala Pro Gly Ser Tyr Asp Asp Ala Arg Phe Arg Pro Pro
            245                 250                 255

Phe Ala Tyr Asp Tyr Leu Tyr Cys Gly Ser Ser Leu Tyr Gly Asn Leu
        260                 265                 270

Ser Ser Ala Arg Met Arg Glu Trp Leu Ala Tyr His Ala Arg Phe Phe
    275                 280                 285

Gly Pro Arg Ser His Phe Val Leu His Asp Ala Gly Val Thr Pro
290                 295                 300

Glu Val Arg Ala Val Leu Asp Pro Trp Val Ser Ala Gly Arg Val Thr
305                 310                 315                 320

Val Gln Asp Ile Arg Ala Gln Glu Asp Tyr Asp Gly Tyr Tyr Tyr Asn
                325                 330                 335

Gln Phe Leu Val Val Asn Asp Cys Leu His Arg Tyr Arg His Ala Ala
        340                 345                 350

Asn Trp Thr Phe Phe Phe Asp Val Asp Glu Tyr Ile Tyr Leu Pro Asp
    355                 360                 365

Gly Arg Ala Leu Glu Asp Val Leu Ala Gln Leu Gln Pro Tyr Thr Gln
370                 375                 380

Phe Thr Ile Glu Gln Asn Pro Met Ser Ser Lys Leu Cys Ile Asp Asp
385                 390                 395                 400

Pro Thr Glu Asp Tyr Ser Arg Glu Trp Gly Phe Glu Lys Leu Val Phe
            405                 410                 415

Arg Asn Ser Ile Thr Gly Val Arg Arg Asp Arg Lys Tyr Ala Ile Gln
        420                 425                 430

Ala Arg Asn Ala Tyr Ser Thr Gly Val His Met Ser Gln Asn Val Tyr
    435                 440                 445

Gly Arg Thr Thr His Lys Thr Glu Ser Leu Ile Arg Tyr Tyr His Tyr
450                 455                 460

His Asn Ser Ile Asn Val Met Gly Glu Pro Cys Arg Lys Phe Val Pro
465                 470                 475                 480

Lys Pro Ala Asn Gly Ser Lys Val Met Phe Glu Gly Ile Pro Tyr Val
            485                 490                 495

Tyr Asp Asp Asn Met Lys Arg Leu Ala Gly Glu Ile Arg Arg Phe Glu
        500                 505                 510

Lys Gln Thr Ile Gly Asp Val His Thr
    515                 520

<210> SEQ ID NO 14
<211> LENGTH: 509
<212> TYPE: PRT
<213> ORGANISM: Unknown
<220> FEATURE:
<223> OTHER INFORMATION: synthetic GALS Sbi_Sb10g024570.1,
      glycosyltransferase family 92 (GT92) member,
      galactan synthase, beta-1,4,galactan synthase,
      beta-1,4 galactosyltransferase (GALS)

<400> SEQUENCE: 14

Met Arg Lys Asp Ala Ala Pro Ala Gly Ile Ala Pro Gly Ser Ala Pro
1               5                   10                  15

Ala Leu Leu Cys Phe Asp Leu Lys Pro Phe Leu Ala Ala Leu Thr Val
            20                  25                  30

```
Leu Thr Leu Leu Ala Ala Ala Trp Gln Leu Arg Ala Tyr His Ser Val
         35                  40                  45

Leu Ala Ser Pro Phe Ser Ala Ala Cys Pro Gln Pro Thr Ala Ala Gly
 50                  55                  60

Ala Ser Leu Pro Arg Ala Leu Ala Val His Ala Asn Lys Ala Ser Pro
 65                  70                  75                  80

Ser Ser Ser Ala Ala Ala Ala Thr Asn Ser Thr Ala Ser Ser Ser Ser
                 85                  90                  95

Ala Pro Pro Gly Pro Glu Arg Arg Glu Phe Arg Ala Val Gly Ser
                100                 105                 110

Ala Ala Ala Leu Phe Val Gln Met Gly Ala Tyr Arg Gly Gly Pro Tyr
            115                 120                 125

Thr Phe Ala Val Val Gly Leu Ala Ser Lys Pro Thr His Val Tyr Gly
        130                 135                 140

Lys Pro Trp Phe Arg Cys Glu Trp Glu Pro Asn Gly Ala Ser Ser Ser
145                 150                 155                 160

Ser Pro Pro Met Arg Ala Ala Lys Thr Tyr His Met Leu Pro Asp Trp
                165                 170                 175

Gly Tyr Gly Arg Val Tyr Thr Val Val Val Asn Cys Thr Phe Pro
                180                 185                 190

Arg Val Pro Asn Ala Asp Asn Ala Gly Gly Arg Leu Ile Leu Tyr Ala
            195                 200                 205

His Tyr Gly Pro Ser Arg Ser Pro Ala Ser Arg His Glu Arg Ile Val
        210                 215                 220

Ala Leu Glu Glu Ser Pro Gly Ala Tyr Asp Glu Ala Ala Phe Arg Thr
225                 230                 235                 240

Thr Pro Pro Gln His Arg Tyr Asp Tyr Leu Tyr Cys Gly Ser Ser Leu
                245                 250                 255

Tyr Gly Asn Leu Ser Ala Ala Arg Val Arg Glu Trp Met Ala Tyr His
                260                 265                 270

Ala Arg Phe Phe Gly Ala Arg Ser His Phe Val Phe His Asp Ala Gly
            275                 280                 285

Gly Val Ser Pro Ala Val Arg Ala Ala Leu Gln Pro Trp Val Arg Ala
        290                 295                 300

Gly Arg Ala Thr Leu Gln Asp Val Arg Ala Gln Ala Glu Tyr Asp Gly
305                 310                 315                 320

Trp Tyr Tyr Asn Gln Phe Leu Val Val Asn Asp Cys Leu His Arg Tyr
                325                 330                 335

Arg His Ala Ala Lys Trp Thr Phe Phe Phe Asp Val Asp Glu Tyr Ile
            340                 345                 350

Phe Leu Pro Asp Gly Arg Ser Leu Glu Asp Val Leu Ala Glu Leu Glu
        355                 360                 365

Pro Tyr Thr Gln Phe Thr Ile Glu Gln Asn Pro Met Ser Ser Lys Leu
    370                 375                 380

Cys Val Asp Asp Pro Glu Ala Asp Tyr Ser Asn Gln Trp Gly Phe Glu
385                 390                 395                 400

Lys Leu Val Phe Arg Asn Ser Ile Thr Gly Val Arg Arg Asp Arg Lys
                405                 410                 415

Tyr Ala Ile Gln Ala Lys Asn Ala Tyr Ala Thr Gly Val His Met Ser
            420                 425                 430

Glu Asn Val Ile Gly Asn Thr Thr His Lys Thr Glu His Leu Ile Arg
        435                 440                 445

Tyr Tyr His Tyr His Asn Thr Ile Asn Val Leu Gly Glu Val Cys Arg
```

```
                450             455             460
Glu Phe Val Ser Val Pro Pro Lys Gly Gly Leu Thr Trp Ser Glu Lys
465                 470                 475                 480

Thr Pro Trp Tyr Tyr Asp Asn Ser Met Lys Arg Val Ala Asp Ala Val
                    485                 490                 495

Arg Glu Phe Glu Arg Glu Thr Ile Gly Asp Val Arg Leu
                500                 505

<210> SEQ ID NO 15
<211> LENGTH: 501
<212> TYPE: PRT
<213> ORGANISM: Unknown
<220> FEATURE:
<223> OTHER INFORMATION: synthetic GALS Zma_GRMZM2G121621_T01,
      glycosyltransferase family 92 (GT92) member,
      galactan synthase, beta-1,4,galactan synthase,
      beta-1,4 galactosyltransferase (GALS)

<400> SEQUENCE: 15

Met Arg Lys Asp Ala Ala Ala Gly Ile Ala Pro Gly Ser Ala Pro
1               5                   10                  15

Ala Phe Leu Cys Phe Asp Leu Lys Pro Phe Leu Ala Ala Leu Thr Val
                20                  25                  30

Leu Thr Leu Leu Ala Ala Ala Trp Gln Leu Arg Pro Tyr Gln Ser Leu
            35                  40                  45

Leu Ala Ser Pro Phe Ser Ala Cys Pro Gln Pro Thr Ala Gly Val
        50                  55                  60

Ser Leu Pro Arg Ala Leu Ala Val His Ala Lys Lys Ala Ser Ser Ala
65                  70                  75                  80

Thr Asn Ser Thr Val Ser Ser Ser Pro Ser Pro Pro Gly Pro Glu
                85                  90                  95

Arg Arg Glu Phe His Ala Val Gly Ser Ala Ala Ala Leu Phe Val Gln
                100                 105                 110

Met Gly Ala Tyr Arg Gly Gly Pro Tyr Thr Phe Ala Val Val Gly Leu
            115                 120                 125

Ala Ser Lys Pro Thr His Val Tyr Gly Lys Pro Trp Phe Arg Cys Glu
130                 135                 140

Trp Glu Pro Ser Asp Ala Ser Ser Pro Pro Met Arg Ala Ala Lys Thr
145                 150                 155                 160

Tyr His Met Leu Pro Asp Trp Gly Tyr Gly Arg Val Tyr Thr Val Val
                165                 170                 175

Val Val Asn Cys Thr Phe Pro Arg Val Pro Asn Ala Asp Ser Ala Gly
            180                 185                 190

Gly Arg Leu Val Leu Tyr Ala His Tyr Gly Pro Ser Arg Ser Pro Ala
        195                 200                 205

Ser Arg Arg Glu Arg Ile Val Ala Leu Glu Glu Ser Pro Gly Ala Tyr
210                 215                 220

Asp Glu Ala Ala Phe Arg Thr Thr Pro Pro His Arg Tyr Asp Tyr Leu
225                 230                 235                 240

Tyr Cys Gly Ser Ser Leu Tyr Gly Asn Leu Ser Ala Ala Arg Val Arg
                245                 250                 255

Glu Trp Met Ala Tyr His Ala Arg Phe Phe Gly Ala Arg Ser His Phe
            260                 265                 270

Val Phe His Asp Ala Gly Gly Val Gly Pro Ala Val Arg Ala Ala Leu
        275                 280                 285

Glu Pro Trp Val Arg Ala Gly Arg Ala Thr Leu Gln Asp Val Arg Ala
```

```
            290                 295                 300
Gln Ala Glu Tyr Asp Gly Trp Tyr His Asn Gln Phe Leu Val Val Asn
305                 310                 315                 320

Asp Cys Leu His Arg Tyr Arg His Ala Ala Lys Trp Thr Phe Phe Phe
                325                 330                 335

Asp Val Asp Glu Tyr Met Phe Leu Pro Asp Gly Arg Ala Leu Glu Asp
            340                 345                 350

Val Leu Ala Glu Leu Glu Pro Tyr Thr Gln Phe Thr Ile Glu Gln Asn
        355                 360                 365

Pro Met Ser Ser Lys Leu Cys Val Asp Pro Ala Ala Asp Tyr Ser
    370                 375                 380

Asn Gln Trp Gly Phe Glu Lys Leu Val Phe Arg Asn Ser Ile Thr Gly
385                 390                 395                 400

Val Arg Arg Asp Arg Lys Tyr Ala Ile Gln Ala Lys Asn Ala Tyr Ala
                405                 410                 415

Thr Gly Val His Met Ser Glu Asn Val Ile Gly Asn Thr Thr His Lys
            420                 425                 430

Thr Glu His Leu Ile Arg Tyr Tyr His Tyr His Asn Thr Ile Asn Val
        435                 440                 445

Leu Gly Glu Val Cys Arg Glu Phe Val Ser Val Pro Pro Lys Lys Gly
    450                 455                 460

Gly Gly Leu Thr Trp Ser Glu Lys Thr Pro Trp Tyr Tyr Asp Gly Ser
465                 470                 475                 480

Met Lys Arg Val Ala Gly Ala Val Arg Glu Phe Glu Arg Glu Thr Ile
                485                 490                 495

Gly Asp Val Arg Leu
            500

<210> SEQ ID NO 16
<211> LENGTH: 512
<212> TYPE: PRT
<213> ORGANISM: Unknown
<220> FEATURE:
<223> OTHER INFORMATION: synthetic GALS Sit_Si006264m,
      glycosyltransferase family 92 (GT92) member, galactan synthase,
      beta-1,4,galactan synthase, beta-1,4
      galactosyltransferase (GALS)

<400> SEQUENCE: 16

Met Arg Lys Asp Ala Ala Gly Gly Gly Ile Ala Pro Gly Ala Ala Ala
1               5                   10                  15

Pro Ala Leu Leu Cys Phe Asp Val Lys Pro Phe Leu Ala Ala Leu Thr
            20                  25                  30

Val Leu Thr Leu Leu Ala Ala Trp Gln Leu Arg Pro Tyr His Ser
        35                  40                  45

Leu Leu Ala Ser Pro Phe Pro Ala Ala Cys Ala Gln Ala Ala Ala Gly
    50                  55                  60

Thr Leu Pro Arg Ala Leu Ala Val His Ala Lys Lys Ser Ser Ser Ser
65                  70                  75                  80

Ser Ser Thr Pro Asn Tyr Thr Ala Ser Ser Ser Leu Pro Pro Pro
                85                  90                  95

Pro Pro Gly Pro Glu Arg Arg Glu Phe Arg Ala Val Gly Ser Ala Ala
            100                 105                 110

Ala Leu Phe Val Gln Met Gly Ala Tyr Arg Gly Gly Pro Tyr Thr Phe
        115                 120                 125

Ala Val Val Gly Leu Ala Ser Lys Pro Thr His Val Tyr Gly Lys Pro
```

```
             130                 135                 140
Trp Phe Arg Cys Glu Trp Glu Pro Thr Ile Pro Ser Asn Thr Asn Ala
145                 150                 155                 160

Ser Ser Pro Pro Glu Pro Met Arg Ala Ala Gly Thr Tyr His Met Leu
                165                 170                 175

Pro Asp Trp Gly Tyr Gly Arg Val Tyr Thr Val Val Val Asn Cys
            180                 185                 190

Thr Phe Pro Arg Val Pro Asn Ala Asp Asn Ala Gly Gly Arg Leu Val
                195                 200                 205

Leu Tyr Ala His His Gly Gly Pro Ser Arg Ser Pro Ser Ser Pro His
210                 215                 220

Glu Arg Ile Val Ala Leu Glu Glu Ala Pro Gly Ala Tyr Asp Glu Ala
225                 230                 235                 240

Ala Phe Arg Pro Gly Ala Pro His Arg Tyr Asp Tyr Leu Tyr Cys Gly
                245                 250                 255

Ser Ser Leu Tyr Gly Asp Leu Ser Ala Ala Arg Val Arg Glu Trp Met
                260                 265                 270

Ala Tyr His Ala Arg Phe Phe Gly Asp Arg Ser His Phe Val Phe His
            275                 280                 285

Asp Ala Gly Gly Val Gly Pro Ala Val Arg Ala Ala Leu Glu Pro Trp
290                 295                 300

Val Arg Ala Gly Arg Ala Thr Leu Gln Asp Val Arg Ala Gln Ala Glu
305                 310                 315                 320

Tyr Asp Gly Trp Tyr Tyr Asn Gln Phe Leu Val Val Asn Asp Cys Leu
                325                 330                 335

His Arg Tyr Arg His Ala Ala Lys Trp Thr Phe Phe Phe Asp Val Asp
                340                 345                 350

Glu Tyr Ile Phe Leu Pro Asp Gly Arg Lys Leu Glu Asp Val Leu Ala
            355                 360                 365

Glu Leu Glu Pro Tyr Thr Gln Phe Thr Ile Glu Gln Asn Pro Met Ser
370                 375                 380

Ser Arg Leu Cys Val Asp Asp Pro Glu Ala Asp Tyr Ser Asn Gln Trp
385                 390                 395                 400

Gly Phe Glu Lys Leu Val Phe Arg Asn Ser Ile Thr Gly Val Arg Arg
                405                 410                 415

Asp Arg Lys Tyr Ala Ile Gln Ala Lys Asn Ala Tyr Ala Thr Gly Val
                420                 425                 430

His Met Ser Glu Asn Val Ile Gly Asn Thr Thr His Lys Thr Glu His
            435                 440                 445

Leu Ile Arg Tyr Tyr His Tyr His Asn Thr Ile Asn Val Leu Asp Glu
450                 455                 460

Val Cys Arg Glu Phe Val Pro Ile Pro Pro Lys Gly Gly Leu Thr Trp
465                 470                 475                 480

Ser Glu Lys Thr Pro Trp Tyr Tyr Asp Asp Ser Met Lys Arg Val Ala
                485                 490                 495

Asn Ala Val Arg Glu Phe Glu Arg Glu Thr Ile Gly Asp Val Arg Leu
                500                 505                 510
```

<210> SEQ ID NO 17
<211> LENGTH: 508
<212> TYPE: PRT
<213> ORGANISM: Unknown
<220> FEATURE:
<223> OTHER INFORMATION: synthetic GALS Bdi_Bradi1g35710.1,
      glycosyltransferase family 92 (GT92) member, galactan synthase, beta-1,4,galactan synthase,
beta-1,4 galactosyltransferase (GALS)

<400> SEQUENCE: 17

```
Met Arg Lys Glu Ser Thr Gly Gly Gly Gly Ile Ala Ala Ala Ser
1               5                   10                  15

Pro Pro Pro Ala Leu Leu Cys Phe Asp Leu Lys Pro Phe Leu Ala Ala
            20                  25                  30

Leu Thr Val Val Thr Leu Leu Thr Ala Ala Trp Gln Leu Arg Pro Tyr
        35                  40                  45

Tyr Gln Tyr His Ser Ile Leu Ala Ser Ser Pro Phe Pro Ala Cys Pro
    50                  55                  60

Asp Pro Pro Ala Ser Ser Ser Pro Pro Arg Leu Leu Ala Ile Asp Gly
65                  70                  75                  80

Lys Ala Ser Lys Ser Asn Ala Ser Ser Ser Ser Pro Leu Pro Lys
                85                  90                  95

Gln Asp Glu Arg Arg Ala Ala Pro Asp Pro Asn Arg Arg Glu Phe Arg
            100                 105                 110

Ala Val Gly Ser Ala Ala Ala Leu Phe Val Gln Met Gly Ala Tyr Arg
        115                 120                 125

Gly Gly Pro Tyr Thr Phe Ala Val Val Gly Leu Ala Ser Lys Pro Thr
    130                 135                 140

His Val Tyr Gly Lys Pro Trp Phe Arg Cys Glu Trp Val Pro Asn Asn
145                 150                 155                 160

Ala Ser Gln Pro Thr Arg Ala Gly Lys Ala Tyr His Met Leu Pro Asp
                165                 170                 175

Trp Gly Tyr Gly Arg Val Tyr Thr Val Val Val Asn Cys Thr Phe
            180                 185                 190

Ser Ser Phe Ala Pro Asn Ala Asp Asn Ala Gly Gly Lys Leu Leu Leu
        195                 200                 205

Asn Ala Tyr Tyr Gly Pro Ser Pro Ala Arg Tyr Glu Arg Ile Val Ala
    210                 215                 220

Leu Glu Glu Ala Pro Gly Ala Tyr Asp Ser Ala Ala Phe Ala Gln His
225                 230                 235                 240

Arg Tyr Asp Tyr Leu Tyr Cys Gly Ser Ser Leu Phe Gly Glu Leu Ser
                245                 250                 255

Ala Ala Arg Val Arg Glu Trp Met Ala Tyr His Ala Arg Phe Phe Gly
            260                 265                 270

Pro Arg Ser His Phe Val Phe His Asp Ala Gly Gly Val Thr Ser Pro
        275                 280                 285

Ala Val Arg Ala Ala Leu Glu Pro Trp Val Arg Ala Gly Arg Ala Thr
    290                 295                 300

Leu Gln Asp Val Arg Ala Gln Ala Glu Tyr Asp Gly Trp Tyr His Asn
305                 310                 315                 320

Gln Phe Leu Val Val Asn Asp Cys Leu His Arg Tyr Arg His Ala Ala
                325                 330                 335

Lys Trp Thr Phe Phe Phe Asp Val Asp Glu Tyr Ile Phe Ile Pro Gly
            340                 345                 350

Gly Arg Thr Leu Glu Ser Val Met Ala Glu Leu Glu Pro Tyr Thr Gln
        355                 360                 365

Phe Thr Ile Glu Gln Asn Pro Met Ser Ser Arg Leu Cys Ala Arg Asp
    370                 375                 380

Pro Gly Asp Pro Lys Ala Asp Tyr Ser Asn Gln Trp Gly Phe Glu Lys
385                 390                 395                 400
```

```
Leu Val Phe Arg Asn Ser Ile Thr Gly Val Arg Arg Asp Arg Lys Tyr
                405                 410                 415

Ala Ile Gln Ala Lys Asn Ala Tyr Ala Thr Gly Val His Met Ser Glu
            420                 425                 430

Asn Val Ile Gly Asn Thr Thr His Lys Thr Glu His Leu Ile Arg Tyr
            435                 440                 445

Tyr His Tyr His Asn Thr Ile Asn Val Leu Gly Glu Val Cys Arg Glu
        450                 455                 460

Phe Val Pro Val Pro Pro Lys Gly Gly Val Thr Trp Ser Glu Lys Thr
465                 470                 475                 480

Pro Trp Tyr Tyr Asp Asp Ser Met Lys Arg Val Ala Asn Ala Val Arg
                485                 490                 495

Glu Phe Glu Arg Asn Thr Ile Gly Asn Val Arg Val
                500                 505

<210> SEQ ID NO 18
<211> LENGTH: 522
<212> TYPE: PRT
<213> ORGANISM: Unknown
<220> FEATURE:
<223> OTHER INFORMATION: synthetic GALS Osa_LOC_Os06g41910.1,
      glycosyltransferase family 92 (GT92) member,
      galactan synthase, beta-1,4,galactan synthase,
      beta-1,4 galactosyltransferase (GALS)

<400> SEQUENCE: 18

Met Arg Lys Asp Ala Ala Gly Gly Gly Gly Gly Gly Gly Ile Ala
1               5                   10                  15

Ala Gly Pro Ala Pro Ala Leu Leu Cys Phe Asp Leu Lys Pro Phe Leu
            20                  25                  30

Ala Ala Leu Thr Val Leu Thr Leu Ile Thr Ala Ala Trp Gln Leu Arg
        35                  40                  45

Ser Tyr Ser Ser Val Leu Pro Ser Pro Phe Pro Val Cys Ala Asp Pro
    50                  55                  60

Ala Ala Leu Ser Pro Pro Arg Ala Leu Ala Val Arg Thr Val Ala Ser
65                  70                  75                  80

Ser Gly Asn Ala Ser Val Ser Ser Asp Pro Gly Gly Pro Pro Ala Ser
                85                  90                  95

Leu Pro Glu Val Gly Asn Lys Lys Pro Val Ala Ala Ala Ala Ala Ala
            100                 105                 110

Asp Pro Asn Arg Arg Glu Phe Arg Ala Val Gly Ser Ala Ala Ala Leu
        115                 120                 125

Phe Val Gln Met Gly Ala Tyr Arg Gly Gly Pro Tyr Thr Phe Ala Val
    130                 135                 140

Ile Gly Leu Ala Ser Lys Pro Thr His Val Tyr Gly Lys Pro Trp Phe
145                 150                 155                 160

Arg Cys Glu Trp Val Pro Asn Ala Asn Gly Ser Ala Ala Ala Ala Ala
                165                 170                 175

Ala Arg Pro Met Arg Ala Ala Asn Thr Tyr His Met Leu Pro Asp Trp
            180                 185                 190

Gly Tyr Gly Arg Val Tyr Thr Val Val Val Asn Cys Thr Phe Ala
        195                 200                 205

Arg Val Pro Asn Ala Asp Asn Ala Gly Gly Lys Leu Val Leu Asn Ala
    210                 215                 220

Tyr Tyr Gly Ala Ser Pro Ala Arg Tyr Glu Arg Ile Val Ala Met Glu
225                 230                 235                 240
```

```
Glu Ala Pro Gly Ala Tyr Asp Ala Ala Glu Phe Arg Pro Pro His Arg
                245                 250                 255

Tyr Asp Tyr Leu Tyr Cys Gly Ser Ser Leu Tyr Gly Asn Leu Ser Ala
            260                 265                 270

Ala Arg Val Arg Glu Trp Met Ala Tyr His Ala Arg Phe Phe Gly Leu
        275                 280                 285

Arg Ser His Phe Val Phe His Asp Ala Gly Val Ser Pro Ala Val
    290                 295                 300

Arg Ala Ala Leu Glu Pro Trp Val Arg Ala Gly Arg Ala Thr Leu Gln
305                 310                 315                 320

Asp Val Arg Ala Gln Ala Glu Tyr Asp Gly Trp Tyr Tyr Asn Gln Phe
                325                 330                 335

Leu Val Val Asn Asp Cys Leu His Arg Tyr His Ala Ala Arg Trp
            340                 345                 350

Thr Phe Phe Phe Asp Val Asp Glu Tyr Ile Phe Leu Pro Asp Gly Arg
        355                 360                 365

Ser Leu Glu Ala Val Leu Ala Glu Leu Glu Pro Tyr Thr Gln Phe Thr
    370                 375                 380

Ile Glu Gln Asn Pro Met Ser Ser Arg Leu Cys Ala Arg Asn Pro Asp
385                 390                 395                 400

Glu Pro Glu Thr Asp Tyr Ser Asn Glu Trp Gly Phe Glu Lys Leu Val
                405                 410                 415

Phe Arg Asn Ser Ile Thr Gly Val Arg Arg Asp Arg Lys Tyr Ala Ile
            420                 425                 430

Gln Ala Lys Asn Ala Tyr Ala Thr Gly Val His Met Ser Glu Asn Val
        435                 440                 445

Ile Gly Asn Thr Thr His Lys Thr Glu His Leu Ile Arg Tyr Tyr His
    450                 455                 460

Tyr His Asn Thr Ile Asn Val Ile Gly Glu Val Cys Arg Glu Phe Val
465                 470                 475                 480

Pro Ile Pro Pro Asn Gly Gly Leu Ile Trp Ser Lys Thr Pro Trp
                485                 490                 495

Tyr Tyr Asp Asp Ser Met Lys Arg Ile Ala Asp Thr Val Arg Glu Phe
            500                 505                 510

Glu Arg Lys Thr Ile Gly Asp Val Arg Val
        515                 520

<210> SEQ ID NO 19
<211> LENGTH: 487
<212> TYPE: PRT
<213> ORGANISM: Unknown
<220> FEATURE:
<223> OTHER INFORMATION: synthetic GALS Rco_30170.m014246,
      glycosyltransferase family 92 (GT92) member,
      galactan synthase, beta-1,4,galactan synthase,
      beta-1,4 galactosyltransferase (GALS)

<400> SEQUENCE: 19

Met Arg Lys Asp Cys Pro Pro Leu Ser Ser Val Thr Gly Gly Lys Leu
1               5                   10                  15

Pro Ser Cys Leu Glu Thr Lys Pro Leu Val Ala Thr Leu Leu Ala Leu
            20                  25                  30

Thr Leu Val Met Leu Leu Trp Asn Leu Pro Pro Tyr Tyr Gln Asn Leu
        35                  40                  45

Leu Ser Thr Thr Arg Pro Cys Ser Ala Pro Ala Ala Ala Ala Ala Leu
    50                  55                  60
```

```
Ala Ala Ser Asn Ala Ser Ser Leu Pro Ile Thr Ser Val Ser Glu Gln
 65                  70                  75                  80

Lys Tyr Ser Thr Gly Val Ser Asp Pro Asn Lys Arg Ile Phe Glu Ala
                 85                  90                  95

Tyr Gly Asn Ala Ala Leu Phe Val Lys Met Gly Ala Tyr Arg Gly
            100                 105                 110

Gly Pro Arg Thr Phe Ala Val Val Gly Leu Ala Ser Lys Pro Ile His
            115                 120                 125

Val Phe Gly Arg Pro Trp Tyr Lys Cys Glu Trp Ile Ser Asn Asn Gly
130                 135                 140

Ser Ser Met Arg Ala Lys Ala Tyr Lys Met Leu Pro Asp Trp Gly Tyr
145                 150                 155                 160

Gly Arg Val Tyr Thr Val Val Val Asn Cys Thr Phe Pro Leu Asn
                165                 170                 175

Pro Asn Arg Glu Asn Ala Gly Gly Lys Leu Ile Leu Asn Ala Tyr Tyr
            180                 185                 190

Gly Glu Ser Pro Arg Lys Tyr Glu Lys Ile Val Ala Leu Glu Glu Ala
            195                 200                 205

Pro Gly Ser Tyr Asn Asp Ser Asn Tyr His Pro Pro Tyr Gln Tyr Glu
            210                 215                 220

Tyr Leu Tyr Cys Gly Ser Ser Leu Tyr Gly Asn Leu Ser Ala Ala Arg
225                 230                 235                 240

Met Arg Glu Trp Met Ala Tyr His Ala Trp Phe Phe Gly Pro Ser Ser
                245                 250                 255

His Phe Val Phe His Asp Ala Gly Gly Val Ser Pro Gln Val Arg Ala
            260                 265                 270

Ala Leu Glu Pro Trp Val Arg Ala Gly Arg Ala Thr Val Gln Asp Ile
            275                 280                 285

Arg Gly Gln Ala Glu Phe Asp Gly Tyr Tyr Asn Gln Phe Leu Val
290                 295                 300

Val Asn Asp Cys Leu His Arg Tyr Arg His Ala Ala Asn Trp Thr Phe
305                 310                 315                 320

Tyr Phe Asp Val Asp Glu Tyr Ile Tyr Leu Pro Asp Gly Ser Thr Leu
                325                 330                 335

Gln Ser Val Leu Ala Glu Phe Ser Asp Tyr Thr Gln Phe Thr Ile Glu
            340                 345                 350

Gln Asn Pro Met Ser Ser Val Leu Cys Leu Asn Asp Ser Ser His Asp
            355                 360                 365

Tyr Pro Arg Glu Trp Gly Phe Glu Lys Leu Leu Phe Arg Glu Ser Arg
            370                 375                 380

Ser Gly Ile Arg Arg Asp Arg Lys Tyr Ala Ile Gln Ala Lys Asn Ala
385                 390                 395                 400

Phe Ala Thr Gly Val His Met Ser Glu Asn Val Val Gly Lys Thr Leu
                405                 410                 415

His Lys Thr Glu Thr Lys Ile Arg Tyr Tyr His Tyr His Asn Ser Ile
            420                 425                 430

Thr Val Gln Gly Glu Leu Cys Arg Gln Leu Leu Pro Ala Ser Ala Lys
            435                 440                 445

His Asn Val Thr Trp Tyr Asn Lys Leu Pro Tyr Val Tyr Asp Asp Asn
            450                 455                 460

Met Lys Lys Leu Val Thr Thr Ile Arg Asp Phe Glu Arg Asn Thr Ile
465                 470                 475                 480
```

Gly Asn Val Arg Gln Tyr Ser
            485

<210> SEQ ID NO 20
<211> LENGTH: 495
<212> TYPE: PRT
<213> ORGANISM: Unknown
<220> FEATURE:
<223> OTHER INFORMATION: synthetic GALS Ptr_POPTR_0005s28030.1,
      glycosyltransferase family 92 (GT92) member,
      galactan synthase, beta-1,4,galactan synthase,
      beta-1,4 galactosyltransferase (GALS)

<400> SEQUENCE: 20

Met Arg Lys Asp Cys Gln Pro Pro Ser Ser Gly Ala Thr Val Ser Lys
1               5                   10                  15

Leu Pro Ala Cys Phe Glu Thr Lys Pro Leu Val Ala Thr Leu Leu Ala
            20                  25                  30

Leu Thr Leu Val Met Leu Leu Trp Asn Leu Pro Pro Tyr Tyr Gln Asn
        35                  40                  45

Leu Leu Ser Thr Thr Thr Arg Pro Ser Cys Ser Ala Pro Glu Thr Thr
    50                  55                  60

Val Ser Ile Ser Asn Thr Ser Ser Ser Phe Thr Ser Thr Ser Leu Ser
65                  70                  75                  80

Asp Gln Lys Tyr Leu Ser Ser Ser Ser Ser Ser Ser Asn Ala Asp
                85                  90                  95

Pro Asn Lys Arg Ile Phe Gln Ala Tyr Gly Asn Ala Ala Ala Leu Phe
            100                 105                 110

Val Gln Met Gly Ala Tyr Arg Gly Gly Pro Thr Thr Phe Ala Val Val
        115                 120                 125

Gly Leu Ala Ser Lys Pro Ile His Val Phe Arg Leu Pro Trp Tyr Lys
    130                 135                 140

Cys Glu Trp Ile Ser Asn Asn Gly Ser Ser Ile Arg Ala Lys Ala Tyr
145                 150                 155                 160

Lys Met Leu Pro Asp Trp Gly Tyr Gly Arg Val Tyr Thr Val Val Val
                165                 170                 175

Val Asn Cys Thr Phe Pro Val Asn Pro Asn Gln Asp Asn Ala Gly Gly
            180                 185                 190

Arg Leu Met Leu Asn Ala Tyr Tyr Asp Glu Ser Gln Arg Lys Tyr Glu
        195                 200                 205

Lys Phe Met Ala Leu Glu Glu Leu Pro Gly Ser Tyr Asn Glu Ser Lys
    210                 215                 220

Phe Arg Pro Pro Tyr Gln Tyr Glu Tyr Leu Tyr Cys Gly Ser Ser Leu
225                 230                 235                 240

Tyr Gly Asn Leu Ser Ala Ser Arg Phe Arg Glu Trp Met Ala Tyr His
                245                 250                 255

Ala Trp Phe Phe Gly Pro Ser Ser His Phe Val Phe His Asp Ala Gly
            260                 265                 270

Gly Val Ser Pro Glu Val Arg Ala Ala Leu Asp Pro Trp Val Arg Ala
        275                 280                 285

Gly Arg Ala Thr Val Gln Asp Ile Arg Gly Gln Ala Glu Phe Asp Gly
    290                 295                 300

Tyr Tyr Tyr Asn Gln Phe Leu Val Val Asn Asp Cys Leu His Arg Tyr
305                 310                 315                 320

Arg Tyr Ser Ala Asn Trp Thr Pro Tyr Phe Asp Val Asp Glu Tyr Ile
                325                 330                 335

```
Tyr Leu Pro Glu Gly Asn Thr Leu Glu Ser Val Leu Lys Asp Phe Ser
            340                 345                 350

Asn Tyr Thr Gln Phe Thr Ile Glu Gln Asn Pro Met Ser Ser Ala Leu
        355                 360                 365

Cys Phe Asn Asp Ser Thr Gln Asp Tyr Pro Arg Gln Trp Gly Phe Glu
    370                 375                 380

Lys Leu Leu Phe Arg Glu Ser Arg Thr Gly Ile Arg Arg Asp Arg Lys
385                 390                 395                 400

Tyr Ala Ile Gln Ala Lys Asn Ala Tyr Ala Thr Gly Val His Met Ser
                405                 410                 415

Glu Asn Val Ile Gly Lys Thr Leu His Gln Thr Glu Thr Lys Ile Arg
            420                 425                 430

Tyr Tyr His Tyr His Asn Ser Ile Gln Val Pro Gly Glu Leu Cys Arg
        435                 440                 445

Glu Phe Leu Pro Leu Ser Ala Lys Asn Asn Val Thr Trp Tyr Asn Gly
    450                 455                 460

Leu Pro Tyr Val Tyr Asp Asp Asn Met Lys Lys Leu Ala Ser Thr Ile
465                 470                 475                 480

Lys Asp Phe Glu Arg Asn Thr Ile Gly Asn Val Gln Ala Tyr Ser
                485                 490                 495

<210> SEQ ID NO 21
<211> LENGTH: 448
<212> TYPE: PRT
<213> ORGANISM: Unknown
<220> FEATURE:
<223> OTHER INFORMATION: synthetic GALS Mtr_CU179634_27.1,
      glycosyltransferase family 92 (GT92) member,
      galactan synthase, beta-1,4,galactan synthase,
      beta-1,4 galactosyltransferase (GALS)

<400> SEQUENCE: 21

Met Ala Lys Thr Pro Ser Asn Leu Val Val Thr Leu Leu Ala Phe Thr
1               5                   10                  15

Leu Val Met Leu Ile Trp Asn Leu Gln Pro Tyr Tyr Asp Thr Ile Leu
            20                  25                  30

Asn Pro Pro Ala Ser Ser Asn Ile Thr Asp Pro Asn Lys Arg Thr Phe
        35                  40                  45

Ile Thr Tyr Gly Asn Ala Ala Ser Leu Phe Val Gln Met Gly Ala Tyr
    50                  55                  60

Arg Gly Gly Pro Thr Thr Phe Ala Val Val Gly Leu Ala Ser Lys Pro
65                  70                  75                  80

Leu His Val Phe Gly Arg Pro Trp Tyr Lys Cys Glu Trp Ile Pro Asn
                85                  90                  95

Thr Asn Thr Asn Ser Ser Lys Ala Lys Ala Tyr Lys Ile Leu Pro Asp
            100                 105                 110

Trp Gly Tyr Gly Arg Val Tyr Thr Val Val Val Asn Cys Thr Phe
        115                 120                 125

Thr Val Asn Pro Asn Leu Asp Asn Asn Gly Gly Lys Leu Ile Leu Tyr
    130                 135                 140

Ala Tyr Tyr Ser Glu Ser Pro Lys Arg Tyr Glu Lys Ile Thr Ala Leu
145                 150                 155                 160

Glu Glu Ala Pro Gly Ser Tyr Asn Gln Ser Lys Phe Ser Pro Pro Tyr
                165                 170                 175

Thr Tyr Glu Tyr Leu Tyr Cys Gly Ser Ser Leu Tyr Gly Asn Leu Ser
            180                 185                 190
```

```
Ala Ser Arg Met Arg Glu Trp Met Ala Tyr His Ala Trp Phe Phe Gly
            195                 200                 205

Pro Ser Ser His Phe Val Phe His Asp Ala Gly Gly Val Ser Ser Glu
        210                 215                 220

Val Arg Ala Val Leu Glu Pro Trp Val Gln Ala Gly Arg Val Thr Leu
225                 230                 235                 240

Gln Asp Ile Arg Asp Gln Ser Glu Phe Asp Gly Tyr Tyr Asn Gln
                245                 250                 255

Phe Leu Val Val Asn Asp Cys Leu His Arg Tyr Arg His Ser Ala Tyr
            260                 265                 270

Trp Thr Phe Tyr Phe Asp Val Asp Glu Tyr Ile Tyr Leu Pro Asp Ala
        275                 280                 285

Asn Thr Thr Leu Glu Ser Val Leu Arg Asp Phe Ser Asn Asn Thr Gln
    290                 295                 300

Phe Thr Ile Glu Gln Asn Ala Met Ser Ser Ile Leu Cys Leu Asn Asn
305                 310                 315                 320

Ser Ser Gln Asn Tyr Ser Arg Leu Trp Gly Phe Glu Lys Leu Leu Phe
                325                 330                 335

Arg Asp Ser Arg Ser Asn Ile Arg Arg Asp Arg Lys Tyr Ala Ile Gln
            340                 345                 350

Ala Lys Asn Ala Tyr Ala Thr Gly Val His Met Ser Glu Asn Val Val
        355                 360                 365

Gly Gly Thr Leu His Gln Thr Glu Thr Lys Ile Arg Tyr Tyr His Tyr
    370                 375                 380

His Asn Ser Ile Thr Val His Glu Glu Leu Cys Arg Glu Phe Leu Pro
385                 390                 395                 400

Met Ser Ala Lys His Asn Ile Thr Trp Phe Asp Lys Val Pro Tyr Glu
                405                 410                 415

Tyr Asp Asp Ser Met Lys Lys Leu Thr Gln Thr Ile Lys Asp Phe Glu
            420                 425                 430

Arg Asn Thr Ile Asn Ile Asn Ala Ala Pro Asp His Thr Asn Asn Ser
        435                 440                 445

<210> SEQ ID NO 22
<211> LENGTH: 509
<212> TYPE: PRT
<213> ORGANISM: Unknown
<220> FEATURE:
<223> OTHER INFORMATION: synthetic GALS Aco_AcoGoldSmith_v1.003723m,
      glycosyltransferase family 92 (GT92) member,
      galactan synthase, beta-1,4,galactan synthase,
      beta-1,4 galactosyltransferase (GALS)

<400> SEQUENCE: 22

Met Phe Lys Thr Thr Pro Asn Ser Lys Thr Thr Leu Pro Leu His Leu
1               5                   10                  15

Ala Gly Lys Lys Pro Ile Met Arg Lys Asp Ser Pro Pro Pro Leu
            20                  25                  30

Ser Gly Gly Thr Thr Pro Gly Lys Ile Ser Leu Leu Cys Phe Glu Thr
        35                  40                  45

Lys Pro Ile Phe Ala Ile Leu Ala Leu Thr Leu Val Met Phe Ile
50                  55                  60

Trp Asn Ile Gln Pro Tyr Tyr Asp Asn Leu Leu Ser Thr Thr Arg Pro
65                  70                  75                  80

Cys Thr Ala Thr Pro Glu Lys Pro Lys Pro Leu Pro Leu Gln His Ser
                85                  90                  95
```

-continued

Thr Thr Ala Gln Lys Ile Ser Ala Leu Thr Gln Lys Pro Ala Asp Pro
            100                 105                 110

Asn Lys Arg Thr Phe Lys Thr Tyr Gly Asn Ala Ala Leu Phe Val
        115                 120                 125

Gln Met Gly Ala Tyr Arg Gly Gly Pro Asn Thr Phe Ala Ile Val Gly
    130                 135                 140

Leu Ala Ser Lys Pro Thr His Val Phe Gly Lys Ala Trp Tyr Lys Cys
145                 150                 155                 160

Glu Trp Ile Ser Asn Asn Gly Ser Ser Ile Lys Thr Lys Ala Tyr Lys
                165                 170                 175

Met Leu Pro Asp Trp Gly Tyr Gly Arg Val Tyr Thr Val Val Val
            180                 185                 190

Asn Cys Thr Phe Thr Val Asn Pro Asn Glu Asp Asn Ser Gly Gly Lys
            195                 200                 205

Leu Val Val Tyr Ala Tyr Gly Pro Ser Gln Lys Lys Tyr Glu Arg
        210                 215                 220

Ile Val Ala Leu Glu Glu Ala Gly Ser Tyr Asn Glu Leu Lys Tyr
225                 230                 235                 240

Lys Pro Pro Tyr Lys Tyr Asp Tyr Leu Tyr Cys Gly Ser Ser Leu Tyr
                245                 250                 255

Gly Asn Leu Ser Ala Val Arg Ile Arg Glu Trp Met Ala Tyr His Ala
            260                 265                 270

Trp Phe Phe Gly Lys Ser Ser His Phe Val Phe His Asp Ala Gly Gly
        275                 280                 285

Val Ser Ser Glu Val Arg Ala Val Leu Glu Pro Trp Val Lys Leu Gly
    290                 295                 300

Arg Val Thr Ile Gln Asp Ile Arg Asp Gln Ala Glu Phe Asp Gly Tyr
305                 310                 315                 320

Tyr Tyr Asn Gln Phe Leu Val Val Asn Asp Cys Leu His Arg Tyr Arg
                325                 330                 335

Asn Asp Ala Asn Trp Thr Phe Tyr Phe Asp Val Asp Glu Tyr Ile Tyr
            340                 345                 350

Leu Pro Asp Gly Asn Thr Leu Glu Ser Val Leu Asn Glu Phe Asn Asp
        355                 360                 365

Tyr Thr Gln Phe Thr Ile Glu Gln Asn Pro Met Ser Ser Lys Leu Cys
370                 375                 380

Leu Asn Glu Ser Thr His Asp Tyr Ser Ser Gln Trp Gly Phe Glu Lys
385                 390                 395                 400

Leu Val Phe Arg Asp Ser Arg Thr Lys Ile Arg Arg Asp Arg Lys Tyr
                405                 410                 415

Ala Ile Gln Ala Arg Asn Ala Tyr Ser Thr Gly Val His Met Ser Glu
            420                 425                 430

Asn Val Tyr Gly Lys Thr Leu His Lys Thr Glu Thr Lys Ile Arg Tyr
        435                 440                 445

Tyr His Tyr His Asn Thr Ile Thr Val Asp Gly Glu Pro Cys Arg Glu
        450                 455                 460

Phe Leu Pro Asp Ser Ala Lys Arg Thr Val Thr Met Ser Asp Asn Lys
465                 470                 475                 480

Pro Phe Val Tyr Asp Asp Lys Met Lys Lys Leu Ala Asp Thr Ile Lys
                485                 490                 495

Gln Phe Glu Lys Glu Thr Leu Gly Glu Ala Val His Val
            500                 505

<210> SEQ ID NO 23
<211> LENGTH: 441
<212> TYPE: PRT
<213> ORGANISM: Unknown
<220> FEATURE:
<223> OTHER INFORMATION: synthetic GALS Smo_77156, glycosyltransferase
family 92 (GT92) member, galactan synthase,
beta-1,4,galactan synthase, beta-1,4
galactosyltransferase (GALS)

<400> SEQUENCE: 23

Met Pro Ile Thr Gln Ser Cys Glu Asn Ser Ser Asn Leu Ser Val
1               5                   10                  15

Ser Thr Asn Phe Gly Pro Ala Ala Ile Asp Pro Ile Pro Ala Pro
            20                  25                  30

Glu Glu Gln Gly Thr Gly Ile His Ser Thr Val Arg His Leu His Pro
        35                  40                  45

Phe Gly Ile Ala Ser Tyr Thr Phe Val Leu Thr Gly Gly Tyr Arg Thr
    50                  55                  60

Gln Arg Arg Ser Phe Ala Val Val Gly Leu Ala Ala Lys Ser Leu His
65                  70                  75                  80

Val Phe Gly Lys Pro Asn Phe Ala Cys Glu Trp Val Pro Asp Ser Thr
            85                  90                  95

Thr Ser Asp Ser Pro Ser Ile Phe Gly Ser Ala Arg Lys Ile Leu Pro
            100                 105                 110

Asp Trp Gly Tyr Gly Arg Val Tyr Thr Val Val Val His Cys Tyr
        115                 120                 125

Phe Lys Ser Ser Val Gly Glu Asp Gly Ser Gly Gly Arg Leu Ile Leu
    130                 135                 140

His Ala Gly Glu Lys Gly Ser Pro Ser Pro Ser Lys Ile Thr Ala
145                 150                 155                 160

Leu Val Glu Ala Pro Gly Ser Tyr Ser Pro Ser Gln Phe Leu Pro Lys
            165                 170                 175

Tyr Asp Tyr Leu Tyr Cys Gly Ser Ser Leu Phe Gly Asp Val Asn Pro
            180                 185                 190

Gln Arg Leu Arg Glu Trp Ile Ala Tyr His Ala Trp Leu Phe Gly Pro
        195                 200                 205

Arg Ser His Phe Val Leu His Asp Ala Gly Gly Ala Arg Ser Lys Gly
    210                 215                 220

Val Arg Leu Val Leu Glu Pro Trp Val Arg Ser Gly Arg Val Thr Val
225                 230                 235                 240

Gln Asp Phe Arg Glu Gln Ala Arg Phe Asp Gly Tyr Tyr His Asn Gln
            245                 250                 255

Phe Leu Val Val Asn Asp Cys Leu Phe Arg Tyr Lys His Ala Ala Asn
            260                 265                 270

Trp Thr Phe Phe Phe Asp Val Asp Glu Tyr Val His Val Pro Gly Pro
        275                 280                 285

Ser Thr Leu Asp Ser Val Leu Asn Glu Leu Gly Gln Lys Tyr Ser Gln
    290                 295                 300

Ile Ile Phe Lys Gln Thr Pro Met Gly His Asn Val Cys Ile Asp Ser
305                 310                 315                 320

Asn Arg Thr Asn Leu Ser Arg Gln Trp Gly Phe Glu Lys Leu Val Phe
            325                 330                 335

Ile Asn Val Gln Lys Ser Val Arg Leu Asp Arg Lys Tyr Val Leu Arg
            340                 345                 350

Ala Pro Leu Ala Asp Ser Ala Gly Val His Leu Ser Glu Asn Val Arg

```
              355                 360                 365
Gly Lys Ser Leu Tyr Ser Arg Gly Gln Ile Ser Tyr Phe His Phe His
        370                 375                 380

Asn Thr Ile Thr Glu His Gln Glu Asn Cys Arg Glu Phe Val Lys Val
385                 390                 395                 400

Pro Lys Asn Arg Thr Ser Lys Val Trp Leu Asn Lys Val Pro Tyr Leu
                405                 410                 415

Tyr Asp Asp Lys Leu Ser Thr Leu Ala Asp Glu Val Lys Gln Phe Glu
            420                 425                 430

Leu Gln Thr Ile Gly Pro Val Thr Leu
            435                 440

<210> SEQ ID NO 24
<211> LENGTH: 520
<212> TYPE: PRT
<213> ORGANISM: Unknown
<220> FEATURE:
<223> OTHER INFORMATION: synthetic GALS Rco_28563.m000093,
      glycosyltransferase family 92 (GT92) member,
      galactan synthase, beta-1,4,galactan synthase,
      beta-1,4 galactosyltransferase (GALS)

<400> SEQUENCE: 24

Met Gly Lys Glu Arg Glu Lys Glu Arg Gly Gly Gly Gly Gly Gly Gly
1               5                   10                  15

Asp Lys Lys Met Phe Ile Gly Val Val Met Asn Cys Ala Ala Glu Leu
            20                  25                  30

Lys Leu Leu Leu Thr Ala Leu Leu Ile Leu Cys Thr Ile Ala Thr Leu
        35                  40                  45

Leu Gln Phe Leu Pro Ser Arg Phe Thr Ile Ser Thr Ser Asp Leu Arg
    50                  55                  60

Phe Cys Ile Ser Arg Ile Thr Thr Thr Thr Thr Thr Thr Thr Thr Thr
65                  70                  75                  80

Thr Ser Ile Ala Leu Pro Leu Asn Ser Ser Val Ser Pro Gln Ser
                85                  90                  95

Ser Pro Pro Ser Ser Leu Gln Gln Pro Glu Glu Gln Leu Pro Pro Asn
            100                 105                 110

Gly Thr Val Lys Arg Ala Phe Tyr Pro His Gly Ala Ala Tyr Asn
        115                 120                 125

Phe Ile Ala Met Gly Ala Tyr Arg Gly Gly Phe Asp Thr Phe Ala Ile
    130                 135                 140

Val Gly Leu Ser Ser Lys Pro Leu His Leu Tyr Ala Lys Pro Thr Tyr
145                 150                 155                 160

Gln Cys Glu Trp Val Pro His Lys Asn Ser Ser Ser Gly Gly Ser Asp
                165                 170                 175

Pro Ile Thr Ala Val Ala Tyr Lys Ile Leu Pro Asp Trp Gly Tyr Gly
            180                 185                 190

Arg Val Tyr Thr Val Val Val Asn Cys Thr Phe Ala Gln Pro Ile
        195                 200                 205

Asn Ser Asp Asn Ser Gly Gly Lys Leu Phe Leu His Ala Ser Thr Ser
    210                 215                 220

Gly Gly Gly Asp Arg Asp Phe Asn Ile Thr Asp Arg Phe Glu Val Leu
225                 230                 235                 240

Gln Glu Pro Pro Gly Asn Leu Asn Ile Ser Leu Phe Thr Thr Lys Pro
                245                 250                 255

Lys Tyr Asp Tyr Leu Tyr Cys Gly Ser Ser Leu Tyr Gly Gly Leu Ser
```

```
                    260                 265                 270
Pro Gln Arg Val Arg Glu Trp Met Ala Tyr His Val Arg Leu Phe Gly
        275                 280                 285

Glu Arg Ser His Phe Val Ile His Asp Ala Gly Gly Val His Glu Glu
        290                 295                 300

Val Leu Glu Val Leu Lys Pro Trp Met Glu Leu Gly Tyr Val Thr Leu
305                 310                 315                 320

Gln Asp Ile Arg Asp Gln Glu Arg Phe Asp Gly Tyr Tyr His Asn Gln
                325                 330                 335

Phe Met Val Val Asn Asp Cys Leu His Arg Tyr Lys Phe Val Ala Lys
            340                 345                 350

Trp Ile Phe Phe Asp Val Asp Glu Tyr Ile Tyr Ile Pro Pro Lys
        355                 360                 365

Asn Thr Ile Lys Ser Val Leu Asp Ser Leu Ser Asp Tyr Asn Gln Phe
        370                 375                 380

Thr Phe Glu Gln Met Pro Met Ser Ser Lys Leu Cys Leu Ser Ala Asp
385                 390                 395                 400

Tyr Gly Arg Tyr Tyr Arg Lys Trp Gly Phe Glu Lys Leu Val Tyr Arg
                405                 410                 415

Asp Ile Lys Arg Gly Ile Arg Arg Asp Arg Lys Tyr Ala Ile Gln Pro
            420                 425                 430

Arg Asn Val Phe Ala Thr Gly Val His Met Ser Gln Asn Leu Ala Gly
        435                 440                 445

Lys Thr Asn His Lys Thr Glu Ser Lys Ile Lys Tyr Phe His Tyr His
        450                 455                 460

Gly Thr Ile Ala Gln Arg Arg Glu Pro Cys Arg Asn Leu Leu Asn Val
465                 470                 475                 480

Thr Glu Ile Asn Phe Glu Asn Asn Pro Tyr Val Leu Asp Thr Thr Met
                485                 490                 495

Arg Asp Ile Ala Trp Ser Val Lys Lys Phe Glu Gln Lys Met Ile Gly
            500                 505                 510

Ser Arg Leu Gln Ser Thr Arg Gln
        515                 520

<210> SEQ ID NO 25
<211> LENGTH: 515
<212> TYPE: PRT
<213> ORGANISM: Unknown
<220> FEATURE:
<223> OTHER INFORMATION: synthetic GALS Ptr_POPTR_0001s12330.1,
      glycosyltransferase family 92 (GT92) member,
      galactan synthase, beta-1,4,galactan synthase,
      beta-1,4 galactosyltransferase (GALS)

<400> SEQUENCE: 25

Met Gly Lys Glu Arg Ser Glu Lys Glu Arg Gly Gly Gly Glu His Asn
1               5                   10                  15

Lys Arg Asn Leu Phe Val Ser Cys Val Val Met Asn Ser Cys Ala Ala
            20                  25                  30

Glu Leu Lys Leu Leu Leu Thr Ala Leu Leu Val Ile Cys Ser Val Ala
        35                  40                  45

Thr Leu Phe Gln Ile Leu Pro Pro Arg Phe Thr Ile Ser Ala Ser Asp
    50                  55                  60

Leu Arg Phe Cys Ile Ser Arg Ile Ser Thr Ser Asn Thr Ser Ile Ala
65                  70                  75                  80

Ser Leu Asn Ser Thr Pro Thr Ser Thr Pro Thr Met Pro Pro Ser Pro
```

-continued

```
                85                  90                  95
Ser Pro Pro Ser Ile Arg Lys Asp Gln Val Ala Asp Asn Gly Val Ile
            100                 105                 110
Lys Arg Val Phe Asn Pro Tyr Gly Ser Ala Ala Tyr Asn Phe Ile Thr
            115                 120                 125
Met Gly Ala Tyr Arg Gly Gly Leu Asn Thr Phe Ala Ile Ile Gly Leu
            130                 135                 140
Ala Ser Lys Pro Leu His Val Tyr Ser Lys Pro Ala Tyr Gln Cys Glu
145                 150                 155                 160
Trp Val Pro Gln Ser Ser Ala Ser Asn Ser Thr Phe Ser Thr Val
                165                 170                 175
Ser Tyr Lys Met Leu Pro Asp Trp Gly Tyr Gly His Val Tyr Thr Val
                180                 185                 190
Val Val Val Asn Cys Thr Phe Ser Glu Ala Val Asn Ser Glu Asn Ser
                195                 200                 205
Gly Gly Lys Leu Phe Leu Glu Ala Ser Thr Ser Gly Gly Asp Arg
210                 215                 220
Asp Phe Asn Ile Thr Asp Arg Phe Glu Val Leu Asn Glu Ser Pro Gly
225                 230                 235                 240
Asp Ile Asn Thr Thr Leu Phe Ser Ser Lys Pro Lys Tyr Asp Tyr Leu
                245                 250                 255
Tyr Cys Gly Ser Ser Leu Tyr Gly Gly Leu Ser Pro Gln Arg Val Arg
            260                 265                 270
Glu Trp Ile Ala Tyr His Val Arg Leu Phe Gly Lys Arg Ser His Phe
            275                 280                 285
Val Ile His Asp Ala Gly Gly Val His Glu Glu Val Leu Glu Val Leu
            290                 295                 300
Lys Pro Trp Met Glu Leu Gly Tyr Val Thr Leu Gln Asp Ile Lys Glu
305                 310                 315                 320
Gln Glu Arg Phe Asp Gly Tyr Tyr His Asn Gln Phe Met Val Val Asn
                325                 330                 335
Asp Cys Leu His Arg Tyr Lys Phe Met Ala Lys Trp Met Phe Phe Phe
                340                 345                 350
Asp Val Asp Glu Tyr Ile His Val Pro Gln Lys Asn Thr Ile Lys Ser
            355                 360                 365
Val Leu Asp Ser Leu Ser Asp Tyr Thr Gln Phe Thr Ile Glu Gln Met
            370                 375                 380
Pro Met Asn Asn Lys Leu Cys Leu Ser Ala Asp Tyr Gly Arg Tyr Tyr
385                 390                 395                 400
Arg Lys Trp Gly Phe Glu Lys Leu Val Tyr Lys Asp Val Lys Arg Gly
                405                 410                 415
Ile Arg Arg Asp Arg Lys Tyr Ala Ile Gln Pro Arg Asn Val Phe Ala
            420                 425                 430
Thr Gly Val His Met Ser Gln Asn Val Ala Gly Lys Thr Thr His Lys
            435                 440                 445
Thr Glu Gly Met Ile Arg Tyr Phe His Tyr His Gly Thr Ala Ala Gln
450                 455                 460
Arg Arg Glu Pro Cys Arg Asn Leu Leu Asn Val Thr Glu Ile Asn Phe
465                 470                 475                 480
Glu Asn Asn Pro Tyr Val Leu Asp Thr Thr Met Arg Asp Leu Ala Trp
                485                 490                 495
Ser Val Lys Lys Phe Glu Asn Gln Met Ile Gly Pro Lys Leu Lys Asn
            500                 505                 510
```

Thr Arg Gln
        515

<210> SEQ ID NO 26
<211> LENGTH: 504
<212> TYPE: PRT
<213> ORGANISM: Unknown
<220> FEATURE:
<223> OTHER INFORMATION: synthetic GALS Mtr_Medtr8g084210.1,
      glycosyltransferase family 92 (GT92) member,
      galactan synthase, beta-1,4,galactan synthase,
      beta-1,4 galactosyltransferase (GALS)

<400> SEQUENCE: 26

```
Met Ala Ile Lys Asp Lys Glu Lys Lys Leu Phe Leu Trp Ser Ser Arg
1               5                   10                  15

Asn Tyr Ala Ala Glu His Lys Leu Phe Leu Thr Thr Leu Leu Leu Leu
            20                  25                  30

Cys Thr Ile Ala Thr Leu Phe Cys Phe Ile Pro Ser Ser Phe Thr Ile
        35                  40                  45

Ser Ala Ser Asp Leu Arg Leu Cys Ile Ser Arg Ile Ser Gln Thr Pro
    50                  55                  60

Pro Thr Pro Thr Ala Thr Pro Pro Ser Pro Ser Pro Pro Pro Pro Ser
65                  70                  75                  80

Ser Ile Val His Glu Lys Leu Ile Thr Asn Thr Asn Thr Thr Thr Ile
                85                  90                  95

Ile Lys Arg Phe Phe Asn Pro Tyr Gly Ser Ala Ala Tyr Asn Phe Ile
            100                 105                 110

Thr Met Ser Ala Tyr Arg Gly Gly Leu Asn Thr Phe Ala Ile Thr Gly
        115                 120                 125

Leu Ser Ser Lys Pro Leu His Val Tyr Gly Asn Pro Thr Tyr Glu Cys
    130                 135                 140

Glu Trp Ile Pro Asn Thr Asn Thr Asn Thr Asn Ser Ser Lys Asn Ile
145                 150                 155                 160

Thr Thr Ile Gly Tyr Lys Met Leu Pro Asp Trp Gly Tyr Gly His Val
                165                 170                 175

Tyr Thr Val Val Ile Val Asn Cys Thr Phe Asn Glu Ser Ile Asn Val
            180                 185                 190

Asp Asn Ser Gly Gly Lys Leu Met Leu Tyr Ala Ser Thr Ser Gly Gly
        195                 200                 205

Gly Asp Thr Lys Phe Asn Ile Thr Asp Arg Met Glu Val Leu Val Glu
    210                 215                 220

Gln Pro Lys Val Leu Asp Ile Thr Leu Phe Asn Ser Lys Pro Lys Leu
225                 230                 235                 240

Asp Tyr Phe Tyr Cys Gly Ser Ser Leu Phe Gly Asn Leu Asn Pro Gln
                245                 250                 255

Arg Val Arg Glu Trp Ile Ala Tyr His Val Arg Leu Phe Gly Pro Asn
            260                 265                 270

Ser His Phe Val Leu His Asp Ala Gly Gly Val His Glu Glu Val Phe
        275                 280                 285

Glu Val Leu Lys Pro Trp Ile Glu Leu Gly Tyr Val Thr Leu Gln Asp
    290                 295                 300

Ile Arg Asp Gln Glu Arg Phe Asp Gly Tyr Tyr His Asn Gln Phe Met
305                 310                 315                 320

Val Leu Asn Asp Cys Leu His Arg Tyr Lys Phe Met Ala Lys Trp Met
                325                 330                 335
```

```
Phe Phe Phe Asp Val Asp Glu Tyr Ile Tyr Val Pro Pro Lys Ser Thr
                340                 345                 350

Ile Lys Thr Val Leu Asp Ser Leu Ser Glu Tyr Ser Gln Phe Thr Ile
            355                 360                 365

Glu Gln Met Ala Met Ser Val Lys Val Cys Leu Ser His Asp Tyr Gly
        370                 375                 380

Lys Thr Tyr Arg Lys Trp Gly Phe Glu Lys Leu Val Tyr Arg Asp Ala
385                 390                 395                 400

Ile Thr Gly Ile Arg Arg Asp Arg Lys Tyr Ala Val Gln Pro Arg Ser
                405                 410                 415

Leu Phe Ala Asn Gly Ile His Met Ser Glu Asn Leu Asp Gly Lys Thr
            420                 425                 430

Thr His Asn Thr Glu Gly Arg Ile Lys Tyr Phe His Tyr His Gly Ala
        435                 440                 445

Ile Ser Gln Arg Arg Glu Thr Cys Lys Leu Leu Val Asn Ser Thr Lys
    450                 455                 460

Ile Thr Tyr Glu Lys Thr Pro Tyr Val Met Asp Thr Thr Leu Arg Asp
465                 470                 475                 480

Ile Ala Gly Ser Ile Lys Lys Phe Glu Leu Lys Met Ile Gly Thr Ser
                485                 490                 495

Val Tyr Gln Ser Asp Ile Ala Leu
            500
```

<210> SEQ ID NO 27
<211> LENGTH: 506
<212> TYPE: PRT
<213> ORGANISM: Unknown
<220> FEATURE:
<223> OTHER INFORMATION: synthetic GALS Aco_AcoGoldSmith_v1.003774m, glycosyltransferase family 92 (GT92) member, galactan synthase, beta-1,4,galactan synthase, beta-1,4 galactosyltransferase (GALS)

<400> SEQUENCE: 27

```
Met Val Lys Glu Lys Glu Lys Asp Gln Lys Glu Lys Asp Asn Lys Leu
1               5                   10                  15

Phe Val Gly Val Val Trp Asn Cys Ala Thr Glu Ile Lys Ile Leu Leu
            20                  25                  30

Thr Ala Leu Leu Phe Leu Ser Ser Leu Val Ile Ile Leu Gln Phe Leu
        35                  40                  45

Pro Ser Arg Phe Ser Leu Ser Ser Asp Leu Gln Leu Cys Leu Ser
    50                  55                  60

Lys Leu Ser Ser Ser Thr Ser Thr Ser Thr Ser Glu Val Pro Gln Val
65                  70                  75                  80

Ser Val Leu Ser Ser Ser Ser Pro Leu Ile Gln Lys Asp Gln Ile
            85                  90                  95

Ile Gln Gln Gly Ile Ile Lys Arg Ala Phe Asn Ser Tyr Gly Ser Ala
                100                 105                 110

Ala Tyr Ser Phe Ile Gln Met Gly Ser Tyr Arg Gly Gly Leu Asn Thr
            115                 120                 125

Phe Ala Ile Ile Gly Leu Ala Ser Lys Pro Leu Ile Val Tyr Gly Lys
        130                 135                 140

Pro Ser Tyr Gln Cys Gln Trp Ile Ser Asp Asp Arg Asn Asn
145                 150                 155                 160

Asn Asn Ile Thr Thr Phe Gly Ser Lys Ile Leu Pro Asp Trp Gly Tyr
                165                 170                 175
```

```
Gly Arg Val Tyr Thr Val Val Ile Asn Cys Thr Phe Pro Ile Pro
            180                 185                 190

Val Gly Ile Asn Gly Ser Gly Arg Leu Ile Leu His Ala Ser Asp
        195                 200                 205

Gly Gly Ser Gly Asp Thr Asp Val Val Val Ser Thr Glu Lys Ile Glu
210                 215                 220

Ala Leu Val Glu Ala Pro Gly Ser Leu Asn Ala Ser Val Phe Ser Ser
225                 230                 235                 240

Pro Pro Val Tyr Asp Tyr Phe Tyr Cys Gly Ser Pro Leu Tyr Gly Asp
                245                 250                 255

Leu Ser Pro Gln Arg Val Arg Glu Trp Ile Ala Tyr His Val Lys Leu
            260                 265                 270

Phe Gly Glu Lys Ser His Phe Val Ile Tyr Asp Ala Gly Gly Ile His
        275                 280                 285

Ser Gly Val Leu Glu Val Leu Lys Pro Trp Ile Glu Lys Gly Tyr Val
    290                 295                 300

Thr Leu Gln Asp Val Arg Glu Gln Glu Arg Phe Asp Gly Tyr Tyr His
305                 310                 315                 320

Asn Gln Phe Leu Val Val Asn Asp Cys Leu His Arg Tyr Arg Phe Met
                325                 330                 335

Ala Lys Trp Met Phe Phe Phe Asp Val Asp Glu Tyr Ile Tyr Val Gln
            340                 345                 350

Pro Glu Ser Thr Ile Gln Ser Ile Val Asn Glu Tyr Ser Gly Tyr Thr
        355                 360                 365

Gln Phe Thr Ile Glu Gln Met Pro Met Ser Asn Lys Leu Cys Leu Ala
    370                 375                 380

Ser Asp Ala Gly Asn Thr Glu Arg Glu Trp Gly Phe Glu Lys Leu Val
385                 390                 395                 400

Tyr Arg Asn Val Gln Arg Gly Ile Arg Arg Asp Arg Lys Tyr Ala Ile
                405                 410                 415

Gln Pro Arg Asn Thr Phe Ala Thr Gly Val His Met Ser Gln Asn Val
            420                 425                 430

Ala Gly Arg Thr Leu His Arg Ile Asp Gly Arg Ile Lys Tyr Phe His
        435                 440                 445

Tyr His Gly Thr Ile Ser Glu Arg His Glu Leu Cys Arg Gln Leu Val
    450                 455                 460

Asn Glu Ser Gln Ile Tyr Ile Glu Lys Lys Pro Tyr Ile Leu Asp Thr
465                 470                 475                 480

Thr Leu Arg Asp Ala Ala Ala Val Lys Ser Phe Glu Ile Lys Ser
                485                 490                 495

Ile Gly Ser Gln Leu Gln Arg Thr Arg Gln
            500                 505

<210> SEQ ID NO 28
<211> LENGTH: 530
<212> TYPE: PRT
<213> ORGANISM: Unknown
<220> FEATURE:
<223> OTHER INFORMATION: synthetic GALS Ppa_Pp1s35_57V6.1,
      glycosyltransferase family 92 (GT92) member,
      galactan synthase, beta-1,4,galactan synthase,
      beta-1,4 galactosyltransferase (GALS)

<400> SEQUENCE: 28

Met Ala Arg Gln Trp Leu Arg Lys Ser Glu Leu Asn Glu Lys Leu Trp
1               5                   10                  15
```

Lys Gly Asp Lys Gly Glu Ser Leu Leu Asp Ser Ser Val Ala Gly Val
            20                  25                  30

Arg Thr Ala Leu Ser Ala Glu Ser Leu Ala Lys Ile Leu Leu Leu Val
        35                  40                  45

Val Val Asn Ser Val Phe Leu Leu Ala Ala Leu His Leu Leu Asn Ser
50                  55                  60

Lys Arg Glu Phe Asp Asn Arg Gly Asp Arg Ser Asn Cys Val Thr Asn
65                  70                  75                  80

Tyr Arg Leu Asn Asn Val His Pro Met Ser Leu Ser Leu Asp Gln Asn
                85                  90                  95

Arg Leu Ile Gln Ser Ser Glu Phe Ala Pro Lys Asn Glu Ser Asn Gln
            100                 105                 110

Glu Asn Ile Arg Gln Phe Asp Thr Phe Gly Val Ala Val His Leu Phe
            115                 120                 125

Ile Lys Met Ser Ala Tyr Arg Gly Gly Ser Asn Ser Phe Ala Ile Ile
        130                 135                 140

Gly Leu Glu Ala Lys Asn Pro Gly Glu Leu Tyr Asn Asp Pro Pro Tyr
145                 150                 155                 160

Glu Cys Val Trp Ile Pro Gly Pro Asp Ser Leu Val Trp Ala Pro Leu
                165                 170                 175

Lys Gly Ser Ala Ile Lys Met Leu Pro Asp Thr Gly Asn Val Tyr Ser
            180                 185                 190

Arg Leu Tyr Ser Ala Val Ile Ile Asn Cys Thr Phe Ser Gln Asp Val
        195                 200                 205

Gly Val Asp Arg Lys Gly Gly Gln Leu Val Leu Tyr Ala Ser Tyr Gly
        210                 215                 220

Asp Gln Tyr Pro Arg Asn Pro Glu Arg Ile Val Ala Leu Thr Glu Gln
225                 230                 235                 240

Pro Asp Glu Phe Pro Gly Val Glu Phe Tyr Glu Ser Ser Asp Met Lys
                245                 250                 255

Tyr Asp Tyr Val Tyr Cys Gly Ser Pro Leu Phe Gly Asn Leu Ser Pro
            260                 265                 270

Gln Lys Ile Arg Glu Trp Ile Ala Tyr His Ala His Phe Phe Gly Pro
        275                 280                 285

Arg Ser His Phe Phe Leu Tyr Asp Ala Gly Gly Val His Asp Asn Val
290                 295                 300

Arg Arg Met Ile Glu Pro Trp Ile Lys Ala Gly Arg Val Thr Leu Asp
305                 310                 315                 320

Asn Ile Arg Glu Gln Glu Lys Phe Asp Gly Tyr Tyr His Asn Gln Phe
            325                 330                 335

Met Val Val Asn Asp Cys Phe His Arg Ala Arg His Leu Ala Arg Trp
            340                 345                 350

Ile Phe Phe Phe Asp Val Asp Glu Phe Ile Trp Ala Pro Pro Asn Asp
        355                 360                 365

Asn Ser Leu Pro Ala Ile Leu Ala Arg Tyr Glu Asn Gln Ser Gln Ile
        370                 375                 380

Ile Ile Trp Gln Lys Pro Met Ser Lys Ser Leu Cys Ala Gln Glu Gln
385                 390                 395                 400

Gly Glu Ala Gly Asn Asp Ser Ser Phe Ser Arg Leu Arg Ser Lys Trp
            405                 410                 415

Thr Phe Glu Lys Leu Val Phe Lys Ser Ile Lys Trp Arg Glu Ser His
            420                 425                 430

```
Asp Cys Lys Tyr Ala Ile Gln Gly Gln Lys Ala Met Gly Thr Gly Ile
            435                 440                 445

His Arg Ser Gly His Leu Ile Gly Gly Asn Ala Thr Thr Tyr Ala Asp
        450                 455                 460

Pro Leu Asn Tyr Tyr His Tyr His Asn Thr Ile Asn Lys Arg Asp Glu
465                 470                 475                 480

Val Cys Glu Asp Phe Ile Asp Lys Ser Val Val Tyr Val Asn Pro Arg
                485                 490                 495

Asn Arg Thr Asp Ile Tyr Thr His Asp Asp Gly Leu Ala Val Leu Ala
            500                 505                 510

Asp His Ile Lys Glu Phe Glu Arg Asp Val Ile Gly Pro Gln Ser Phe
        515                 520                 525

Ile Leu
    530

<210> SEQ ID NO 29
<211> LENGTH: 526
<212> TYPE: PRT
<213> ORGANISM: Unknown
<220> FEATURE:
<223> OTHER INFORMATION: synthetic GALS Ppa_Pp1s112_159V6.1,
      glycosyltransferase family 92 (GT92) member,
      galactan synthase, beta-1,4,galactan synthase,
      beta-1,4 galactosyltransferase (GALS)

<400> SEQUENCE: 29

Met Ala Arg Gln Trp Leu Arg Lys Ser Glu Leu Asn Asp Lys Leu Trp
1               5                   10                  15

Lys Gly Asp Lys Gly Asp Thr Val Leu Asp Thr Ser Met Ala Gly Val
            20                  25                  30

Arg Thr Ala Leu Ser Ala Glu Ser Leu Ala Lys Phe Ile Leu Leu Val
        35                  40                  45

Gly Ile Asn Ser Val Phe Leu Leu Ala Ala Leu His Val Leu His Ser
    50                  55                  60

Asn Arg Glu Phe Glu Asn Pro Gly Asp Arg Ser Asn Cys Ile Thr Ser
65                  70                  75                  80

Asp Arg Leu Asn Asn Val His Pro Ile Ser Leu Ser Gln Asp Gln Asn
                85                  90                  95

Arg Leu Ile Lys Thr Ser Glu Ser Thr Thr Asn Asn Glu Leu Gln Glu
            100                 105                 110

Asn Val Arg Gln Phe Asp Thr Phe Gly Val Ala Val Tyr Leu Phe Ile
        115                 120                 125

Lys Met Ser Ala Tyr Arg Asp Gly Pro Arg Ser Phe Thr Ile Val Gly
    130                 135                 140

Leu Glu Ala Lys Asn Pro Ala Glu Leu Tyr Asn Asp Pro Pro Tyr Glu
145                 150                 155                 160

Cys Val Trp Ile Pro Gly Pro Asp Ser Val Trp Ala Pro Ser Lys
                165                 170                 175

Gly Ser Thr Phe Lys Met Leu Pro Asp Thr Gly Asn Val Tyr Ser Arg
            180                 185                 190

Leu Tyr Ser Ala Val Ile Ile Asn Cys Thr Phe Ser Gln Asp Val Gly
        195                 200                 205

Val Asp Arg Lys Gly Gly Gln Leu Val Leu Tyr Ala Ser Tyr Gly Asp
    210                 215                 220

Gln Phe Pro Arg Asn Pro Glu Arg Ile Val Ala Leu Thr Glu Ala Pro
225                 230                 235                 240
```

-continued

```
Asp Glu Phe Leu Gly Met Glu Tyr Tyr Glu Ser Pro Glu Met Lys Tyr
                245                 250                 255

Asp Tyr Val Tyr Cys Gly Ser Pro Leu Phe Gly Asn Leu Ser Pro Gln
            260                 265                 270

Lys Ile Arg Glu Trp Ile Ala Tyr His Ala His Phe Phe Gly Pro Arg
        275                 280                 285

Ser His Phe Phe Leu Tyr Asp Ala Gly Gly Ile His Glu Glu Val Arg
    290                 295                 300

Arg Val Ile Glu Pro Trp Ile Lys Ala Gly Arg Val Thr Leu Asp Asn
305                 310                 315                 320

Ile Arg Glu Gln Glu Lys Phe Asp Gly Tyr Tyr His Asn Gln Phe Leu
                325                 330                 335

Val Val Asn Asp Cys Phe His Arg Ala Arg Arg Leu Ala His Trp Leu
            340                 345                 350

Phe Phe Phe Asp Val Asp Glu Tyr Ile Trp Ala Pro Pro Asn Asp Asn
        355                 360                 365

Ser Leu Ala Ser Ile Leu Ala Arg Phe Glu Asp Gln Ser Gln Ile Ile
    370                 375                 380

Ile Trp Gln Lys Pro Met Ser Lys Ser Leu Cys Ala Gln Asp Gln Gly
385                 390                 395                 400

Ala Ala Ser Asn Asp Ser Ser Phe Ala Ser Lys Trp Thr Phe Glu Lys
                405                 410                 415

Leu Val Phe Lys Ser Ile Lys Trp Arg Glu Ser His Asp Cys Lys Tyr
            420                 425                 430

Ala Ile Arg Gly Leu Lys Ala Met Ala Thr Gly Ile His Arg Ser Gly
        435                 440                 445

Tyr Leu Ile Gly Ser Asn Ala Thr Thr Tyr Ala Asp Pro Leu Asn Tyr
    450                 455                 460

Tyr His Tyr His Asn Thr Ile Asn Lys Arg Glu Glu Val Cys Glu Gln
465                 470                 475                 480

Phe Ile Asp Ser Asn Ser Val Tyr Val Asn Pro Arg Asn Arg Thr Asp
                485                 490                 495

Lys Phe Ala Tyr Asp Asp Gly Leu Ala Val Leu Ala Asp His Ile Lys
            500                 505                 510

Glu Phe Glu Leu Asp Val Ile Gly Pro Gln Pro Phe Ile Leu
        515                 520                 525
```

<210> SEQ ID NO 30
<211> LENGTH: 523
<212> TYPE: PRT
<213> ORGANISM: Unknown
<220> FEATURE:
<223> OTHER INFORMATION: synthetic GALS Ppa_Pp1s32_144V6.1,
      glycosyltransferase family 92 (GT92) member,
      galactan synthase, beta-1,4,galactan synthase,
      beta-1,4 galactosyltransferase (GALS)

<400> SEQUENCE: 30

```
Met Lys Met Asp Lys Asn His Thr Val Val Lys Val Glu Lys Glu Thr
1               5                   10                  15

Glu Lys Val Asn Ala Lys Val Trp Ser Arg Glu Leu Gly Cys His Thr
            20                  25                  30

Ala Ile Lys Phe Gln Met Arg Thr Phe Pro Asp Val Arg Val Asn Val
        35                  40                  45

Val Tyr Thr Met Ile Phe Leu Ile Gly Leu Ile Leu Thr Ala Ala Gln
    50                  55                  60
```

```
Leu Trp Pro Leu Thr Asp Phe Asp Pro Lys His Ser Cys Thr Gln Pro
 65                  70                  75                  80

Ala Asn Gln Glu Asn Trp Glu Arg Leu Asp Lys Ser Glu Pro Gln Gln
                 85                  90                  95

Pro Gln Ile Phe Ser Glu Ser Phe Leu His Glu Lys Val Asp Ala Ser
            100                 105                 110

Ser Ile Asp Thr Ser His Gly Glu Leu Arg Val Phe Lys Pro His Gly
        115                 120                 125

Leu Ala Thr His Leu Tyr Ile Glu Met Ser Ala Tyr Arg Gly Gly Pro
    130                 135                 140

Arg Gln Phe Ser Val Val Gly Leu Thr Ser Lys Pro Ile Glu Ser His
145                 150                 155                 160

His Gln Pro Pro Tyr Ala Cys Glu Trp Val Ser Asn Ala Thr Gly Glu
                165                 170                 175

Val Val Lys Gly Arg Pro His Lys Val Leu Pro Asp Trp Asp Tyr Gly
            180                 185                 190

Lys Leu Tyr Thr Val Val Ile Thr Cys Asn Phe Ala Lys Asp Val
        195                 200                 205

Gly Val Asp Gly Glu Gly Gly Glu Leu Ile Leu Tyr Ala Ser Tyr Gly
210                 215                 220

Asp Gln Tyr Arg Gln Pro Glu Arg Ile Val Val Leu Thr Glu Ser Lys
225                 230                 235                 240

Gly Thr Tyr Asn Ser Ser Ile Phe Asp Pro Lys Asn Phe Pro Tyr Asp
                245                 250                 255

Tyr Val Tyr Cys Gly Ser Ser Val Tyr Gly Asp Ile Ser Pro Gln Arg
            260                 265                 270

Met Arg Glu Trp Met Ala Tyr His Ala Lys Leu Phe Gly Asp Gly Ser
            275                 280                 285

His Phe Ile Leu His Asp Ser Gly Phe His Asp Asp Val Arg Lys
    290                 295                 300

Val Ile Glu Pro Trp Ile Lys Gln Gly Arg Val Thr Leu Gln Asn Ile
305                 310                 315                 320

Arg Gln Gln Glu Ile Phe Asp Gly Tyr Tyr His Asn Gln Phe Leu Ile
                325                 330                 335

Val Asn Asp Cys Leu Phe Arg Ser Arg Phe Leu Ala Asn Trp Thr Phe
            340                 345                 350

Phe Phe Asp Ile Asp Glu Phe Ile Phe Val Glu Pro Thr Thr Thr Leu
        355                 360                 365

Ser Ala Val Leu Asn Glu Asn Pro Asn Ile Thr Gln Ile Thr Ile Glu
    370                 375                 380

Gln Thr Pro Met Ala Lys Asp Leu Cys Val Ala Asp Asn Thr Thr Ser
385                 390                 395                 400

Gly Glu His Glu Ser Arg Trp Gly Phe Glu Lys Leu Ile Tyr Arg Lys
                405                 410                 415

Val Leu Lys Arg Gly Ile Arg Tyr Asp Arg Lys Phe Val Gln Ala
            420                 425                 430

Arg His Ala Glu Ala Thr Gly Ile His Met Ser Met Asp Thr Arg His
    435                 440                 445

Gly Gln Asn Leu Tyr Pro Lys Gly Asp Lys Ile Arg Tyr Tyr His Tyr
    450                 455                 460

His Gly Thr Ile Asn Lys Arg Gln Glu Val Cys Thr Arg Phe Val Asp
465                 470                 475                 480

Ala Gly Asn Lys Thr Ala Val Gln Arg His Glu Lys His Tyr His Arg
```

```
                485                 490                 495
Leu Asp Glu Ser Met Ala Lys Leu Ala Lys Asp Val Lys Leu Phe Glu
            500                 505                 510

Leu Asn Thr Val Gly Ala Gln Pro Phe Ile Val
            515                 520

<210> SEQ ID NO 31
<211> LENGTH: 521
<212> TYPE: PRT
<213> ORGANISM: Unknown
<220> FEATURE:
<223> OTHER INFORMATION: synthetic GALS Ppa_Pp1s198_141V6.1,
      glycosyltransferase family 92 (GT92) member,
      galactan synthase, beta-1,4,galactan synthase,
      beta-1,4 galactosyltransferase (GALS)

<400> SEQUENCE: 31

Met Lys Met Glu Lys His Gln Thr Val Ile Lys Val Glu Asn Glu Thr
1               5                   10                  15

Gly Arg Val Lys Asp Lys Val Arg Ser Lys Glu Leu Arg Cys His Thr
            20                  25                  30

Ala Ile Lys Phe His Met Arg Ala Phe Pro Asp Ile Arg Val Asn Val
        35                  40                  45

Ile Tyr Thr Met Val Leu Ala Ile Gly Leu Cys Leu Val Ala Gln
    50                  55                  60

Phe Ser Pro Leu Leu Gly Phe Asp Pro Lys Val Trp Cys Ala Val Met
65                  70                  75                  80

Ala Lys Leu Glu Lys Leu Gly Lys Pro Glu Val Ser His Pro Pro Gln
                85                  90                  95

Leu Ile Ser Glu Ala Leu Phe His Glu Lys Ile Asn Thr Ser Ser Ile
            100                 105                 110

Asp Leu Thr His Gly Glu Leu Arg Leu Phe Lys Pro His Gly Leu Ala
        115                 120                 125

Thr His Leu Tyr Ile Glu Met Ser Ala Tyr Arg Gly Gly Pro Arg Val
    130                 135                 140

Phe Ser Ile Val Gly Leu Ala Ser Lys Ser Leu Glu Thr His His Asn
145                 150                 155                 160

Pro Pro Tyr Ala Cys Glu Trp Val Ser Asn Ser Thr Gly Glu Val Val
                165                 170                 175

Gln Gly Arg Ser His Lys Val Leu Pro Asp Trp Gly Tyr Gly Lys Leu
            180                 185                 190

Tyr Thr Val Val Ile Thr Cys Asn Phe Ala Lys Asp Val Gly Val
        195                 200                 205

Asp Gly Glu Asp Gly Glu Leu Ile Leu Leu Ala Ser Tyr Gly Asp Gln
    210                 215                 220

Tyr Arg Gln Pro Glu Arg Ile Lys Val Leu Ser Glu Ser Lys Gly Glu
225                 230                 235                 240

Tyr Asn Gly Ser Ile Phe Asn Pro Gln Asn Phe Pro Tyr Asp Tyr Val
                245                 250                 255

Tyr Cys Gly Ser Ser Val Tyr Gly Asn Ile Ser Pro Gln Arg Met Arg
            260                 265                 270

Glu Trp Met Ala Tyr His Ala Arg Phe Gly Asp Lys Ala His Phe
        275                 280                 285

Ile Leu His Asp Ser Gly Gly Phe His Glu Asp Val Arg Lys Val Leu
    290                 295                 300

Glu Pro Trp Ile Lys Gln Gly Lys Val Thr Leu Gln Asn Ile Arg Gln
```

```
                305                 310                 315                 320
Gln Glu Ile Tyr Asp Gly Tyr Tyr His Asn Gln Phe Leu Ile Val Asn
                325                 330                 335

Asp Cys Leu Phe Arg Ser Arg Phe Met Ala Asn Trp Thr Phe Phe Phe
                340                 345                 350

Asp Val Asp Glu Tyr Met Tyr Val Glu Pro Thr Thr Thr Leu Ser Gln
                355                 360                 365

Val Leu Asn Glu Asn Pro Asn Ile Thr Gln Ile Thr Ile Glu Gln Val
                370                 375                 380

Pro Met Ala Lys Asp Ile Cys Val Ala Asp Asn Ala Thr Arg Gly Asp
385                 390                 395                 400

Leu Lys Ser Ser Trp Gly Phe Glu Lys Leu Val Tyr Arg Lys Val Leu
                405                 410                 415

Lys Pro Gly Leu Arg Tyr Asp Arg Lys Tyr Ala Val Gln Ala Arg His
                420                 425                 430

Ala Glu Ala Ala Gly Ile His Met Ser Met Asn Met Leu Lys Gly Gln
                435                 440                 445

Asn Leu Tyr Pro Lys Gly Asp Lys Ile Arg Tyr Tyr His Tyr His Gly
                450                 455                 460

Thr Ile Asn Lys Arg Gly Glu Val Cys Lys Lys Phe Val Asp Ala Gly
465                 470                 475                 480

Asn Lys Thr Ala Leu Gln Thr His Asp Asn His Tyr His Arg Leu Glu
                485                 490                 495

Glu Thr Ile Ala Lys Met Ala Lys Asp Val Lys Leu Tyr Glu Leu Asn
                500                 505                 510

Thr Val Gly Thr Gln Pro Phe Ile Val
                515                 520

<210> SEQ ID NO 32
<211> LENGTH: 503
<212> TYPE: PRT
<213> ORGANISM: Unknown
<220> FEATURE:
<223> OTHER INFORMATION: synthetic GALS Ppa_Pp1s227_17V6.1,
      glycosyltransferase family 92 (GT92) member,
      galactan synthase, beta-1,4,galactan synthase,
      beta-1,4 galactosyltransferase (GALS)

<400> SEQUENCE: 32

Met Glu Arg Glu His Ser Val Leu Lys Val Glu Ala Gly Arg Glu Lys
1               5                   10                  15

Ala Cys Ser Arg Pro Gln Leu Gly Cys Ser Thr Pro Ile Lys Phe Ser
                20                  25                  30

Thr Ile Arg Leu Asn Ile Ile Tyr Pro Met Val Met Ala Ile Val Leu
                35                  40                  45

Phe Leu Val Val Thr Gln Leu Leu Ser Leu Ser Gly Phe Gly Ile Lys
                50                  55                  60

Phe Trp Cys Thr Glu Thr Thr Lys Val Val Gly Leu Glu Thr Gln Leu
65              70                  75                  80

Ser Pro Ser Leu Pro Gln Gly Ser Phe Leu Asp Glu Asn Ile Asp Thr
                85                  90                  95

Ser Ser Ile Asp Leu Arg His Gly Asp Val Arg Leu Phe Lys Pro His
                100                 105                 110

Gly Leu Ala Thr Tyr Leu Tyr Ile Asp Met Ser Ala Tyr Arg Gly Ser
                115                 120                 125

Pro Arg His Phe Ser Ile Val Gly Leu Thr Ala Lys Ser Ile Glu Lys
```

```
                130             135             140
His His Lys Pro Pro Tyr Ala Cys Glu Trp Val Ser Ser Asn Asp
145                 150                 155                 160

Lys Val Val Lys Gly His Ala Tyr Lys Ile Leu Pro Asp Trp Asp Tyr
                165                 170                 175

Gly Lys Leu Tyr Thr Val Val Ile Thr Cys Val Phe Ala Glu Asp
            180                 185                 190

Val Gly Thr Asp Gly Glu Gly Gly Leu Val Leu Tyr Ala Ser Tyr
            195                 200                 205

Gly Asp Arg Tyr Arg Gln Pro Glu Arg Val Val Leu Thr Glu Val
    210                 215                 220

Lys Gly Glu Tyr Asn Ser Ser Val Phe Asp Thr Lys Ser Phe Pro Tyr
225                 230                 235                 240

Asp Tyr Val Tyr Cys Gly Ser Ser Val Tyr Gly Asn Ile Ser Pro Gln
                245                 250                 255

Arg Met Arg Glu Trp Met Ala Tyr His Ala Lys Phe Phe Gly Glu Lys
                260                 265                 270

Ser His Phe Ile Leu His Asp Ala Gly Gly Phe His Glu Asp Val Arg
            275                 280                 285

Lys Val Leu Glu Pro Trp Ile Arg Gln Gly Arg Val Thr Leu Gln Asn
                290                 295                 300

Ile Arg Gln Gln Glu Ile Tyr Asp Gly Tyr Tyr His Asn Gln Phe Met
305                 310                 315                 320

Val Val Asn Asp Cys Leu Phe Arg Ser Arg Phe Leu Ala Asn Trp Thr
                325                 330                 335

Phe Phe Phe Asp Ile Asp Glu Tyr Met Tyr Val Asp Pro Ser Thr Thr
                340                 345                 350

Leu Ser Asp Val Leu Asn Glu Lys Pro Asp Val Ser Gln Ile Val Ile
            355                 360                 365

Lys Gln Val Pro Ile Glu Ser Gly Leu Cys Val Ala Asp Asn Thr Arg
    370                 375                 380

Asp Gln His Glu Arg Trp Leu Thr Glu Arg Leu Ile Tyr Arg Arg Val
385                 390                 395                 400

Leu Lys His Gly Ile His Tyr Asp Arg Lys Tyr Ala Val Gln Ala Arg
                405                 410                 415

His Ala Glu Ala Thr Gly Ile His Met Ser Met Asn Leu Arg Arg Gly
            420                 425                 430

Lys Thr Arg Val Leu Gln Asp Glu Arg Leu Arg Tyr Tyr His Tyr His
            435                 440                 445

Gly Thr Ile Thr Asn Arg Gly Asn Leu Cys Asn Lys Phe Val Asp Ser
    450                 455                 460

Lys Asn Lys Thr Ala Val Lys Ser Val Gln Leu Arg Leu Asp Glu Thr
465                 470                 475                 480

Met Met Lys Met Ala Lys Asp Val Lys Ser Tyr Glu Leu Lys Met Ile
                485                 490                 495

Gly Lys Gln Pro Phe Val Leu
            500
```

<210> SEQ ID NO 33
<211> LENGTH: 515
<212> TYPE: PRT
<213> ORGANISM: Unknown
<220> FEATURE:
<223> OTHER INFORMATION: synthetic GALS Ppa_Pp1s35_63V6.1,
      glycosyltransferase family 92 (GT92) member, galactan synthase, beta-1,4,galactan synthase,
beta-1,4 galactosyltransferase (GALS)

<400> SEQUENCE: 33

```
Met Asp Phe Lys Asp Thr Ala Ala Arg Glu Ser Gly Lys Val Lys Glu
1               5                   10                  15

Lys Val Gly Ser Lys Glu Val Asp Cys Gln Ala Ala Val Lys Phe His
            20                  25                  30

Met Ser Ala Phe Ser Asp Leu Arg Ile Tyr Leu Val Tyr Val Leu Ile
        35                  40                  45

Ala Ala Cys Cys Phe Leu Ile Leu Leu Ala Gln Leu Leu Pro Leu Arg
    50                  55                  60

Ser Leu Asp Lys Ser Gln Leu Pro Cys Asn Asp Ser Val Ser Ile Val
65                  70                  75                  80

Ser Pro Glu Thr Asn Leu Glu Phe Pro Ile Asp Pro Leu Ser Lys Ser
                85                  90                  95

Phe Leu His Glu Asn Ile Ile Asn Lys Ser Ser Leu Asp Ile Ser Lys
            100                 105                 110

Gly Glu Leu Arg Val Phe Lys Pro His Gly Leu Ala Met His Leu Phe
        115                 120                 125

Ile Glu Met Gly Ala Tyr Arg Gly Gly Pro Arg Val Phe Ser Val Val
    130                 135                 140

Gly Leu Ile Ala Lys Pro Ile Gln Thr Phe His Lys Pro Pro Tyr Val
145                 150                 155                 160

Cys Glu Trp Val Thr Asn Val Gly Arg Thr Ile Lys Gly Arg Ala Ser
                165                 170                 175

Lys Ile Leu Pro Asp Trp Asn Tyr Gly Arg Leu Tyr Thr Val Val Val
            180                 185                 190

Ile Thr Cys Thr Phe Arg Val Asp Val Gly Val Gln Lys Glu Gly Gly
        195                 200                 205

Glu Leu Val Leu Gln Val Ser Tyr Gly Asp Gln Phe Arg Gln Pro Glu
    210                 215                 220

Lys Ile Val Val Leu Thr Glu Arg Arg Gly Tyr Asn Ala Thr Met
225                 230                 235                 240

Phe Asp Pro Pro Tyr Pro Tyr Asp Tyr Val Tyr Cys Gly Ser Ser Leu
                245                 250                 255

Tyr Gly Asp Val Ser Pro Gln Arg Met Arg Glu Trp Leu Ala Tyr His
            260                 265                 270

Ala His Phe Phe Gly Glu Arg Ser His Phe Met Phe His Asp Ala Gly
        275                 280                 285

Gly Phe His Pro Gln Val Trp Lys Val Leu Asp Pro Trp Ile Lys Lys
    290                 295                 300

Gly Arg Val Ser Val Gln Asn Ile Gln Gln Glu Ile Tyr Asp Gly
305                 310                 315                 320

Tyr Tyr His Asn Gln Phe Leu Val Val Asn Asp Cys Leu Phe Arg Ser
                325                 330                 335

Arg Phe Met Ala Asn Trp Thr Phe Phe Asp Val Asp Glu Tyr Leu
            340                 345                 350

His Val Pro Pro Thr Thr Thr Leu Asp Lys Val Leu Asn Asp Pro
        355                 360                 365

Asn Val Thr Gln Ile Thr Phe Glu Gln Val Pro Ile Ser Asn Asn Leu
    370                 375                 380

Cys Val Ala Asp Asn Ile Thr Thr Asp Gly His Ala Arg Lys Trp Ala
385                 390                 395                 400
```

```
Ile Glu Lys Leu Met Tyr Arg Lys Val Leu Arg Ser Gly Val Arg Tyr
            405                 410                 415

Asp Arg Lys Tyr Ala Val Gln Ala Arg Tyr Ala Ala Ala Thr Gly Val
        420                 425                 430

His Met Ser Met Asn Met Arg Lys Gly Lys Asn Met Tyr Pro Lys Gly
    435                 440                 445

Tyr Lys Ile Arg Tyr Tyr His Tyr His Asp Thr Ile Asn Lys Arg Glu
    450                 455                 460

Glu Leu Cys Gln Ala Phe Val Ser Pro Gln Asn Lys Thr Ser Leu Gln
465                 470                 475                 480

Arg His Gln Arg Gln Asn Tyr Arg Leu Asp Glu Thr Leu Ala Met Thr
                485                 490                 495

Thr Gln Leu Ile Lys Asp Tyr Glu Arg Arg Thr Ile Gly Ser Leu Pro
            500                 505                 510

Phe Ile Val
        515

<210> SEQ ID NO 34
<211> LENGTH: 488
<212> TYPE: PRT
<213> ORGANISM: Unknown
<220> FEATURE:
<223> OTHER INFORMATION: synthetic GALS Ppa_Pp1s237_6V6.1,
      glycosyltransferase family 92 (GT92) member,
      galactan synthase, beta-1,4,galactan synthase,
      beta-1,4 galactosyltransferase (GALS)

<400> SEQUENCE: 34

Met Lys Ser Gln Lys Ser Leu Val Glu Asn Ile Pro Thr Ser Gly Leu
1               5                   10                  15

Gly Phe Asn Ala Val Val Val Leu Val Val Ile Asn Cys Leu Leu Leu
            20                  25                  30

Val Phe Gln Ile Ser Ser Ser Gly Ser Leu Tyr Glu Arg Ala Trp Trp
        35                  40                  45

Pro Thr Glu Ala Gln Pro Met Pro Cys Ala Asn Ile Thr Ile Ala Met
    50                  55                  60

Asp Glu Asn Leu Asp Met Ser Ser Ile Asp Leu Ser Arg Gly Glu Val
65                  70                  75                  80

Arg Ser Phe Arg Ala His Gly Ile Ala Thr Arg Leu Ile Val Glu Val
                85                  90                  95

Gly Ser Tyr Arg Asn Gly Pro Arg Thr Phe Ser Ser Val Val Leu Thr
            100                 105                 110

Ser Lys Arg Leu Asn Asn Leu His Asp Ile Leu Tyr Glu Cys Glu Trp
        115                 120                 125

Ala Thr Ala Asp Ser Pro Thr Leu Lys Val Lys Arg Ala Ile Lys
    130                 135                 140

Pro Asp Trp Asn Met Gly Glu Leu Tyr Gly Thr Met Val Ile Val Cys
145                 150                 155                 160

Thr Phe Pro Lys Asp Val Gly Thr Lys Ser Glu Gly Gly Arg Leu Ile
                165                 170                 175

Leu Thr Ala His Tyr Pro Gly Ala Phe Arg Thr Pro Gly Arg Phe Ile
            180                 185                 190

Ala Leu Thr Glu Met Gln Gly Glu Tyr Asn Ala Ser Arg Phe Gln Pro
        195                 200                 205

Pro Tyr Pro Tyr Asp Met Thr Phe Cys Gly Ser Pro Leu Tyr Gly Asn
    210                 215                 220
```

```
Ile Ser Pro Gln Arg Ile Arg Glu Trp Ile Ala Tyr His Ala Tyr Phe
225                 230                 235                 240

Leu Gly Asn Arg Thr Leu Phe Ile Phe Gln Asp Ala Gly Gly Ile His
            245                 250                 255

Asp Asp Val Tyr Arg Val Leu Lys Pro Trp Ile Asp Leu Gly Gln Val
        260                 265                 270

Leu Val Glu Asn Leu Arg Gln Ala Glu Val Tyr Glu Gly Tyr Tyr His
    275                 280                 285

His Gln Phe Thr Met Leu Asn Asp Cys Leu Leu Arg Ser Gln Thr Leu
290                 295                 300

Ser Asn Trp Thr Phe Phe Asp Val Asp Glu Phe Leu Phe Ser Ser
305                 310                 315                 320

Gly Asp Lys Lys Pro Val Asp Leu Leu Ala Glu Asn Ala Arg Asn Asn
                325                 330                 335

Val Thr Gln Phe Leu Phe Lys Thr Val Lys Met Ser Asp Gly Leu Cys
            340                 345                 350

Leu Lys Glu Asn Lys Arg Glu Ser Asp Ser His Phe Met Ala Lys Ile
        355                 360                 365

Ser Arg Lys Trp Ala Phe Glu Lys Leu Val Tyr Ala Lys Cys Asp Tyr
    370                 375                 380

Gly Trp Thr Thr Val Glu Ser Arg Lys Tyr Ala Val Gln Pro Gln Met
385                 390                 395                 400

Val Trp Ala Thr Gly Val His Tyr Ser Glu His Met Lys Gln Gly Lys
                405                 410                 415

Arg Ile Asp Met Asp Pro Asp Val Leu Arg Ser Tyr His Tyr His Asn
            420                 425                 430

Thr Val Asn Gly Arg Thr Glu Leu Cys Lys Glu Phe Pro Lys Asn Pro
        435                 440                 445

Asn Gly Glu Pro Asn Ser Leu Lys Val Lys Asn Cys Thr Ile Asp Lys
    450                 455                 460

Ser Met Ala Asp Leu Gly Pro Ala Val Arg Ser Tyr Glu Phe Ala Met
465                 470                 475                 480

Val Gly Glu Gln Pro Phe Ile Leu
                485
```

<210> SEQ ID NO 35
<211> LENGTH: 492
<212> TYPE: PRT
<213> ORGANISM: Unknown
<220> FEATURE:
<223> OTHER INFORMATION: synthetic GALS Ppa_Pp1s98_254V6.1,
      glycosyltransferase family 92 (GT92) member,
      galactan synthase, beta-1,4,galactan synthase,
      beta-1,4 galactosyltransferase (GALS)

<400> SEQUENCE: 35

```
Met Lys Ser Ser Thr Gly Lys Ile Leu Glu Arg Ile Pro Ala Ser Gly
1               5                   10                  15

Thr Cys Phe Ser Val Val Ala Val Leu Val Ile Leu Asn Cys Leu Leu
            20                  25                  30

Leu Gly Phe Gln Ile Ser Ser Asn Ala Gly Arg Tyr Glu Ser Thr Trp
        35                  40                  45

Trp Leu Ala Ser Ala Pro Pro Met Ala Cys Thr Asn Ala Ser Phe Ala
    50                  55                  60

Leu Asp Glu Lys Leu Asn Met Ser Ser Ile Asp Leu Ser Lys Gly Glu
65                  70                  75                  80
```

```
Val Arg Ser Phe Arg Ala His Gly Val Ala Ser Arg Leu Ile Ile Glu
                85                  90                  95

Val Gly Ser Tyr Arg Asn Gly Pro Arg Thr Phe Ser Ser Val Val Met
            100                 105                 110

Thr Ser Lys Leu Leu Asn Glu Leu His Asp Ile Thr His Glu Cys Glu
            115                 120                 125

Trp Val Thr Ser Asp Ser Lys Ala Leu Arg Val Lys Ala Met Ala Ile
        130                 135                 140

Lys Pro Asp Trp Asn Met Gly Arg Leu Tyr Gly Thr Met Val Leu Val
145                 150                 155                 160

Cys Asn Phe Pro Arg Asp Val Gly Thr Asp Ala Glu Gly Gly Gln Met
                165                 170                 175

Ile Leu Thr Ala Gly Tyr Ser Asp Ser Tyr Arg Ile Pro Glu Arg Phe
            180                 185                 190

Val Ala Leu Thr Glu Met Arg Gly Glu Tyr Ser Ala Ser His Phe Gln
            195                 200                 205

Gln Pro Tyr Ser Tyr Asp Leu Ala Phe Cys Gly Ser Pro Leu Tyr Gly
    210                 215                 220

Asn Ile Ser Pro Gln Arg Val Arg Glu Trp Ile Ala Tyr His Ala Trp
225                 230                 235                 240

Phe Phe Gly Asn Arg Thr Leu Phe Met Phe His Asp Ala Gly Gly Ile
                245                 250                 255

His Asp Asp Val Tyr Arg Val Leu Lys Pro Trp Ile Asp Leu Gly Arg
            260                 265                 270

Val Gln Val Gln Asn Leu Arg Gln Ala Glu Val Tyr Glu Gly Tyr Tyr
            275                 280                 285

His His Gln Phe Thr Ile Leu Asn Asp Cys Leu Met Arg Ser Gln Thr
        290                 295                 300

Leu Ala Ser Trp Thr Phe Phe Asp Ile Asp Glu Tyr Leu Tyr Ile
305                 310                 315                 320

Pro Glu Ala His Ser Pro Arg Ala Ile Leu Asn Leu Ala Glu Gln
                325                 330                 335

Ala Arg Asn Asn Val Thr Gln Ile Leu Phe Lys Asn Ile Lys Ile Ser
            340                 345                 350

Asp Ala Leu Cys Glu Lys Ser Asn Lys Thr Thr Glu Ala Gln Ser
    355                 360                 365

Met Ala Lys Gln Ser Arg Lys Trp Ala Phe Glu Lys Leu Val Tyr Ala
370                 375                 380

Asp Cys Asn Tyr Gly Trp Glu Pro Val Glu Ser Arg Lys Tyr Ala Leu
385                 390                 395                 400

Gln Pro Gln Leu Val Trp Ala Thr Gly Val His Tyr Ser Glu His Leu
                405                 410                 415

Lys Gln Gly His Tyr Ile Thr Met Asp Pro Thr Val Leu Arg Ser Tyr
            420                 425                 430

His Tyr His Asn Thr Leu Asn Gly Arg Trp Glu Thr Cys Lys Asp Phe
            435                 440                 445

Pro Gln His Pro Asn Gly Gly Pro Asn Ser Val Asn Val Thr Asn Cys
450                 455                 460

Thr Thr Asp His Ala Met Leu Ser Phe Ala Pro Ala Val Lys Ser Tyr
465                 470                 475                 480

Glu Leu Ala Thr Ile Gly Glu Gln Pro Phe Leu Leu
                485                 490
```

-continued

<210> SEQ ID NO 36
<211> LENGTH: 505
<212> TYPE: PRT
<213> ORGANISM: Unknown
<220> FEATURE:
<223> OTHER INFORMATION: synthetic GALS Ppa_Pp1s25_268V6.1,
      glycosyltransferase family 92 (GT92) member,
      galactan synthase, beta-1,4,galactan synthase,
      beta-1,4 galactosyltransferase (GALS)

<400> SEQUENCE: 36

```
Met Lys Ser Lys Thr Asp Trp Pro Gln Gly Arg Val Gly Leu Leu Asn
1               5                   10                  15

Val Val Val Ile Leu Leu Leu Thr Asn Val Leu Leu Leu Ala Leu
            20                  25                  30

Leu Thr Thr Asp Ile Arg Ile Ser Gln Asp Leu Trp Trp Pro Lys Pro
            35                  40                  45

Gly Ser Thr Gly Pro Thr Leu Arg Leu Ser Asp Asp Ile Thr Phe Ser
    50                  55                  60

Pro Ser Glu Leu Ile Ser Glu Ser Thr Gln Asn Gln His Arg Ala Leu
65                  70                  75                  80

Tyr Pro Val Thr Leu Asn Thr Thr Leu Asp Thr Ser Arg Gly Glu
                85                  90                  95

Leu Arg Thr Phe Lys Pro His Gly Ile Ala Ser His Leu Phe Ile Glu
            100                 105                 110

Phe Gly Ala Tyr Arg Ile Ser Pro Ser Gln Phe Ser Ile Val Gly Leu
        115                 120                 125

Ile Ser Lys Arg Leu His Asp Leu His Asp Pro Tyr Asn Cys Thr
130                 135                 140

Trp Arg Ser Gly Glu Val Thr Val Ser Ala Leu Thr Thr Trp Pro Ile
145                 150                 155                 160

Lys Pro Asp Trp Glu Leu Gly Leu Met Tyr Gly Thr Met Val Val Val
                165                 170                 175

Cys Ile Phe Pro Glu Asp Val Gly Thr Ala Gly Glu Gly Gly Ser Leu
            180                 185                 190

Gln Leu Ser Ile Gly Tyr Ala Asp Glu Phe Arg Gln Pro Glu Asn Phe
        195                 200                 205

Val Val Leu Thr Glu Glu Ala Gly Lys Tyr Asn Ala Ser Leu Trp Met
    210                 215                 220

Pro Pro Phe Pro Tyr Asp Ile Thr Phe Cys Val Ser Arg Leu Tyr Asn
225                 230                 235                 240

Thr Val Asp Ala His Arg Ile Arg Glu Trp Leu Ala Tyr His Ala His
                245                 250                 255

Leu Phe Gly Asn Arg Thr His Phe Leu Phe His Asn Ala Gly Gly Leu
            260                 265                 270

Asn Ser Asp Val Tyr Lys Val Leu Lys Pro Trp Ile Asp Leu Gly Arg
        275                 280                 285

Val Ser Val Gln Asn Leu Val Met Leu Glu Val Tyr Gln Gly Arg Ser
    290                 295                 300

His His Gln Phe Thr Met Leu Asn Asp Cys Met Phe Arg Ala Gln Thr
305                 310                 315                 320

Leu Ser Asn Trp Thr Phe Phe Asp Val Asp Glu Tyr Leu Tyr Ile
                325                 330                 335

Pro Pro Asn Lys Ile Leu Gln Ile Leu Asp Glu Ser Glu Arg Met
            340                 345                 350
```

```
Asn Phe Thr Gln Ile Arg Met Lys Thr Ile Lys Met Asn Asp Ala Leu
            355                 360                 365

Cys Thr Lys Pro Asp Pro Pro Leu Asp Asp Ala Ala Arg Asp Ala Val
370                 375                 380

Asn Ala Arg Lys Trp Ala Ile Glu Lys Leu Val Tyr Ala Asn Cys Asp
385                 390                 395                 400

Tyr Gly Trp Glu Pro Val Glu Ser Arg Lys Tyr Ala Leu Lys Pro Arg
                405                 410                 415

Ala Ala Trp Ala Thr Gly Val His Tyr Cys Glu Tyr Leu Lys Glu Gly
            420                 425                 430

Gly Leu Met Asp Ala Asp Glu Asn Leu Leu Arg Leu Tyr His Tyr His
            435                 440                 445

Gly Thr Thr Pro Gly Pro Lys Glu Val Cys Arg Asp Phe Thr Asn Gly
        450                 455                 460

Thr Asn Gly Glu Pro Asn Tyr Leu Gly Val Lys Asn Cys Thr Val Asp
465                 470                 475                 480

Arg Thr Met Thr Thr Leu Ala Asn Pro Val Lys Gln Phe Glu Leu Gln
                485                 490                 495

Thr Ile Gly Lys Gln Ser Thr Leu Glu
            500                 505

<210> SEQ ID NO 37
<211> LENGTH: 542
<212> TYPE: PRT
<213> ORGANISM: Unknown
<220> FEATURE:
<223> OTHER INFORMATION: synthetic GALS Ppa_Pp1s225_53V6.1,
      glycosyltransferase family 92 (GT92) member,
      galactan synthase, beta-1,4,galactan synthase,
      beta-1,4 galactosyltransferase (GALS)

<400> SEQUENCE: 37

Met Val Lys Pro Asp Phe Thr Gln Cys Arg Leu Arg Lys Phe Leu Gly
1               5                   10                  15

Arg Phe Ser Leu Asn Ser Lys Thr Thr Gly Phe Ser Leu Lys Arg Ala
            20                  25                  30

Thr Ala Thr Leu Phe Leu Val Ile Leu Pro Leu Val Leu Leu Val Thr
        35                  40                  45

Leu Leu His Glu Leu Ser Gly Leu Arg Thr Gly Ile Trp Leu Ser Thr
50                  55                  60

Ser Arg Ser Gln Ala Gln Gly Pro Arg Glu Ser Ser Glu Thr Ala Arg
65                  70                  75                  80

Lys Phe Leu Ser Arg Ala His Gly Gln Asn Pro Lys Arg Leu Ser Asp
                85                  90                  95

Glu Thr Tyr Pro Leu Gln Arg Pro Leu Asn Pro Lys Thr Val Met Ser
            100                 105                 110

Thr Val Phe Leu Arg Glu Ser Asn Ile Asn Ala Ser Lys Phe Asp Leu
        115                 120                 125

Arg Arg Gly Glu Ile Arg Ala Tyr Arg Pro His Gly Val Ala Ala His
    130                 135                 140

Phe Phe Leu Gln Leu Gly Thr Tyr Arg Ser Ser Pro Arg Ala Phe Ser
145                 150                 155                 160

Thr Ala Gly Ser Ile Gln Arg Ser Phe Glu Asp Trp Phe Lys Pro Arg
                165                 170                 175

Phe Gln Cys Glu Trp Ile Gly Ser Asn Gly Thr Ala Val Arg Ala Lys
            180                 185                 190
```

Glu Ala Lys Lys Ile Arg Pro Ala Gln Ser Phe Lys Gly Phe Tyr Asp
            195                 200                 205

Ser Leu Ile Ile Ile Cys His Phe Asp Glu Asp Val Gly Thr Asp Gly
210                 215                 220

Leu Gly Gly Lys Leu Tyr Met Lys Tyr Trp His Gln Val Asp Lys Tyr
225                 230                 235                 240

Arg Thr Pro Glu Thr Phe Leu Ala Leu Val Glu Ala Pro Ser Glu Tyr
            245                 250                 255

Asn Ala Ser Met Phe Glu Pro Pro Ala Tyr Asp Ile Val Tyr Cys
            260                 265                 270

Gly Ser Pro Ile Tyr Gly Asp Ile Ser Pro Gln Arg Val Arg Glu Trp
            275                 280                 285

Val Ala Tyr His Thr Tyr Val Phe Gly Asn Arg Ser His Phe Ile Leu
290                 295                 300

Tyr Asp Ala Gly Gly Phe His Asp Asp Val Gln Lys Val Leu Glu Pro
305                 310                 315                 320

Trp Val Lys Leu Gly Arg Val Thr Val Gln Asn Ile Gln Gln Ile Glu
            325                 330                 335

Met Tyr Pro Ala Tyr Tyr His His Gln His Thr Val Val Asn Asp Cys
            340                 345                 350

Leu Met Lys Ser Gln Phe Leu Ala Asn Trp Thr Phe Phe Asp Met
355                 360                 365

Asp Glu Tyr Leu Phe Val Glu Pro Pro His Ser Ile Thr Lys Leu Leu
            370                 375                 380

Glu Glu Lys Thr Gln Gln Asp Val Ser Val Ile Arg Tyr Thr Gly Lys
385                 390                 395                 400

Arg Met Ser Thr Ser Met Cys Ser Leu Pro Lys Ala Asn Val Asp Asn
            405                 410                 415

Ala Thr Arg Asp Ala Ile Asn Ser Lys Leu Trp Gly Phe Glu Lys Phe
            420                 425                 430

Leu Leu His Trp His Trp Glu His Gly Pro Arg Asp Pro Lys Tyr Ala
            435                 440                 445

Val Gln Ala Arg His Met Trp Ala Val Glu Ile His Asn Ala Val Leu
450                 455                 460

Ala Arg Arg Gly Gln Asn Arg Leu Leu Gln Tyr Arg Asp His Ile Trp
465                 470                 475                 480

Phe His His Phe His Gly Phe Ile Ile Asn Arg Ala Glu Gly Cys Arg
            485                 490                 495

Asp Phe Val Glu Ala Ser Glu Asn Lys Ala Ile Ala Val Gly Lys Ser
            500                 505                 510

Gln Tyr Ser Gly Asp Tyr Thr Ile Ala Arg Leu Ala Lys Asp Ile Lys
            515                 520                 525

Gln Phe Glu Gln Ala Met Val Gly Lys Leu Pro Phe Ile Leu
            530                 535                 540

<210> SEQ ID NO 38
<211> LENGTH: 525
<212> TYPE: PRT
<213> ORGANISM: Unknown
<220> FEATURE:
<223> OTHER INFORMATION: synthetic GALS Ppa_Pp1s556_1V6.1,
      glycosyltransferase family 92 (GT92) member,
      galactan synthase, beta-1,4,galactan synthase,
      beta-1,4 galactosyltransferase (GALS)

<400> SEQUENCE: 38

```
Met Ser Tyr Ser Val Ser Gln Gln Phe Ser Asn Ile Leu Ser Thr Arg
1               5                   10                  15

Cys Thr Ala Cys Leu Gly Gln Ala Leu Ile Phe Pro Cys Trp Phe Ala
                20                  25                  30

Arg Leu Thr Ile Ala Gly Phe Leu Glu Tyr Arg Ser Cys Lys Gly Phe
            35                  40                  45

Pro Ser Ile Ser Asp Lys Leu His Ala Ser Ala Lys Asp Asn Tyr
    50                  55                  60

Leu Gly Phe Gly Ser Ile Gln Gly Ser Gln Ala Lys Tyr Ser Glu Pro
65                  70                  75                  80

Lys Val Val Lys Glu Trp Gln Leu Pro Ser Ile Val Ala Asp Arg Ala
                85                  90                  95

Ala Glu Lys Leu Asn Asp Ser Ser Tyr Gly Leu Pro Arg Arg Phe Leu
                100                 105                 110

Pro Met Gly Thr Ala Thr Phe Leu Phe Val His Phe Ser Thr Tyr Arg
            115                 120                 125

Val Ala Pro Lys Ser Phe Ala Thr Ile Gly Leu Gly Pro Lys Ala Leu
    130                 135                 140

Phe Leu Tyr Ser Asn Pro Ala Phe Phe Cys Ser Trp His Pro Ala Lys
145                 150                 155                 160

Glu Ala Ala Pro Val Ile Lys Thr Asn Gly Thr Phe Leu Gln Pro Val
                165                 170                 175

Pro Thr His Val Ser Tyr Gly Lys Gln Tyr Thr Gly Thr Ala Val Tyr
            180                 185                 190

Cys Asn Phe Asp Thr Pro Ile Gly Asn Asp Gly Ser Gly Gly Arg Leu
    195                 200                 205

Glu Ile Gln Val Thr His Gly Thr Gln Asp Ala Ser Gly Leu Glu Asp
210                 215                 220

Val Asn Phe Val Ala Lys Glu Glu Gly Ala Gly Glu Phe Asn Ala Ser
225                 230                 235                 240

Leu Tyr Gln Glu Pro Tyr Gln Tyr Asp His Val Tyr Cys Gly Ala Pro
                245                 250                 255

Ile Tyr Gly Ser Ile Asn Ala Gln Arg Ile Arg Glu Trp Ile Ala Tyr
            260                 265                 270

His Val Trp Phe Phe Gly Glu Arg Thr His Phe Tyr Leu Tyr Asp Ala
        275                 280                 285

Gly Gly Phe Asp Glu Gln Val Arg Ala Val Leu Gln Pro Trp Val Lys
    290                 295                 300

Leu Gly Val Val Ile Ile Met Asn Ile Arg Gln Glu Ala Arg Phe Asn
305                 310                 315                 320

Ser His Tyr His Asn Gln Phe Val Ile Leu Asn Asp Cys Leu Phe Arg
            325                 330                 335

Ala Lys Ser Met Ala Lys Trp Thr Trp Phe Phe Asp Val Asp Glu Tyr
            340                 345                 350

Ile His Arg Pro Ala Gly Ser Asn Leu Asn Glu Val Ile Lys Arg Ile
            355                 360                 365

Glu Thr Glu Asn Phe Trp Gly Lys Arg Leu Gln Arg Val Ser Ile Lys
    370                 375                 380

Gln Met Ser Met Asp Tyr Ser His Cys Leu Arg Gly Ser Gln Pro Asn
385                 390                 395                 400

Ser Asn Glu Trp Gly Ile Ser Lys Met Val Tyr Arg Lys Thr Asp Val
                405                 410                 415

Gly Glu Tyr Pro Asp Arg Lys Asn Phe Val Leu Ser Asp Ser Cys Leu
```

```
            420             425             430
Ala Thr Gly Pro His Glu Pro Met Ala Met Ser Met Pro Pro Gly Ala
            435             440             445

Asn Gln Thr His His Val Thr Lys Trp Glu Gly Glu Leu Leu Gln Tyr
            450             455             460

Tyr His Phe His Gly Ala Ile Gly Lys Ala Glu Gly Glu Ile Cys Val
465             470             475             480

Asp Leu Leu Asp Pro Asp Val Asn Val Thr Ser Phe Asn Asn Val Thr
            485             490             495

His Gln Phe Asp Asp Ala Leu Lys Ser Leu Val Asp Asp Val Met Ala
            500             505             510

Phe Glu His Arg Met Ile Asn Gln Ala Thr His Thr Ser
            515             520             525

<210> SEQ ID NO 39
<211> LENGTH: 534
<212> TYPE: PRT
<213> ORGANISM: Unknown
<220> FEATURE:
<223> OTHER INFORMATION: synthetic GALS Smo_406883, glycosyltransferase
      family 92 (GT92) member, galactan synthase,
      beta-1,4,galactan synthase, beta-1,4
      galactosyltransferase (GALS)

<400> SEQUENCE: 39

Met Ala Ala Phe His Lys Ala Met Ile Cys Arg Ile Trp Ile Val Leu
1               5                   10                  15

Leu Val Thr Leu Leu Trp Ile Gly Leu Trp Tyr Ser Arg Ile Ser Pro
            20                  25                  30

Ala Thr Ser Asp Leu Ala Ala His Arg Lys Asp Leu His Arg Phe Gly
        35                  40                  45

Gly Asn Leu Ala Arg Asn Ser Ser Phe Ser Lys Phe Trp Glu Val Glu
    50                  55                  60

Asp Gly Gln Leu Thr Ala Asp Leu Ile His Glu Val Val Glu Glu Leu
65                  70                  75                  80

Glu Lys Ile Arg Asp Gly Thr Pro Gly Gly Val Val Ala Ala Asn Arg
                85                  90                  95

Lys Glu Pro Cys Asp Glu Arg Arg Asp Leu Ala Arg Glu Arg Gly Phe
            100                 105                 110

Arg Arg Ile Gly Glu Thr Leu His Ala Phe Val Leu Ser Ser Val Ala
        115                 120                 125

Arg Phe Ser Leu Glu Glu Phe Thr Ala Val Gly Leu Val Ser Ile Gln
    130                 135                 140

Leu Arg Gly Phe Ala Gly Asn Pro Leu Gln Ser Cys Ala Trp Val Pro
145                 150                 155                 160

Lys Ala Gly Ser Ser Ser Val Ala Ala Leu Ala Ala Ser Asn Asp
                165                 170                 175

Ser Ser Val Ile Trp Gly Asn Ser Trp Leu Gly Tyr Val Asn Glu Ser
            180                 185                 190

His Thr Glu Lys Thr Phe Tyr Asp Val Gly Val Val Lys Cys Ser Phe
        195                 200                 205

Glu Glu Pro Val Gly Ala Asn Gly Glu Gly Gly Phe Leu Val Leu Asn
    210                 215                 220

Met Thr Arg Asn Ser Ser Pro Pro Leu Val Asp His Ser Gly Ile
225                 230                 235                 240

Ile Glu Gln Ser Tyr Val Pro Val Phe Gln Glu Leu Pro Glu Glu Ile
```

```
            245                 250                 255
Ser Ser Ile Gln Phe Glu Gly Pro Phe Arg Phe Asp Tyr Ala Tyr Cys
        260                 265                 270

Ser Pro Leu Leu Thr Pro Ser Lys Asn Val Ser Ala Lys Tyr Val Lys
        275                 280                 285

Glu Trp Leu Met Tyr His Gln Gly Leu Trp Ser Glu Ser His Val His
        290                 295                 300

Tyr Phe Tyr Asp Ala Gly Gly Ile Asp Ser Arg Leu Leu Glu Val
305                 310                 315                 320

Phe Gln Pro Leu Met Glu Lys Lys Phe Leu Thr Val Ile Asp Met Arg
                325                 330                 335

Glu Leu Val Leu Phe Glu Ser Ala Gly Asp Gly His Gln Leu Val Ile
            340                 345                 350

Asn Asp Cys Leu Gln Arg Ser Arg Phe Leu Ala Thr Trp Ala Phe Phe
            355                 360                 365

Trp Asp Leu Asp Glu Tyr Leu Gln Leu Val Asn Ser Thr Ser Met Ala
370                 375                 380

Ala Leu Leu Arg Ser Tyr Glu Ser Ser Pro Trp Ile Ser Leu Ala Asn
385                 390                 395                 400

Leu Val Trp Ser Arg Thr Tyr Cys Lys Glu Thr Ser Ala Glu Asp Glu
                405                 410                 415

Trp Ala Val Glu Arg Met Arg Phe Arg Leu Arg Tyr Pro Thr Cys Gly
            420                 425                 430

Asp Glu Gln Arg Ala Glu Thr Cys His Gly Val Glu Gly His Arg Lys
            435                 440                 445

Trp Ile Ala Asn Pro Arg Lys Val Leu Val Ala Ser Ile His Arg Thr
        450                 455                 460

Val Glu Pro Glu Trp Asn Gly Glu Ile Leu Arg Ala Ser Ile Ala Arg
465                 470                 475                 480

Leu Asn His Phe His Gly Leu Ala Val Glu Gly Ser Ala Asn Ser Ser
                485                 490                 495

Cys Trp Ile Val Lys Lys Leu Asp Gln Val Asn Glu Ser Ser Leu Val
            500                 505                 510

Asp Gly Trp Trp Leu Lys Asp Glu Ser Phe Ala Val Ala Ala Met Glu
        515                 520                 525

Gln His Arg Lys Gly Leu
        530

<210> SEQ ID NO 40
<211> LENGTH: 425
<212> TYPE: PRT
<213> ORGANISM: Unknown
<220> FEATURE:
<223> OTHER INFORMATION: synthetic GALS C_elegans_NP_504545.2,
      glycosyltransferase family 92 (GT92) member,
      galactan synthase, beta-1,4,galactan synthase,
      beta-1,4 galactosyltransferase (GALS)

<400> SEQUENCE: 40

Met Pro Arg Ile Thr Ala Ser Lys Ile Val Leu Leu Ile Ala Leu Ser
1               5                   10                  15

Phe Cys Ile Thr Val Ile Tyr His Phe Pro Ile Ala Thr Arg Ser Ser
            20                  25                  30

Lys Glu Tyr Asp Glu Tyr Gly Asn Glu Tyr Glu Asn Val Ala Ser Ile
        35                  40                  45

Glu Ser Asp Ile Lys Asn Val Arg Arg Leu Leu Asp Glu Val Pro Asp
```

```
            50                  55                  60
Pro Ser Gln Asn Arg Leu Gln Phe Leu Lys Leu Asp Glu His Ala Phe
65                  70                  75                  80

Ala Phe Ser Ala Tyr Thr Asp Asp Arg Asn Gly Asn Met Gly Tyr Lys
                85                  90                  95

Tyr Val Arg Val Leu Met Phe Ile Thr Ser Gln Asp Asn Phe Ser Cys
            100                 105                 110

Glu Ile Asn Gly Arg Lys Ser Thr Asp Val Ser Leu Tyr Glu Phe Ser
        115                 120                 125

Glu Asn His Lys Met Lys Trp Gln Met Phe Ile Leu Asn Cys Lys Leu
    130                 135                 140

Pro Asp Gly Ile Asp Phe Asn Asn Val Ser Ser Val Lys Val Ile Arg
145                 150                 155                 160

Ser Thr Thr Lys Gln Phe Val Asp Val Pro Ile Arg Tyr Arg Ile Gln
                165                 170                 175

Asp Glu Lys Ile Ile Thr Pro Asp Glu Tyr Asp Tyr Lys Met Ser Ile
            180                 185                 190

Cys Val Pro Ala Leu Phe Gly Asn Gly Tyr Asp Ala Lys Arg Ile Val
        195                 200                 205

Glu Phe Ile Glu Leu Asn Thr Leu Gln Gly Ile Glu Lys Ile Tyr Ile
    210                 215                 220

Tyr Thr Asn Gln Lys Glu Leu Asp Gly Ser Met Lys Lys Thr Leu Lys
225                 230                 235                 240

Tyr Tyr Ser Asp Asn His Lys Ile Thr Leu Ile Asp Tyr Thr Leu Pro
                245                 250                 255

Phe Arg Glu Asp Gly Val Trp Tyr His Gly Gln Leu Ala Thr Val Thr
            260                 265                 270

Asp Cys Leu Leu Arg Asn Thr Gly Ile Thr Lys Tyr Thr Phe Phe Asn
        275                 280                 285

Asp Phe Asp Glu Phe Val Pro Val Ile Lys Ser Arg Thr Leu Phe
    290                 295                 300

Glu Thr Ile Ser Gly Leu Phe Glu Asp Pro Thr Ile Gly Ser Gln Arg
305                 310                 315                 320

Thr Ala Leu Lys Tyr Ile Asn Ala Lys Ile Lys Ser Ala Pro Tyr Ser
                325                 330                 335

Leu Lys Asn Ile Val Ser Glu Lys Arg Ile Glu Thr Arg Phe Thr Lys
            340                 345                 350

Cys Val Val Arg Pro Glu Met Val Phe Glu Gln Gly Ile His His Thr
        355                 360                 365

Ser Arg Val Ile Gln Asp Asn Tyr Lys Thr Val Ser His Gly Gly Ser
    370                 375                 380

Leu Leu Arg Val Tyr His Tyr Lys Asp Lys Tyr Cys Cys Glu Asp
385                 390                 395                 400

Glu Ser Leu Leu Lys Lys Arg His Gly Asp Gln Leu Arg Glu Lys Phe
                405                 410                 415

Asp Ser Val Val Gly Leu Leu Asp Leu
            420                 425

<210> SEQ ID NO 41
<211> LENGTH: 438
<212> TYPE: PRT
<213> ORGANISM: Unknown
<220> FEATURE:
<223> OTHER INFORMATION: synthetic GALS pigeon_ADC84389.1,
      glycosyltransferase family 92 (GT92) member,
``` galactan synthase, beta-1,4,galactan synthase,
beta-1,4 galactosyltransferase (GALS)

<400> SEQUENCE: 41

```
Met Ile His Cys Gly Lys Lys His Ile Cys Ala Phe Val Thr Cys Ile
1               5                   10                  15

Leu Ile Ser Ala Ser Ile Leu Met Tyr Ser Trp Lys Asp Pro Gln Leu
            20                  25                  30

Gln Asn Asn Ile Thr Arg Lys Ile Phe Gln Ala Thr Ser Ala Leu Pro
        35                  40                  45

Ala Ser Gln Leu Cys Arg Gly Lys Pro Ala Gln Asn Val Ile Thr Ala
    50                  55                  60

Leu Glu Asp Asn Arg Thr Phe Ile Ile Ser Pro Tyr Phe Asp Asp Arg
65                  70                  75                  80

Glu Ser Lys Val Thr Arg Val Ile Gly Ile Val His His Glu Asp Val
                85                  90                  95

Lys Gln Leu Tyr Cys Trp Phe Cys Cys Gln Pro Asp Gly Lys Ile Tyr
            100                 105                 110

Val Ala Arg Ala Lys Ile Asp Val His Ser Asp Arg Phe Gly Phe Pro
        115                 120                 125

Tyr Gly Ala Ala Asp Ile Val Cys Leu Glu Pro Glu Asn Cys Asn Pro
    130                 135                 140

Thr His Val Ser Ile His Gln Ser Pro His Ala Asn Ile Asp Gln Leu
145                 150                 155                 160

Pro Ser Phe Lys Ile Lys Asn Arg Lys Ser Glu Thr Phe Ser Val Asp
                165                 170                 175

Phe Thr Val Cys Ile Ser Ala Met Phe Gly Asn Tyr Asn Asn Val Leu
            180                 185                 190

Gln Phe Ile Gln Ser Val Glu Met Tyr Lys Ile Leu Gly Val Gln Lys
        195                 200                 205

Val Val Ile Tyr Lys Asn Asn Cys Ser Gln Leu Met Glu Lys Val Leu
    210                 215                 220

Lys Phe Tyr Met Glu Glu Gly Thr Val Glu Ile Ile Pro Trp Pro Ile
225                 230                 235                 240

Asn Ser His Leu Lys Val Ser Thr Lys Trp His Phe Ser Met Asp Ala
                245                 250                 255

Lys Asp Ile Gly Tyr Tyr Gly Gln Ile Thr Ala Leu Asn Asp Cys Ile
            260                 265                 270

Tyr Arg Asn Met Gln Arg Ser Lys Phe Val Val Leu Asn Asp Ala Asp
        275                 280                 285

Glu Ile Ile Leu Pro Leu Lys His Leu Asp Trp Lys Ala Met Met Ser
    290                 295                 300

Ser Leu Gln Glu Gln Asn Pro Gly Ala Gly Ile Phe Leu Phe Glu Asn
305                 310                 315                 320

His Ile Phe Pro Lys Thr Val Ser Thr Pro Val Phe Asn Ile Ser Ser
                325                 330                 335

Trp Asn Arg Val Pro Gly Val Asn Ile Leu Gln His Val His Arg Glu
            340                 345                 350

Pro Asp Arg Lys Glu Val Phe Asn Pro Lys Lys Met Ile Ile Asp Pro
        355                 360                 365

Arg Gln Val Val Gln Thr Ser Val His Ser Val Leu Arg Ala Tyr Gly
    370                 375                 380

Asn Ser Val Asn Val Pro Ala Asp Val Ala Leu Val Tyr His Cys Arg
385                 390                 395                 400
```

```
Val Pro Leu Gln Glu Glu Leu Pro Arg Glu Ser Leu Ile Arg Asp Thr
                405                 410                 415

Ala Leu Trp Arg Tyr Asn Ser Ser Leu Ile Thr Asn Val Asn Lys Val
            420                 425                 430

Leu His Gln Thr Val Leu
        435

<210> SEQ ID NO 42
<211> LENGTH: 1838
<212> TYPE: DNA
<213> ORGANISM: Arabidopsis thaliana
<220> FEATURE:
<223> OTHER INFORMATION: GALS1, At2g33570, glycosyltransferase family 92
      (GT92) member, galactan synthase 1,
      beta-1,4,galactan synthase, beta-1,4
      galactosyltransferase (GALS) cDNA

<400> SEQUENCE: 42
```

| | | | | |
|---|---|---|---|---|
| ctaatttcta | cacgccgtgt | cggcaaagcc | tctcgtcact | tctctctgac gcttgtcgtc | 60 |
| acttttgaat | tttttaatt | tttaaataat | tgataaccga | aacggtgcgt tttactcacc | 120 |
| gtcgtcggga | aaaaaaacat | gaggaaggaa | gttttgccgc | cggtgttatc aaccaccaca | 180 |
| gtatgtttcg | agaagaaacc | aataattgct | acattactag | ctctctctct cgtcatgatt | 240 |
| gtctggaacc | ttcctcctta | ctaccacaac | ctcatctcca | ccgctcgtcc ctgctccgcc | 300 |
| gtcaccacca | ccaccaccac | caccttactc | tcctcatcga | acttcacttc ggcggagaat | 360 |
| ttcaccacct | ctctctcaac | gacaactgca | gcagcttctc | agaagtacga ttcaactccc | 420 |
| tcagatccga | acaaacgcgt | tttccaaccg | ttcggaaacg | cggcggcgtt attcgtacta | 480 |
| atgggagctt | accgcggcgg | tccaacgacg | ttttccgtta | tcggactcgc gtcgaaaccg | 540 |
| atccacgttt | acggaaaacc | atggtacaag | tgtgagtgga | tatctaacaa tggaacttcg | 600 |
| attcgagcta | aagcacagaa | gattctacca | gattggggat | acggacgagt ctacaccgtc | 660 |
| gtcgtcgtca | attgcacttt | caattcaaac | cctaactccg | ataacaccgg aggtaaactc | 720 |
| attctcaacg | cttactacaa | cgaatctccc | aaactctttg | aacgattcac tacgttagaa | 780 |
| gaatcagctg | gaatctacga | cgaatcgaaa | tactcgccgc | cgtatcagta cgattacctc | 840 |
| tattgtggct | cgtcactgta | cggtaacgtg | agcgcgtcgc | gtatgagaga gtggatggct | 900 |
| taccacgctt | ggttctttgg | tgacaaatcg | cattttgttt | tccacgatgc tggtggtgtg | 960 |
| tcgccggaag | ttaggaaggt | tcttgagccg | tggattcgag | ctgggagggt cacggttcag | 1020 |
| aatattcggg | atcagtcgca | gtatgatggt | tactactata | atcagtttct tattgttaat | 1080 |
| gattgcttgc | atcggtatcg | atacgctgcg | aattggacct | tcttcttcga tgtcgatgag | 1140 |
| tatatctatt | tgccgcatgg | taatacactc | gaatccgtgc | tcgatgagtt ctcggttaac | 1200 |
| acgcagttta | cgattgagca | gaatccaatg | tctagtgttc | tttgcataaa cgactcttct | 1260 |
| caagattatc | caaggcaatg | ggatttgag | aaattgttat | ttaaggattc aaggacgaag | 1320 |
| atacgacgtg | atagaaaata | tgcaatccaa | gcgaagaacg | catttgctac aggagttcat | 1380 |
| atgtctgaaa | acattgtagg | caaaacacta | cacaagacag | agacaaagat tcgttattac | 1440 |
| cattaccaca | acaccataac | tgtgcatgag | gagctttgta | gagagatgtt accaaattca | 1500 |
| gccaagaaga | aggtgacatt | gtacaataag | cttccgtatg | tgtatgatga caacatgaag | 1560 |
| aagctagtga | agacgattaa | agagtttgag | cagaaaaaac | ttgggacgga tgtgaagaat | 1620 |
| ttctcatgac | cataatatag | ctgtaatctc | tctgataagc | attttgtcta taaggtata | 1680 |

```
gttgtttcta cattacatgt atcattttc attctgtttt gtcctctttt actatttcat    1740
taatgacttt gatcaatatt tttgaaaatt acttgtgttt tcttttgtta tgtattgaac    1800
ttaatagaaa ttagagttac tcaagacctt ggacatac                            1838

<210> SEQ ID NO 43
<211> LENGTH: 1983
<212> TYPE: DNA
<213> ORGANISM: Arabidopsis thaliana
<220> FEATURE:
<223> OTHER INFORMATION: GALS2, At5g44670, glycosyltransferase family 92
      (GT92) member, galactan synthase 1,
      beta-1,4,galactan synthase, beta-1,4
      galactosyltransferase (GALS) cDNA

<400> SEQUENCE: 43
aaattctcca aatttttct tctctctctc ttccctctgt cgcttcactt tccctctgct     60
tcatagttca tacgattctt cgattcgtct tcttcaatca gtgaagaaga actcaaaaga    120
tggctaaaga gagagaccaa aacactaaag acaaaaacct cctcatctgt ttcttatgga    180
acttctccgc cgagcttaag ctagctctaa tggcgttact cgttctctgc actttagcta    240
ctctcctccc ttttctacct tcttctttct ccatctccgc ttccgaactc cgtttctgca    300
tctcacgcat cgccgtaaac tccacctccg tcaacttcac caccgtcgtc gaaaagccag    360
tcttagataa cgctgtcaag ttaactgaga agccggtgtt ggataacggc gttacgaaac    420
agccgttaac tgaagagaag gtgttaaata acggcgttat taaacggacg tttactggtt    480
acggctgggc agcttataac ttcgtgttaa tgaacgctta cagaggcggc gttaacacat    540
tcgccgttat cggtttatca tctaaaccac ttcacgttta ctctcatccc acttaccgtt    600
gcgaatggat tccactaaac caatccgata accggatttt aaccgacggt accaaaatct    660
taaccgattg gggttacggt agagtttaca caaccgtcgt cgtaaactgt acttttccgt    720
caaacaccgt gataaaccct aaaaacaccg gaggtactct tctcctccac gcaaccaccg    780
gagatacaga ccggaacatc accgattcaa ttccggtact caccgaaact ccaaacaccg    840
tcgattttgc tctctacgaa tccaatctcc gccggcgaga aagtacgat tatctctatt     900 gtggatcttc tctctacggc aacttatcac cacagagaat cagagaatgg atcgcttacc    960
atgtaaggtt cttcggtgaa agatctcatt tgttctaca tgacgccgga gggattacag    1020
aggaagtgtt tgaggtttta aagccatgga tagagcttgg gagagttact gttcatgata    1080
ttagagaaca agagagattt gatggttatt atcataatca attcatggtg gtgaatgatt    1140
gtttgcatag gtatagattc atggcgaagt ggatgttttt cttcgatgtt gatgagttta    1200
tttatgttcc ggcgaagagt tcgatttcgt cggtgatggt atctttggag gaatattctc    1260
agtttactat tgaacagatg cctatgagta gtcagctttg ttacgacggt gatggtccgg    1320
cgaggactta caggaaatgg ggatttgaga aattggcgta tagagatgtg aagaaagtac    1380
cacgacggga taggaagtat gcggttcaac cgcggaacgt atttgcgaca ggggttcaca    1440
tgtctcagca tctacaaggg aagacgtatc acagagcgga agggaaaata cgctattttc    1500
actaccatgg ttcaatctcg cagcgtcgtg agccttgtcg tcatctttat aacggtaccc    1560
gtatcgttca tgagaacaat ccttacgtgc ttgataccac aatgcgtgat attggtctcg    1620
cggtgaagac gtttgagatt aggacgattg gagatcgctt gcttaggacg agacaatgaa    1680
ggcaggagaa gaatggttaa agacatgtta tcatcattat gcgttgtaac gtaaatcttt    1740
tagagtatta tttaggcgaa tgtaacaatt ttcatggttt tttgtttagt atattctttt    1800
```

-continued

| attgtattat | aaaatgggtt | cgtacataga | gatcatcata | cagctcagat | tcttggtata | 1860 |
| taagcatctt | ttttatgggc | tttataattt | tttccgttat | ttatggaaaa | gtgctttata | 1920 |
| taaattagtg | aaagttgttg | tggtcttcca | tggatctttg | tcgtgttaat | taaaagtttc | 1980 |
| cac | | | | | | 1983 |

<210> SEQ ID NO 44
<211> LENGTH: 1993
<212> TYPE: DNA
<213> ORGANISM: Arabidopsis thaliana
<220> FEATURE:
<223> OTHER INFORMATION: GALS3, At4g20170, glycosyltransferase family 92
      (GT92) member, galactan synthase 1,
      beta-1,4,galactan synthase, beta-1,4
      galactosyltransferase (GALS) cDNA

<400> SEQUENCE: 44

| aaaagtgaga | gacacacaac | ttcggagcga | atctattctt | cttcttcttc | ttcttcttct | 60 |
| tcttcttctt | cctccgtttt | tttcatcttc | ttctctgttt | cgagagatcc | actagtgaaa | 120 |
| gagtcagcac | catggccatg | gtcaaagaga | agaacaaaa | cactaaagac | aaaaaactcc | 180 |
| tcgtcggcgt | catttggaac | ttctccgccg | agctcaagct | cactttcatg | gcgttacttg | 240 |
| ttctctgcac | tttagctact | ctcttacctt | tcataccttc | ttcattctct | ctctccactt | 300 |
| ccgatttccg | cttctgcatc | tcacgcttct | cctccgccgt | ccctctcaac | accaccacca | 360 |
| ccgtagaaga | atcatcatcc | tcaccgtcac | cggagaagaa | cctagatcga | gttttggata | 420 |
| acggagttat | taaacggacg | tttactggct | acggctcagc | agcttataac | ttcgtctcaa | 480 |
| tgagtgctta | cagaggcggc | gttaactcat | tcgccgttat | cggattatca | tcaaaaccat | 540 |
| tacacgtgta | cggtcatcct | tcgtatagat | gcgaatgggt | ctcattagac | ccgactcaag | 600 |
| atccgatttc | aacaaccggg | tttaaaatct | taaccgattg | gggttacgga | cggatctaca | 660 |
| caacagtcgt | cgttaactgt | actttctcat | caatctccgc | cgtgaatcca | caaaactccg | 720 |
| gtggaactct | catcctccac | gccaccaccg | gagatccaac | tctcaatctc | accgattcaa | 780 |
| tctcagtcct | aaccgaacct | cccaaatccg | tcgatttcga | tctctataac | tccacgaaga | 840 |
| agacgaagaa | gtacgattat | ctctattgcg | gatcgtcctt | atacggtaac | ctaagtccgc | 900 |
| aacgagttag | agaatggatc | gcttaccacg | ttagattctt | cggtgaacgg | tcacatttcg | 960 |
| tgctacacga | cgccggaggg | attcatgagg | aagtgttcga | ggttttaaag | ccatggattg | 1020 |
| agctagggag | agtgacgtta | catgatatta | gagatcaaga | acgattcgat | ggatattatc | 1080 |
| ataatcagtt | catgatagtg | aatgattgtt | tgcataggta | tagattcatg | acgaagtgga | 1140 |
| tgttcttctt | tgatgttgat | gagtttttac | atgttccagt | gaaagagacg | atttcgtctg | 1200 |
| tgatggaatc | tttggaggaa | tattctcagt | ttactattga | acagatgcct | atgagtagtc | 1260 |
| ggatttgtta | ttccggtgat | ggtccggcga | gaacttacag | gaaatgggga | attgagaaac | 1320 |
| tggcatatag | agacgtcaag | aaggttccaa | gacgggatcg | aaaatacgct | gtccagccgg | 1380 |
| agaatgtatt | cgcgacaggc | gtacacatgt | ctcagaatct | acaagggaaa | acataccaca | 1440 |
| aggctgaaag | caaaatccgt | tacttccact | accatggttc | gatctctcag | cgccgcgagc | 1500 |
| cttgtcgtca | acttttttaac | gattctcgag | tcgtgttcga | gaacactcct | tatgtgctag | 1560 |
| acactacaat | atgtgatgtt | ggccttgctg | tgagaacgtt | cgagttgaga | acgatcggtg | 1620 |
| atcggctgct | acgacaagaa | caatgaagag | atggcaaaaa | tgaatagtga | atgtaatcaa | 1680 |
| tctttagaaa | gaagaattag | aaggtgttaa | gatgagttac | tttgtattat | tttcttttgg | 1740 |

-continued

```
gggtatattc ttttattgta tcatataatt tgggtaatgg gttcattaat acagcttgaa    1800
aatactcttt ggtatatata ttctgtatga tgtatgattt agaaaaaagg tctctgagta    1860
tataatctag tgatgataat tgtggagatc aagtaatatc actgtttgta tttgattact    1920
gtactcttag ttgacaaaaa gaaaatgtca atatccattg gtgttactcc agtaatccat    1980
atggaacgtt gat                                                       1993

<210> SEQ ID NO 45
<211> LENGTH: 350
<212> TYPE: PRT
<213> ORGANISM: Arabidopsis thaliana
<220> FEATURE:
<223> OTHER INFORMATION: UDP-D-glucose/UDP-D-galactose 4-epimerase 2
      (UGE2)

<400> SEQUENCE: 45

Met Ala Lys Ser Val Leu Val Thr Gly Gly Ala Gly Tyr Ile Gly Ser
1               5                   10                  15

His Thr Val Leu Gln Leu Leu Glu Gly Gly Tyr Ser Ala Val Val Val
                20                  25                  30

Asp Asn Tyr Asp Asn Ser Ser Ala Ala Ser Leu Gln Arg Val Lys Lys
            35                  40                  45

Leu Ala Gly Glu Asn Gly Asn Arg Leu Ser Phe His Gln Val Asp Leu
        50                  55                  60

Arg Asp Arg Pro Ala Leu Glu Lys Ile Phe Ser Glu Thr Lys Phe Asp
65                  70                  75                  80

Ala Val Ile His Phe Ala Gly Leu Lys Ala Val Gly Glu Ser Val Glu
                85                  90                  95

Lys Pro Leu Leu Tyr Tyr Asn Asn Asn Ile Val Gly Thr Val Thr Leu
            100                 105                 110

Leu Glu Val Met Ala Gln Tyr Gly Cys Lys Asn Leu Val Phe Ser Ser
        115                 120                 125

Ser Ala Thr Val Tyr Gly Trp Pro Lys Glu Val Pro Cys Thr Glu Glu
    130                 135                 140

Ser Pro Ile Ser Ala Thr Asn Pro Tyr Gly Arg Thr Lys Leu Phe Ile
145                 150                 155                 160

Glu Glu Ile Cys Arg Asp Val His Arg Ser Asp Ser Glu Trp Lys Ile
                165                 170                 175

Ile Leu Leu Arg Tyr Phe Asn Pro Val Gly Ala His Pro Ser Gly Tyr
            180                 185                 190

Ile Gly Glu Asp Pro Leu Gly Val Pro Asn Asn Leu Met Pro Tyr Val
        195                 200                 205

Gln Gln Val Ala Val Gly Arg Arg Pro His Leu Thr Val Phe Gly Thr
    210                 215                 220

Asp Tyr Lys Thr Lys Asp Gly Thr Gly Val Arg Asp Tyr Ile His Val
225                 230                 235                 240

Met Asp Leu Ala Asp Gly His Ile Ala Ala Leu Arg Lys Leu Asp Asp
                245                 250                 255

Leu Lys Ile Ser Cys Glu Val Tyr Asn Leu Gly Thr Gly Asn Gly Thr
            260                 265                 270

Ser Val Leu Glu Met Val Ala Ala Phe Glu Lys Ala Ser Gly Lys Lys
        275                 280                 285

Ile Pro Leu Val Met Ala Gly Arg Arg Pro Gly Asp Ala Glu Val Val
    290                 295                 300
```

```
Tyr Ala Ser Thr Glu Lys Ala Glu Arg Glu Leu Asn Trp Lys Ala Lys
305                 310                 315                 320

Asn Gly Ile Glu Glu Met Cys Arg Asp Leu Trp Asn Trp Ala Ser Asn
            325                 330                 335

Asn Pro Tyr Gly Tyr Asn Ser Ser Asn Gly Ser Ser Ser
        340                 345                 350

<210> SEQ ID NO 46
<211> LENGTH: 18
<212> TYPE: PRT
<213> ORGANISM: Artificial Sequence
<220> FEATURE:
<223> OTHER INFORMATION: GALS highly conserved region
<220> FEATURE:
<221> NAME/KEY: VARIANT
<222> LOCATION: (1)...(1)
<223> OTHER INFORMATION: Xaa = Phe, Tyr or Val
<220> FEATURE:
<221> NAME/KEY: VARIANT
<222> LOCATION: (3)...(3)
<223> OTHER INFORMATION: Xaa = Asn, Ser or Thr
<220> FEATURE:
<221> NAME/KEY: VARIANT
<222> LOCATION: (10)...(10)
<223> OTHER INFORMATION: Xaa = Leu or Gln

<400> SEQUENCE: 46

Xaa Gly Xaa Ala Ala Ala Leu Phe Val Xaa Met Gly Ala Tyr Arg Gly
1               5                   10                  15

Gly Pro

<210> SEQ ID NO 47
<211> LENGTH: 19
<212> TYPE: PRT
<213> ORGANISM: Artificial Sequence
<220> FEATURE:
<223> OTHER INFORMATION: GALS highly conserved region

<400> SEQUENCE: 47

Ser Lys Pro Ile His Val Tyr Gly Lys Pro Trp Tyr Lys Cys Glu Trp
1               5                   10                  15

Ile Ser Asn

<210> SEQ ID NO 48
<211> LENGTH: 21
<212> TYPE: PRT
<213> ORGANISM: Artificial Sequence
<220> FEATURE:
<223> OTHER INFORMATION: GALS highly conserved region

<400> SEQUENCE: 48

Lys Ile Leu Pro Asp Trp Gly Tyr Gly Arg Val Tyr Thr Val Val
1               5                   10                  15

Val Val Asn Cys Thr Phe
                20

<210> SEQ ID NO 49
<211> LENGTH: 6
<212> TYPE: PRT
<213> ORGANISM: Artificial Sequence
<220> FEATURE:
<223> OTHER INFORMATION: GALS highly conserved region
<220> FEATURE:
<221> NAME/KEY: VARIANT
<222> LOCATION: (3)...(3)
<223> OTHER INFORMATION: Xaa = Lys or Arg
```

```
<220> FEATURE:
<221> NAME/KEY: VARIANT
<222> LOCATION: (6)...(6)
<223> OTHER INFORMATION: Xaa = Leu, Val or Ile

<400> SEQUENCE: 49

Gly Gly Xaa Leu Ile Xaa
1               5

<210> SEQ ID NO 50
<211> LENGTH: 12
<212> TYPE: PRT
<213> ORGANISM: Artificial Sequence
<220> FEATURE:
<223> OTHER INFORMATION: GALS highly conserved region
<220> FEATURE:
<221> NAME/KEY: VARIANT
<222> LOCATION: (2)...(2)
<223> OTHER INFORMATION: Xaa = Asp or Glu
<220> FEATURE:
<221> NAME/KEY: VARIANT
<222> LOCATION: (11)...(11)
<223> OTHER INFORMATION: Xaa = Tyr or Phe

<400> SEQUENCE: 50

Tyr Xaa Tyr Leu Tyr Cys Gly Ser Ser Leu Xaa Gly
1               5                   10

<210> SEQ ID NO 51
<211> LENGTH: 12
<212> TYPE: PRT
<213> ORGANISM: Artificial Sequence
<220> FEATURE:
<223> OTHER INFORMATION: GALS highly conserved region

<400> SEQUENCE: 51

Arg Glu Trp Met Ala Tyr His Ala Trp Phe Phe Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: GALS highly conserved region

<400> SEQUENCE: 52

Ser His Phe Val Phe His Asp Ala Gly Gly
1               5                   10

<210> SEQ ID NO 53
<211> LENGTH: 6
<212> TYPE: PRT
<213> ORGANISM: Artificial Sequence
<220> FEATURE:
<223> OTHER INFORMATION: GALS highly conserved region

<400> SEQUENCE: 53

Gln Asn Ile Arg Asp Gln
1               5

<210> SEQ ID NO 54
<211> LENGTH: 31
<212> TYPE: PRT
<213> ORGANISM: Artificial Sequence
<220> FEATURE:
<223> OTHER INFORMATION: GALS highly conserved region
```

```
<400> SEQUENCE: 54

Gly Tyr Tyr Tyr Asn Gln Phe Leu Ile Val Asn Asp Cys Leu His Arg
1               5                   10                  15

Tyr Arg Tyr Ala Ala Asn Trp Thr Phe Phe Asp Val Asp Glu Tyr
            20                  25                  30

<210> SEQ ID NO 55
<211> LENGTH: 9
<212> TYPE: PRT
<213> ORGANISM: Artificial Sequence
<220> FEATURE:
<223> OTHER INFORMATION: GALS highly conserved region

<400> SEQUENCE: 55

Phe Thr Ile Glu Gln Asn Pro Met Ser
1               5

<210> SEQ ID NO 56
<211> LENGTH: 9
<212> TYPE: PRT
<213> ORGANISM: Artificial Sequence
<220> FEATURE:
<223> OTHER INFORMATION: GALS highly conserved region

<400> SEQUENCE: 56

Trp Gly Phe Glu Lys Leu Leu Phe Lys
1               5

<210> SEQ ID NO 57
<211> LENGTH: 9
<212> TYPE: PRT
<213> ORGANISM: Artificial Sequence
<220> FEATURE:
<223> OTHER INFORMATION: GALS highly conserved region

<400> SEQUENCE: 57

Arg Arg Asp Arg Lys Tyr Ala Ile Gln
1               5

<210> SEQ ID NO 58
<211> LENGTH: 9
<212> TYPE: PRT
<213> ORGANISM: Artificial Sequence
<220> FEATURE:
<223> OTHER INFORMATION: GALS highly conserved region

<400> SEQUENCE: 58

Arg Tyr Tyr His Tyr His Asn Ser Ile
1               5

<210> SEQ ID NO 59
<211> LENGTH: 5
<212> TYPE: PRT
<213> ORGANISM: Artificial Sequence
<220> FEATURE:
<223> OTHER INFORMATION: GALS highly conserved region

<400> SEQUENCE: 59

Glu Leu Cys Arg Glu
1               5
```